(12) United States Patent
Toranto

(10) Patent No.: US 12,295,849 B2
(45) Date of Patent: May 13, 2025

(54) MANDIBULAR RECONSTRUCTION SYSTEMS AND METHODS

(71) Applicant: Jason D. Toranto, San Diego, CA (US)

(72) Inventor: Jason D. Toranto, San Diego, CA (US)

(*) Notice: Subject to any disclaimer, the term of this patent is extended or adjusted under 35 U.S.C. 154(b) by 0 days.

(21) Appl. No.: 18/440,910

(22) Filed: Feb. 13, 2024

(65) Prior Publication Data

US 2024/0252320 A1 Aug. 1, 2024

Related U.S. Application Data

(63) Continuation of application No. 18/102,009, filed on Jan. 26, 2023.

(51) Int. Cl.
*A61F 2/28* (2006.01)
*A61B 17/15* (2006.01)
(Continued)

(52) U.S. Cl.
CPC ............ *A61F 2/2803* (2013.01); *A61B 17/15* (2013.01); *A61B 17/176* (2013.01);
(Continued)

(58) Field of Classification Search
CPC .................. A61F 2/2803; A61B 17/8071
See application file for complete search history.

(56) References Cited

U.S. PATENT DOCUMENTS

2002/0062127 A1* 5/2002 Schumacher ...... A61B 17/8888
　　　　　　　　　　　　　　　　　　　　606/300
2011/0230885 A1* 9/2011 Weiner ............... A61B 17/8019
　　　　　　　　　　　　　　　　　　　　606/71
(Continued)

FOREIGN PATENT DOCUMENTS

EP　　2581777 A1　　9/2016
EP　　3195816 A1　　7/2017
(Continued)

OTHER PUBLICATIONS

PCT International Search Report and Written Opinion mailed on Sep. 21, 2022, issued in related International Application No. PCT/US2022/028856 (12 pages).
(Continued)

*Primary Examiner* — Brian A Dukert
*Assistant Examiner* — Yasniary De La Caridad Morales
(74) *Attorney, Agent, or Firm* — Sheppard Mullin Richter & Hampton LLP

(57) ABSTRACT

In general, one aspect disclosed features a method comprising: providing a bone section; attaching a cutting guide to the bone section; cutting the bone section into multiple bone graft sections using the cutting guide; arranging the multiple bone graft sections in a neo-mandible position; attaching a temporary fixation plate to the multiple bone graft sections after arranging the multiple bone graft sections in the neo-mandible position; removing the cutting guide from the multiple bone graft sections after attaching the temporary fixation plate; attaching a final fixation plate to the multiple bone graft sections after removing the cutting guide; and removing the temporary fixation plate from the multiple bone graft sections after attaching the final fixation plate to create a neo-mandible assembly.

22 Claims, 67 Drawing Sheets

(51) Int. Cl.
    *A61B 17/17*     (2006.01)
    *A61B 17/80*     (2006.01)
    *A61B 17/86*     (2006.01)
    *A61C 8/00*     (2006.01)
    *A61F 2/30*     (2006.01)
    *A61F 2/46*     (2006.01)

(52) U.S. Cl.
    CPC .......... *A61C 8/0031* (2013.01); *A61C 8/0093* (2013.01); *A61F 2/2846* (2013.01); *A61F 2/4644* (2013.01); *A61B 17/8071* (2013.01); *A61B 17/86* (2013.01); *A61F 2002/30433* (2013.01); *A61F 2220/0091* (2013.01)

(56) References Cited

U.S. PATENT DOCUMENTS

| | | | |
|---|---|---|---|
| 2013/0304075 A1* | 11/2013 | Tseng | A61B 17/15 606/102 |
| 2014/0094811 A1 | 4/2014 | Davison et al. | |
| 2017/0014169 A1* | 1/2017 | Dean | A61B 17/8071 |
| 2018/0103990 A1 | 4/2018 | Thiel et al. | |
| 2018/0221153 A1* | 8/2018 | Daniel | A61F 2/2846 |
| 2019/0070006 A1 | 3/2019 | Goh et al. | |
| 2019/0076252 A1* | 3/2019 | Karg | A61F 2/30771 |
| 2019/0290436 A1 | 9/2019 | Daniel et al. | |
| 2020/0222060 A1 | 7/2020 | Herzog et al. | |
| 2020/0289271 A1* | 9/2020 | Nedrud | A61F 2/2803 |
| 2021/0137537 A1 | 5/2021 | Zille | |
| 2022/0362023 A1 | 11/2022 | Toranto | |

FOREIGN PATENT DOCUMENTS

| | | | |
|---|---|---|---|
| ES | 2581777 A1 * | 9/2016 | ............ A61B 17/15 |
| RU | 2610533 C1 | 2/2017 | |

OTHER PUBLICATIONS

PCT International Search Report and Written Opinion mailed on Apr. 14, 2023, issued in related International Application No. PCT/US2023/011650 (10 pages).

\* cited by examiner

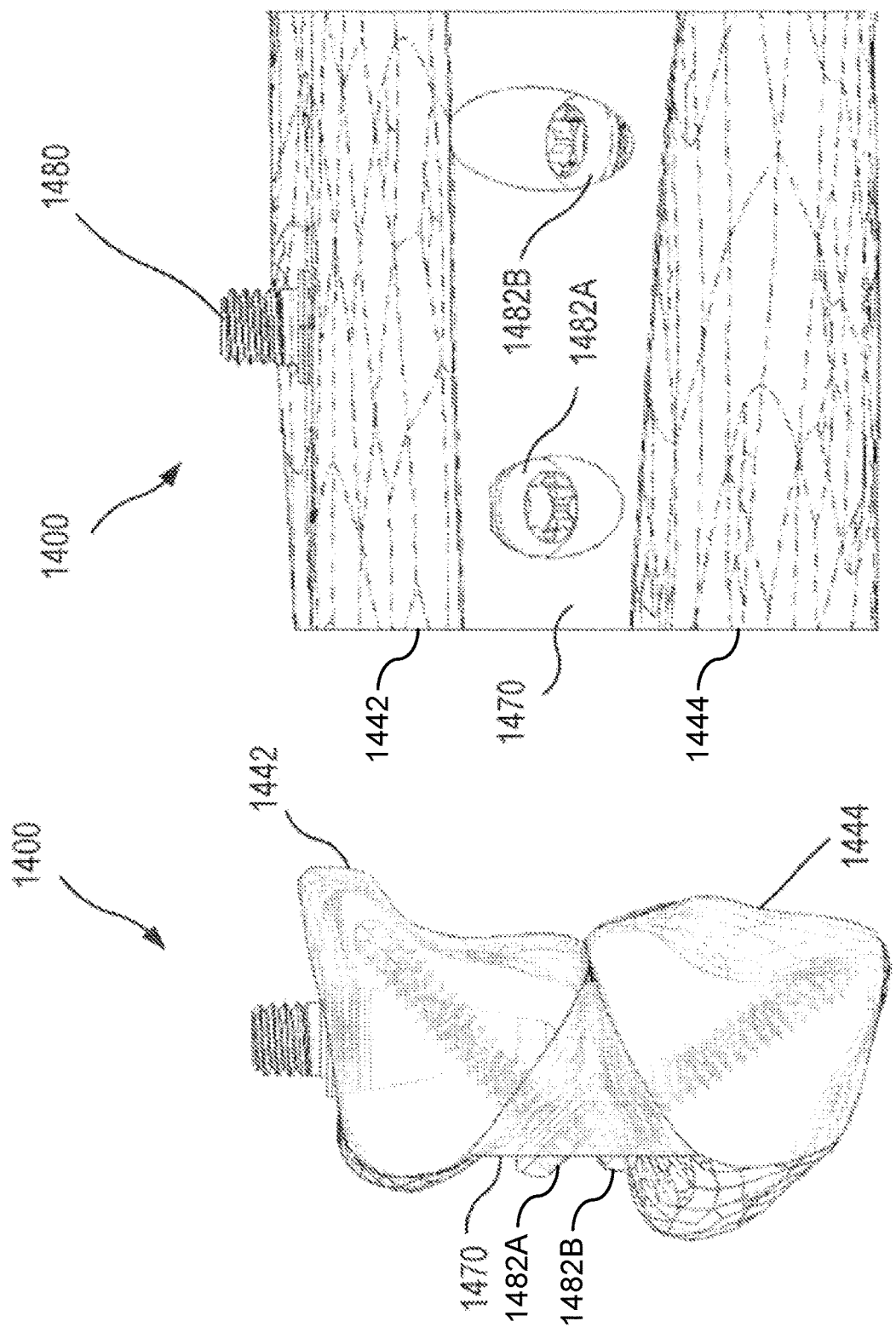

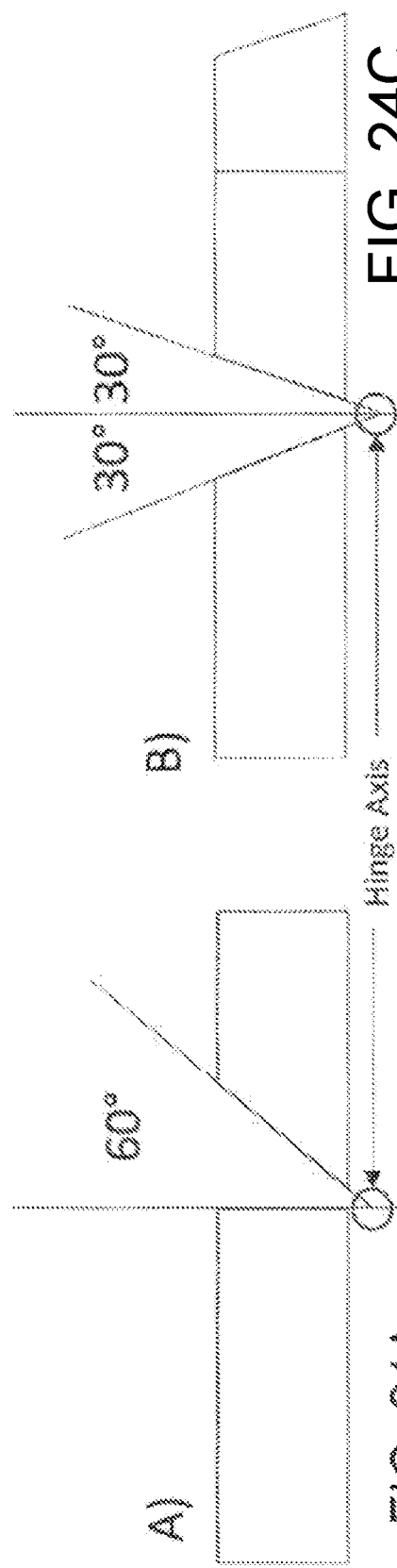
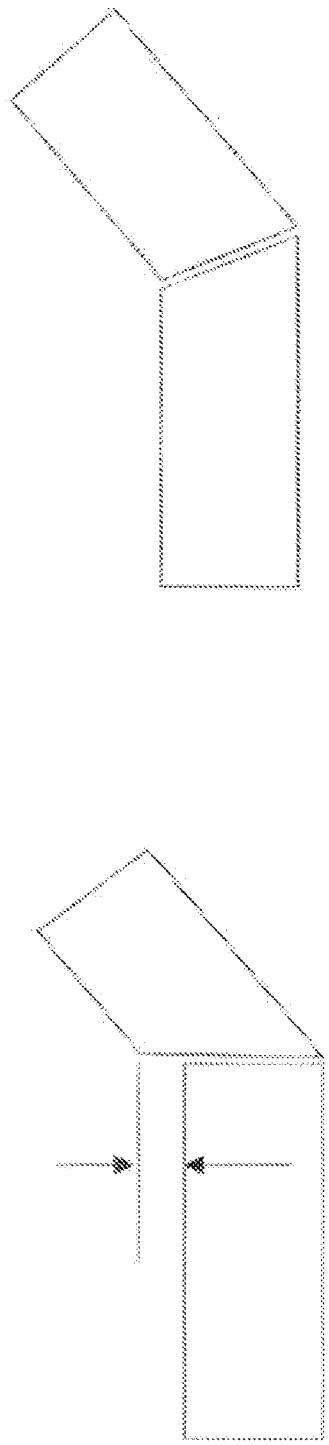
FIG. 24A FIG. 24B FIG. 24C FIG. 24D

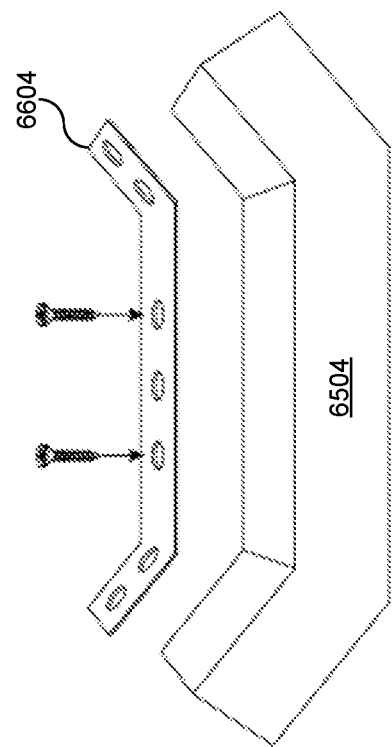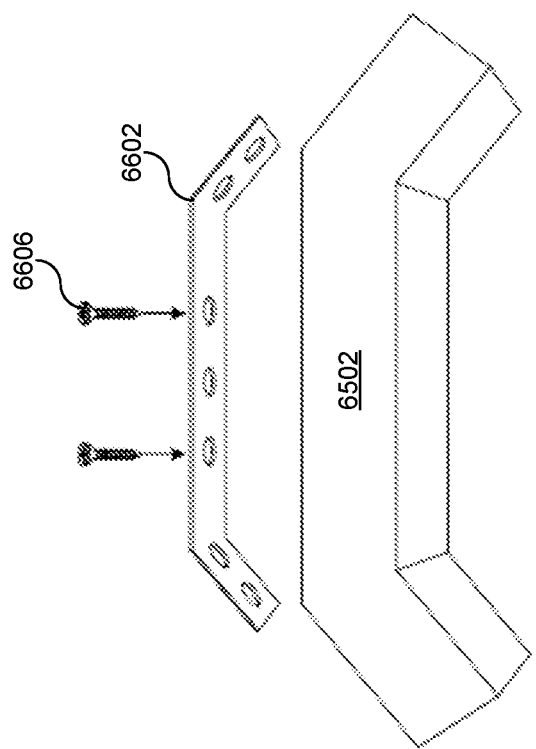
FIG. 66

MANDIBULAR RECONSTRUCTION SYSTEMS AND METHODS

CROSS REFERENCE TO RELATED APPLICATION

This application is a continuation of U.S. patent application Ser. No. 18/102,009, filed on Jan. 26, 2023, entitled "MANDIBULAR RECONSTRUCTION SYSTEMS AND METHODS", the content of which is incorporated herein by reference.

BACKGROUND OF THE INVENTION

Embodiments of the present invention relate generally to surgical systems and methods, and in particular encompass mandibular reconstruction patient specific cutting/alignment guides, triangular plate, and related techniques for their use and implementation.

BRIEF SUMMARY OF THE INVENTION

A patient specific cutting guide and alignment fixture can be used to precisely cut fibular bone grafts at predetermined locations and then conform grafts into a final orientation to construct a neo-mandible. In some embodiments, a patient specific triangular plate is installed between two rows of fibular grafts to provide the jaw structure while also allowing the screws going into fibular grafts to be recessed. Two rows of fibular grafts can be used on a case-by-case basis to build up bone height for positioning dental implants to be installed concurrently. Embodiments of the present invention encompass single barrel or single rowed configurations as well. Relatedly, in some embodiments, a single row of fibular grafts may be used to achieve bone height for positioning dental implants.

In exemplary embodiments, there would be an area of the native mandible that needs reconstruction. Often this would be a defect created at the time of surgery through mandibular osteotomies. In some cases, the area that needs reconstruction may be referred to as a defect. In an exemplary method, surgical steps can include sectioning the free flap fibula and removing it from the leg of the patient. Next, the cutting/alignment guide can be located and secured to the fibula using temporary fixation screws, for example two for each section. Thereafter, cuts can be made along the cutting guide surfaces carefully as to not cut the vascular pedicle leash. Once excess bone is removed, the cutting/alignment guide can be bent or shaped to form the neo-mandible. Next, a triangular plate can be installed in the recess superior to the cutting guide and monocortical screws can be driven into the fibula graft sections, securing them to the plate. Then the neo-mandible can be placed in the native mandibular defect region and an occlusal splint can be inserted to verify alignment. The plate can be secured to the native mandible using bicortical screws. Next, dental implants can be installed in predetermined locations that do not interfere with the cortical screws, while also angled correctly for proper occlusion with dental bridge.

In one aspect, embodiments of the present invention encompass cutting and alignment guide assemblies for use in orthopedic and dental surgical procedures. Exemplary cutting and alignment guide embodiments may be used for microsurgical, plastic surgical, otolaryngological, maxillofacial, and other surgical applications. Exemplary' cutting and alignment guide assemblies can include a first section configured to engage a first bone graft section, a second section configured to engage a second bone graft section, a first fixation mechanism configured to couple the first section with the first bone graft section, and a second fixation mechanism configured to couple the second section with the second bone graft section. The first section and the second section can be coupled via a hinge mechanism. In some cases, the hinge mechanism enables the first section and the second section to pivot relative to one another such that the assembly can be converted from a straight orientation to a bent configuration. In some cases, the first fixation mechanism includes a first temporary fixation screw. In some cases, the first fixation mechanism includes a first temporary fixation screw and a second temporary fixation screw. In some cases, the first fixation mechanism includes a first temporary fixation screw and a second temporary fixation screw, and the second fixation mechanism includes a first temporary fixation screw and a second temporary fixation screw. In some cases, once the hinge mechanism is utilized to couple the first and second bone graft sections together, the first bone graft section and second bone graft section can be temporarily fixated together using a first temporary fixation screw and a second temporary fixation screw on the first bone graft segment, a first temporary fixation screw and a second temporary fixation screw on the second bone graft segment and a temporary fixation plate.

According to some embodiments, a hinge mechanism of a cutting and alignment guide assembly can include a flexural hinge or a pinned hinge. In some cases, the hinge mechanism is a flexural hinge. In some cases, the hinge mechanism is a pinned hinge. In some cases, a cutting and alignment guide assembly can include a first magnet and a second magnet in operative association with the first section. In some cases, a cutting and alignment guide assembly can further include a third section configured to engage a third bone graft section, and a third fixation mechanism configured to couple the third section with the third bone graft section. The second section and the third section can be coupled via a second hinge mechanism. In some cases, the second hinge mechanism includes a flexural hinge or a pinned hinge.

According to some embodiments, a cutting and alignment guide assembly can include a third section configured to engage a third bone graft section, a fourth section configured to engage a fourth bone graft section, a third fixation mechanism configured to couple the third section with the third bone graft section, and a fourth fixation mechanism configured to couple the fourth section with the fourth bone graft section. In some cases, the second section and the third section are coupled via a second hinge mechanism, and the third section and the fourth section are coupled via a third hinge mechanism. Although the description of exemplary embodiments may include only four fibular sections, it is understood that the present disclosure encompasses configurations involving a ramus to symphysis reconstruction or condyle to condyle reconstruction having five pieces, six pieces (e.g. angle to angle reconstruction with full double barrel or double rowed), or more than six pieces. Relatedly, in some cases, a cutting and alignment guide assembly can include a fifth section configured to engage a fifth bone graft section, and a sixth section configured to engage with a sixth bone graft section. In some cases, the fourth and fifth section are coupled via a fourth hinge mechanism, and the fifth and the sixth section are coupled via a fifth hinge mechanism. In other cases, a cutting and alignment guide assembly can include seven or more sections configured to engage with seven or more bone graft sections.

According to some embodiments, a cutting and alignment guide assembly can be configured to support a saw blade at a first cutting position and at a second cutting position, and a distance between the first cutting position and the second cutting position can have a value within a range from about 20 mm to about 100 mm. In some cases, the assembly is configured to support a saw blade at a first cutting position and at a second cutting position, and a distance between the first cutting position and the second cutting position has a value within a range from about 30 mm to about 50 mm. In some cases, the assembly is configured to accommodate a saw blade with a cutting edge length having a value within a range from about 25 mm to about 45 mm. In some cases, the assembly is configured to accommodate a saw blade with a thickness having a value of about 0.5 mm. In some cases, a cutting and alignment guide assembly can include or be used on conjunction with a triangular cross-sectional plate. In some cases, a triangular cross-sectional plate can have one or more recessed holes configured to receive one or more screws, respectively. In some cases, a cutting and alignment guide assembly can be configured to produce a first preoperative planning cutting plane and a second preoperative planning cutting plane, where the first preoperative planning cutting plane and the second preoperative planning cutting plane are disposed equally about an orthogonal axis. In some cases, the axis can be a hinge axis.

In another aspect, embodiments of the present invention encompass neo-mandible assemblies for implantation on a native mandible or native mandibular defect region of a patient. Exemplary neo-mandible assemblies include a first section, a first bone graft section, a first fixation mechanism that secures the first section with the first bone graft section, a second section, a second bone graft section, a second fixation mechanism that secures the second section with the second bone graft section, and a coupling mechanism that couples the first section and the second section together. In some cases, the coupling mechanism includes a hinge mechanism that couples the first section and the second section together in pivotal association. In some embodiments, neo-mandible assemblies can further include a third section, a third bone graft section, and a third fixation mechanism that secures the third section with the third bone graft section. In some embodiments, neo-mandible assemblies can further include a third section, a third bone graft section, a third fixation mechanism that secures the third section with the third bone graft section, a fourth section, a fourth bone graft section, and a fourth fixation mechanism that secures the fourth section with the fourth bone graft section.

In another aspect, exemplary neo-mandible assemblies include a first upper bone graft section, a first lower bone graft section, a second upper bone graft section, a second lower bone graft section, a first upper fixation mechanism that secures the first section with the second upper bone graft section, and a first lower fixation mechanism that secures the first section with the second lower bone graft section. There may be more sections, as well. In some cases, neo-mandible assemblies can further include a dental tensioning plate that is secured to the first upper bone graft section and to the second upper bone graft section. In some cases, neo-mandible assemblies can further include a dental tensioning plate that is secured to the first upper bone graft section via a first dental fixation mechanism and to the second upper bone graft section via a second dental fixation mechanism. In some cases, neo-mandible assemblies can further include a dental tensioning plate that is secured to the first upper bone graft section via a first dental fixation mechanism having one or more dental screws and to the second upper bone graft section via a second dental fixation mechanism having one or more dental screws. In some cases, neo-mandible assemblies can further include a dental tensioning plate that is secured to the first upper bone graft section via a first dental fixation mechanism having a first snap abutment and a first dental screw and to the second upper bone graft section via a second dental fixation mechanism having a second snap abutment and a second dental screw. In another aspect, exemplary neo-mandible assemblies include a first section, a first upper bone graft section, a first lower bone graft section, a first upper fixation mechanism that secures the first section with the first upper bone graft section, a first lower fixation mechanism that secures the first section with the first lower bone graft section, a second section, a second upper bone graft section, a second lower bone graft section, a second upper fixation mechanism that secures the second section with the second upper bone graft section, and a second lower fixation mechanism that secures the second section with the second lower bone graft section. In some cases, neo-mandible assemblies can further include a dental tensioning plate that operates to hold the first section and the second section in fixed position relative to one another. In some cases, neo-mandible assemblies can further include a dental tensioning plate that is secured to the first upper bone graft section and to the second upper bone graft section. In some cases, neo-mandible assemblies can further include a dental tensioning plate that is secured to the first upper bone graft section via a first dental fixation mechanism and to the second upper bone graft section via a second dental fixation mechanism. In some cases, neo-mandible assemblies can further include a dental tensioning plate that is secured to the first upper bone graft section via a first dental fixation mechanism having one or more dental screws and to the second upper bone graft section via a second dental fixation mechanism having one or more dental screws. In some cases, neo-mandible assemblies can further include a dental tensioning plate that is secured to the first upper bone graft section via a first dental fixation mechanism having a first snap abutment and a first dental screw and to the second upper bone graft section via a second dental fixation mechanism having a second snap abutment and a second dental screw. In some cases, the dental tensioning plate does not involve dental implants and is instead a temporary fixation plate. Screws are placed to hold the plate in place, which in turn holds the bone graft segments in place. This allows the fixation mechanisms that have been applied to the bone graft sections to be removed and the final fixation plate to be applied to the segments. The temporary fixation plate and screws are then removed.

In another aspect, embodiments of the present invention encompass methods for implanting a neo-mandible assembly on a native mandible of a patient. Exemplary methods include removing a free flap fibula bone from the patient, positioning the cutting and alignment guide assembly adjacent to the fibula bone of the patient, where the cutting and alignment guide assembly includes a first section and a second section. Methods can also include using the cutting and alignment guide assembly as a cutting guide to cut a first bone graft segment and a second bone graft segment from the fibula bone. Methods can further include fixing the first bone graft segment with the first section of the cutting and alignment guide assembly and fixing the second bone graft segment with the second section of the cutting and alignment guide assembly so as to produce the neo-mandible assembly. Methods may also include implanting the neo-mandible assembly on the native mandible or native mandibular defect of the patient. Some methods may include using the cutting and alignment guide assembly as a cutting guide to cut a third bone graft segment the fibula bone. Some methods may include fixing the third bone graft segment with a third section of the cutting and alignment guide assembly prior to implanting the neo-mandible assembly on the native mandible or native mandibular defect of the patient.

Three methods are described for fixing the neo-mandible to the native mandible. These methods may also be used to fix the neo-mandible to the ramus. In the first, referred to herein as "standard fixation", a planar extension (referred to herein as a "phalange") of the first section may be fixated in bicortical fashion to the native mandible. However, this phalange may project against the soft tissue.

In the second method, referred to herein as "buried fixation", two or more round phalanges may extend from the first section towards the native mandible. A drill guide is placed over the native mandible and two drill holes are placed. Since these holes are critical to alignment, this drill guide may be fixated via screws to the native mandible, and the drill guide itself may have more plastic/metal on it than a normal drill guide. This drill guide prevents significant tilt off axis. The phalanges then may be inserted into the holes. In this manner of fixation, the phalange does not project against the soft tissue. An additional method of fixation across the first section to the native mandible, such as a countersunk compression screw over a K wire, would be placed to complete the stability of the construct.

In the third method, referred to herein as "countersunk fixation", a planar phalange having a plurality of through-holes may extend from the first section towards the native mandible. A cutting guide may be placed over the native mandible in the location where the phalange will be inset. This area of the native mandible is cored out, including the outer cortex. The phalange is advanced into the defect and mono cortical fixation is performed. That is, a screw is driven through each hole and all the way through the native mandible to engage the inner cortex. In this manner of fixation, the phalange does not project against the soft tissue. An additional method of fixation across the first section to the native mandible, such as a countersunk compression screw over a K wire, may be placed.

While several methods of fixation of the neo-mandible to the native mandible are described, it should be understood that other methods of fixation may be used. These methods may include methods that create soft tissue projection, and methods that do not create soft tissue projection.

In general, one aspect disclosed features a method comprising: providing a bone section; attaching a cutting guide to the bone section; cutting the bone section into multiple bone graft sections using the cutting guide; arranging the multiple bone graft sections in a neo-mandible position; attaching a temporary fixation plate to the multiple bone graft sections after arranging the multiple bone graft sections in the neo-mandible position; removing the cutting guide from the multiple bone graft sections after attaching the temporary fixation plate; attaching a final fixation plate to the multiple bone graft sections after removing the cutting guide; and removing the temporary fixation plate from the multiple bone graft sections after attaching the final fixation plate to create a neo-mandible assembly.

Embodiments of the method may include one or more of the following features. In some embodiments, the cutting guide is a hinged cutting guide comprising multiple cutting guide sections joined by at least one hinge; and arranging the multiple bone graft sections in a neo-mandible position comprises bending the sections about the at least one hinge. In some embodiments, attaching the temporary fixation plate to the multiple bone graft sections comprises: attaching the temporary fixation plate to cephalic surfaces of the multiple bone graft sections. In some embodiments, attaching the temporary fixation plate to the multiple bone graft sections comprises: attaching the temporary fixation plate to the multiple bone graft sections with multiple screws. In some embodiments, attaching the temporary fixation plate to the multiple bone graft sections comprises: attaching the temporary fixation plate to the multiple bone graft sections with multiple mono-cortical fixation screws. Some embodiments comprise implanting the neo-mandible assembly on a mandibular defect region of a patient. Some embodiments comprise placing dental implants in predetermined locations on the neo-mandible assembly.

In general, one aspect disclosed features a neo-mandible comprising: multiple bone graft sections arranged in a neo-mandible position; a cutting guide attached to the multiple bone graft sections; and a temporary fixation plate attached to the multiple bone graft sections.

Embodiments of the neo-mandible may include one or more of the following features. In some embodiments, the cutting guide is a hinged cutting guide comprising multiple cutting guide sections joined by at least one hinge. Some embodiments comprise an alignment guide; wherein the cutting guide comprises multiple cutting guide sections; and wherein the alignment guide is attached to the multiple cutting guide sections. In some embodiments, the temporary fixation plate is attached to cephalic surfaces of the multiple bone graft sections. In some embodiments, the temporary fixation plate is attached to the multiple bone graft sections with multiple screws. In some embodiments, the temporary fixation plate is attached to the multiple bone graft sections with multiple mono-cortical fixation screws.

In general, one aspect disclosed features a method comprising: providing at least one bone section; attaching a first cutting guide and a second cutting guide to the at least one bone section; cutting the at least one bone section into multiple bone graft sections using the first and second cutting guides; arranging the multiple bone graft sections into an upper neo-mandible position and a lower neo-mandible position using the first and second cutting guides; attaching an upper temporary fixation plate to the bone graft sections arranged in the upper neo-mandible position; attaching a lower temporary fixation plate to the bone graft sections arranged in the lower neo-mandible position; removing the first and second cutting guides from the multiple bone graft sections after attaching the upper temporary fixation plate and the lower temporary fixation plate; attaching a jaw plate between the bone graft sections arranged in the upper neo-mandible position and the bone graft sections arranged in the lower neo-mandible position; and removing the temporary fixation plates from the multiple bone graft sections after attaching the jaw plate to create a neo-mandible assembly.

Embodiments of the method may include one or more of the following features. Some embodiments comprise aligning the bone graft sections arranged in the upper neo-mandible position with the bone graft sections arranged in the lower neo-mandible position prior to attaching the jaw plate. In some embodiments, the first and second cutting guides are joined by a further hinge; and aligning the bone graft sections comprises rotating the first and second cutting guides about the further hinge. In some embodiments, the first cutting guide is a hinged cutting guide comprising multiple cutting guide sections joined by at least one hinge;

and arranging the multiple bone graft sections in at least one of the upper neo-mandible position comprises bending the multiple cutting guide sections about the at least one hinge. In some embodiments, the first cutting guide comprises multiple cutting guide sections; and the method further comprises attaching an alignment guide to the multiple cutting guide sections of the first cutting guide. In some embodiments, attaching the upper temporary fixation plate to the bone graft sections arranged in the upper neo-mandible position comprises attaching the upper temporary fixation plate to cephalic surfaces of the bone graft sections arranged in the upper neo-mandible position; and attaching the lower temporary fixation plate to the bone graft sections arranged in the lower neo-mandible position comprises attaching the lower temporary fixation plate to cephalic surfaces of the bone graft sections arranged in the lower neo-mandible position. In some embodiments, attaching the upper and lower temporary fixation plates comprises: attaching the upper and lower temporary fixation plates with multiple screws. In some embodiments, the multiple screws are mono-cortical fixation screws. Some embodiments comprise implanting the neo-mandible assembly on a mandibular defect region of a patient. Some embodiments comprise placing dental implants in predetermined locations on the neo-mandible assembly.

These and other embodiments are described in further detail in the following description related to the appended drawing figures.

BRIEF DESCRIPTION OF THE DRAWINGS

Specific embodiments of the disclosed device, surgical systems, or methods will now be described with reference to the drawings. Nothing in this detailed description is intended to imply that any particular component, feature, or step is essential to the invention.

FIGS. 14A and 14B illustrate aspects of a surgical system, in accordance with some embodiments.

FIGS. 24A, 24B, 24C, and 24D illustrate aspects of preoperative planning cutting planes, in accordance with some embodiments.

FIG. 43A illustrates the native mandible and the first section according to some embodiments of the disclosed technologies.

FIG. 43B illustrates the native mandible with a drill guide attached according to some embodiments of the disclosed technologies.

FIG. 43C illustrates the native mandible and the first section after drilling holes in the native mandible according to some embodiments of the disclosed technologies.

FIG. 43D illustrates the native mandible after being joined with the first section according to some embodiments of the disclosed technologies.

FIG. 43E illustrates the joined native mandible and first section with a compression screw driven over a K wire through the first lower bone graft section and into the native mandible according to some embodiments of the disclosed technologies.

FIG. 44 illustrates a neo-mandible according to some embodiments of the disclosed technologies.

FIG. 45 is a left-side view of the neo-mandible of FIG. 44 according to some embodiments of the disclosed technologies.

FIG. 46 illustrates the native mandible with a drilling guide installed according to some embodiments of the disclosed technologies.

FIG. 47 illustrates the native mandible after drilling holes in the native mandible according to some embodiments of the disclosed technologies.

FIG. 48 illustrates the native mandible with the neo-mandible installed in the native mandible according to some embodiments of the disclosed technologies.

FIG. 50A illustrates the native mandible and the first section according to some embodiments of the disclosed technologies.

FIG. 50B illustrates the native mandible with a cutting guide attached according to some embodiments of the disclosed technologies.

FIG. 50C illustrates the native mandible and the first section after cutting a channel in the native mandible according to some embodiments of the disclosed technologies.

FIG. 50D illustrates the native mandible after being joined with the first section according to some embodiments of the disclosed technologies.

FIG. 50E illustrates one possible method of additional fixation, namely a K wire inserted through the first lower bone graft section and into the native mandible according to some embodiments of the disclosed technologies.

FIG. 51 illustrates a neo-mandible according to some embodiments of the disclosed technologies.

FIG. 52 illustrates the native mandible with a cutting guide installed according to some embodiments of the disclosed technologies.

FIG. 53 illustrates the native mandible after cutting a channel in the native mandible according to some embodiments of the disclosed technologies.

FIG. 54 illustrates the native mandible with the neo-mandible installed in the native mandible according to some embodiments of the disclosed technologies.

FIG. 56 illustrates a section of native bone.

FIG. 57 illustrates the native fibula section of FIG. 56 with bone graft sections marked.

FIG. 58 illustrates the bone graft sections of FIG. 57 after being cut from the native fibula section of FIG. 56, according to some embodiments of the disclosed technology.

FIG. 59 illustrates the bone graft sections arranged in a neo-mandible position, as well as a temporary fixation plate configured to hold the bone graft sections in the neo-mandible position, according to some embodiments of the disclosed technology.

FIG. 60 illustrates the temporary fixation plate being attached to the bone graft sections using screws, according to some embodiments of the disclosed technology.

FIG. 61 illustrates the bone graft sections with the temporary fixation plate attached, according to some embodiments of the disclosed technology.

FIG. 62 illustrates the bone graft sections with the temporary fixation plate attached using screws, and with the final fixation plate attached, for example using screws, according to some embodiments of the disclosed technology.

FIG. 63 illustrates removal of the temporary fixation plate and screws 6000 from bone graft sections, according to some embodiments of the disclosed technology.

FIGS. 65-69 illustrate a double-barrel mandibular reconstruction technique utilizing temporary fixation plates according to some embodiments of the disclosed technologies.

FIG. 65 illustrates hinged cutting guides bent to arrange the bone graft sections in an upper neo-mandible position and a lower neo-mandible position, according to some embodiments of the disclosed technology.

FIG. 66 illustrates temporary fixation plates being attached to the bone graft sections, according to some embodiments of the disclosed technology.

FIG. 67 illustrates bending the hinged cutting guide to align the bone graft sections arranged in the upper neo-mandible position with the bone graft sections arranged in the lower neo-mandible position, according to some embodiments of the disclosed technology.

FIG. 68 illustrates attaching a jaw plate between the bone graft sections arranged in the upper neo-mandible position and the bone graft sections arranged in the lower neo-mandible position to create a double-barrel neo-mandible, according to some embodiments of the disclosed technology.

FIG. 69 illustrates the double-barrel neo-mandible of FIG. 68 attached to a native mandible, according to some embodiments of the disclosed technology.

DETAILED DESCRIPTION OF THE INVENTION

Figure 1:
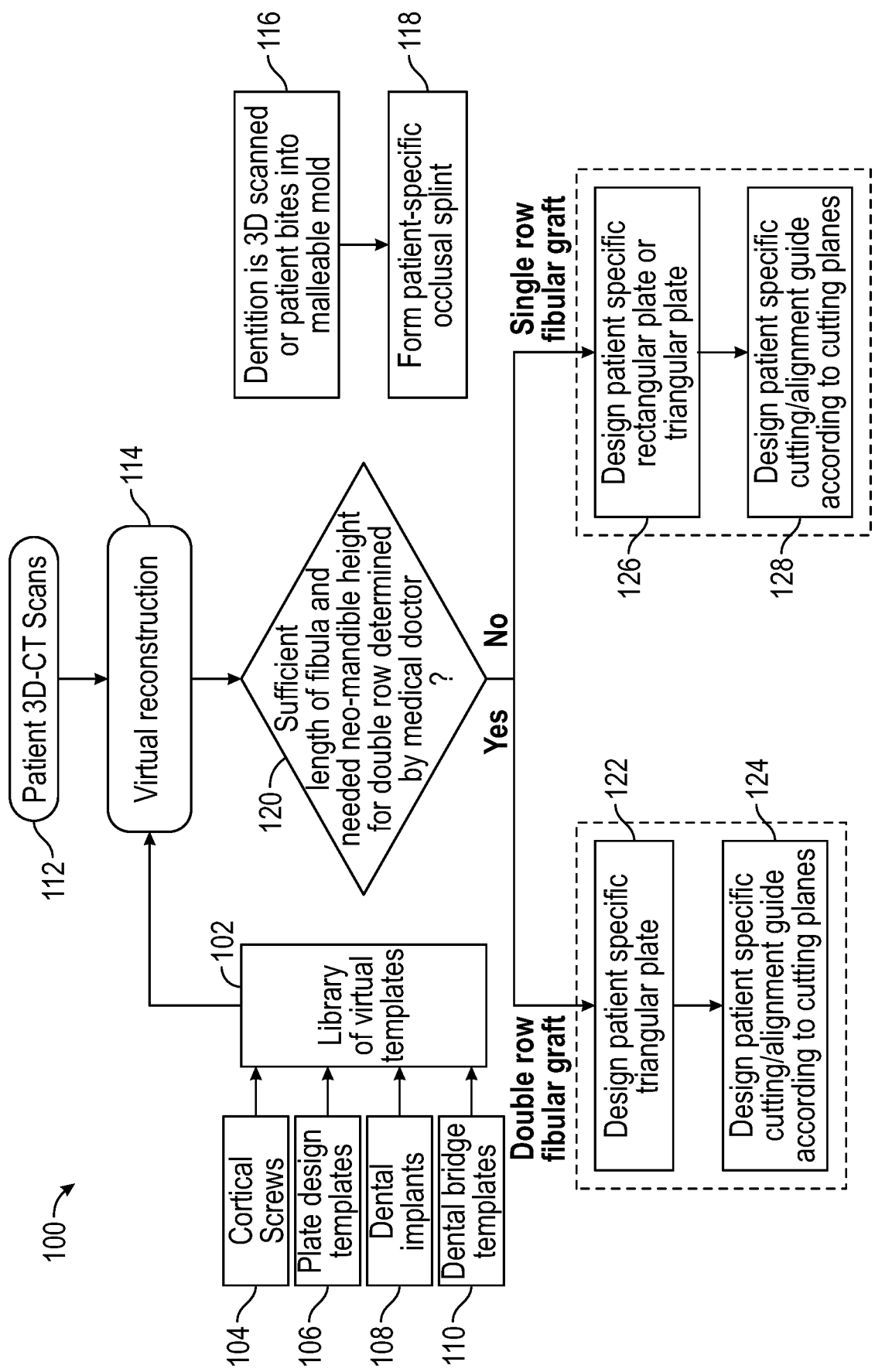
FIG. 1 depicts aspects of a preoperative planning method for designing a patient specific cutting/alignment guide, in accordance with some embodiments.

Currently available mandibular reconstructions systems and techniques can be complicated and involve long recovery times. Often, virtual surgical planning and guided resection and reconstruction of mandibular defects involves complicated 3D virtual surgical planning. However, the accuracy of a virtually planned surgery depends on the execution of the surgery. Embodiments of the present invention encompass systems and methods for cutting custom and accurate bone grafts, which are particularly well suited for use with variable patient mandible geometries, and for accommodating various locations of defects (e.g. tumors) for mandibular reconstruction. Exemplary embodiments disclosed herein provide simple methods of cutting and forming bone grafts into desired shapes, which advantageously provide the surgeon with improved procedural control resulting in less operating time and better reproduction of the patient's mandibular contour.

With existing surgical techniques, dental reconstruction is often delayed 3-6 months post mandibular reconstruction surgery. Embodiments of the present invention encompass systems and methods that enable the implementation of concurrently installed dental implants during surgery which can greatly reduce the overall recovery time and also reduce the interim time that the patient would be without teeth.

Currently available mandibular reconstruction systems often involve plates and screws that protrude into the soft tissue around them and that can cause irritation. Embodiments of the present invention encompass systems and methods for nesting a triangular plate and screws between fibular grafts which can reduce irritation while also utilizing the negative space between two rows of fibular graft. Additionally, a triangular plate has greater structural rigidity in multiple axes of rotation than that of a thin anterior rectangular plate.

Existing mandibular reconstructions systems include devices that are not patient specific and are limited to mandibular osteotomies located around the symphysis region. Some existing systems involve multiple moving parts and require a multitude of steps in order to achieve a surgical outcome. Some existing systems involve plate designs that do not work with stacked rows of fibular grafts, nor do they involve recessed screws between bone. Embodiments of the present invention provide unique solutions to many of these drawbacks.

Mandibular reconstruction systems as disclosed herein can include a cutting/alignment guide having multiple moving parts. For example, a cutting/alignment guide assembly can include three primary moving parts, namely left, middle, and right sections. Each section can be fixed to a fibula using one or more temporary fixation screws. On either side of the cutting guide sections there may be either U-shaped or flat cutting guide surfaces. Between each cutting guide section there may be a hinge located at the intersection of cutting planes. Hinges can be held together with press-fit dowel pins. Each hinge can also feature angular limiting surfaces to orient the cutting/alignment guide in the straight or bent position. In some cases, a triangular cross-sectional plate can feature recessed holes for the screws, for example two screws for each section of fibula.

Turning now to the drawings, FIG. 1 depicts aspects of a preoperative planning method 100 for designing a patient specific cutting/alignment guide according to some embodiments of the disclosed technologies. As described here, a triangular plate can be used for a double row fibular graft, and a rectangular plate can be used for a single row fibular graft. In some cases, a rectangular plate can be used in the mid-mandibular position with the tension band for dental implantation. In some cases, a triangular plate can be used for a single row graft.

Referring now to FIG. 1, the method 100 may include obtaining a library of virtual templates, at 102. The library 102 may include cortical screws, at 104, plate design templates, at 106, dental implants, at 108, dental bridge templates, at 110, and similar templates. The method 100 may include performing patient 3D-CT scans and/or similar scans, at 112. The method 100 may include generating a virtual reconstruction based on the scans and virtual templates, at 114.

The method 100 may include performing a 3D scan or patient bites into a malleable mold, at 116. The method 100 may include forming a patient-specific occlusal scans and/or molds, at 118.

The method 100 may include determining whether there is a sufficient length of fibula and needed neo-mandible height for a double row fibular graft, at 120. This determination may be made by a medical doctor. If a double row fibular graft is needed, the method may include designing a patient specific triangular plate, at 122, and designing a patient specific cutting and alignment guide according to determined cutting planes, at 124. If a double row fibular graft is not needed, the method 100 may include designing a patient specific rectangular plate or triangular plate, at 126, and designing a patient specific cutting and alignment guide according to determined cutting planes, at 128.

Figure 2:
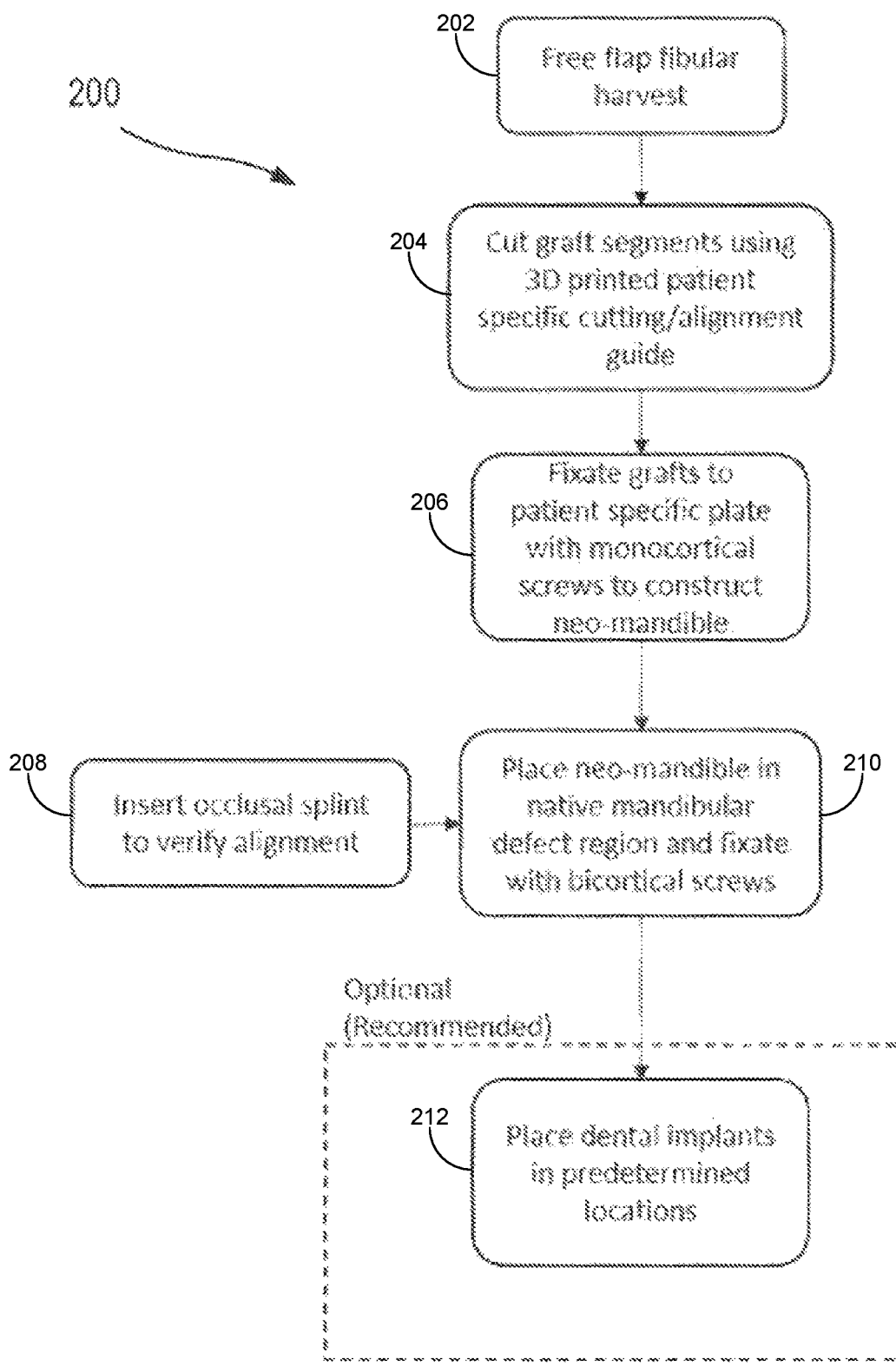
FIG. 2 illustrates aspects of a surgical method for mandibular reconstruction, in accordance with some embodiments.

FIG. 2 depicts aspects of a surgical method 200 for mandibular reconstruction according to some embodiments of the disclosed technologies. According to some embodiments, a microsurgical, plastic surgical, otolaryngological, maxillofacial, orthopedic, dental, or other surgical method may include sectioning a free flap fibula and removing it from the leg, at 202.

Next, the method 200 may include cutting graft segments using a patient specific cutting and alignment guide, at 204. In some embodiments, the guide may be 3D printed. The cutting/alignment guide can be located and secured to the fibula using one or more temporary fixations screws (e.g. one or more for each section), at 206. Exemplary fixation screw configurations will provide torsional stability. Thereafter, cuts can be made along the cutting guide surfaces carefully as to not cut the peroneal vessels. Once excess bone is removed, the cutting/alignment guide can be bent to form the neo-mandible. Next, a triangular plate can be installed in the recess superior to the cutting guide and monocortical screws can be driven into the fibula graft sections, securing them to the plate. Then the neo-mandible can be placed in the native mandible or at the native mandibular defect region and an occlusal splint can be inserted to verify alignment, at 208, and the plate can be secured to the native mandible using bicortical screws, at 210. Next, dental implants can be installed in predetermined locations that do not interfere with the cortical screws, while also angled correctly for proper occlusion with dental bridge, at 212. According to some embodiments, a microsurgeon can choose to do the microsurgical reconstruction and then do the osteotomies and cuts. In some embodiments, a microsurgeon can choose to do the bony work and then do the microsurgical reconstruction.

Figure 3:
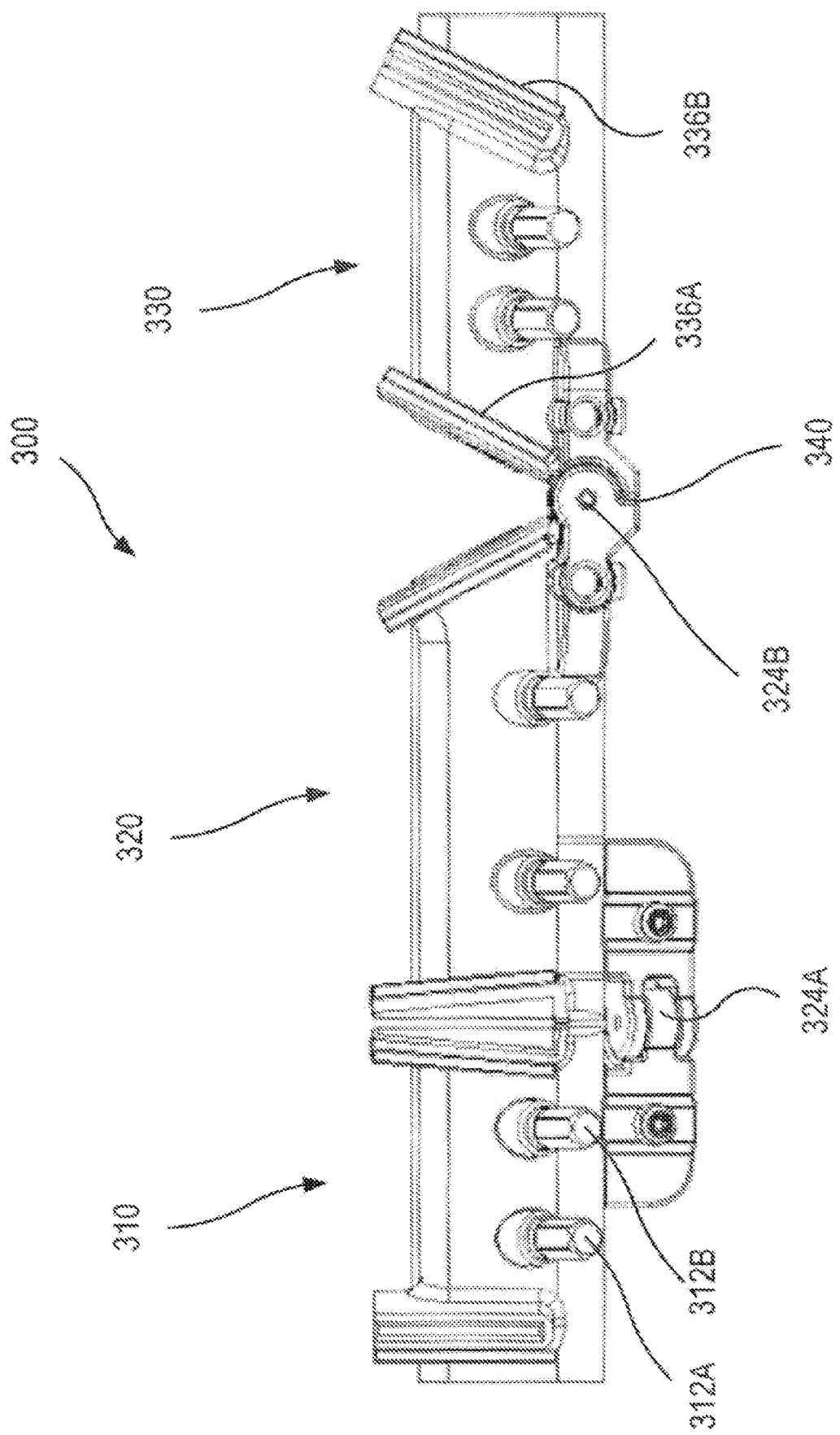
FIG. 3 depicts aspects of a cutting/alignment guide assembly, in accordance with some embodiments.

FIG. 3 depicts aspects of a cutting/alignment guide assembly 300 that includes three primary moving parts, namely a left cutting guide or section 310, a middle cutting guide or section 320, and a right cutting guide or section 330. The assembly 300 also includes temporary fixation screws 312A, 312B, dowel pin hinges 324A, 324B, magnets 336A, 336B. Further, the assembly 300 includes a hinge position blocker 340. Hence, a cutting/alignment guide assembly 300 can include three primary moving parts: left 310, middle 320, and right sections 330. Each section can be fixed to a fibula using one or more temporary fixation screws. In some cases, more than two temporary fixation screws may be used. On either side of the cutting guide sections there can be either U-shaped or flat cutting guide surfaces. Between each cutting guide section a hinge can be located at the intersection of cutting planes. Hinges can be held together with press-fit dowel pins. Each hinge can also feature angular limiting surfaces to orient the cutting/alignment guide in the straight or bent position. The patient specific cutting guide and alignment fixture 300 can be used to precisely cut fibular bone grafts at predetermined locations and then conform grafts into final orientation to construct a neo-mandible.

Figure 4:
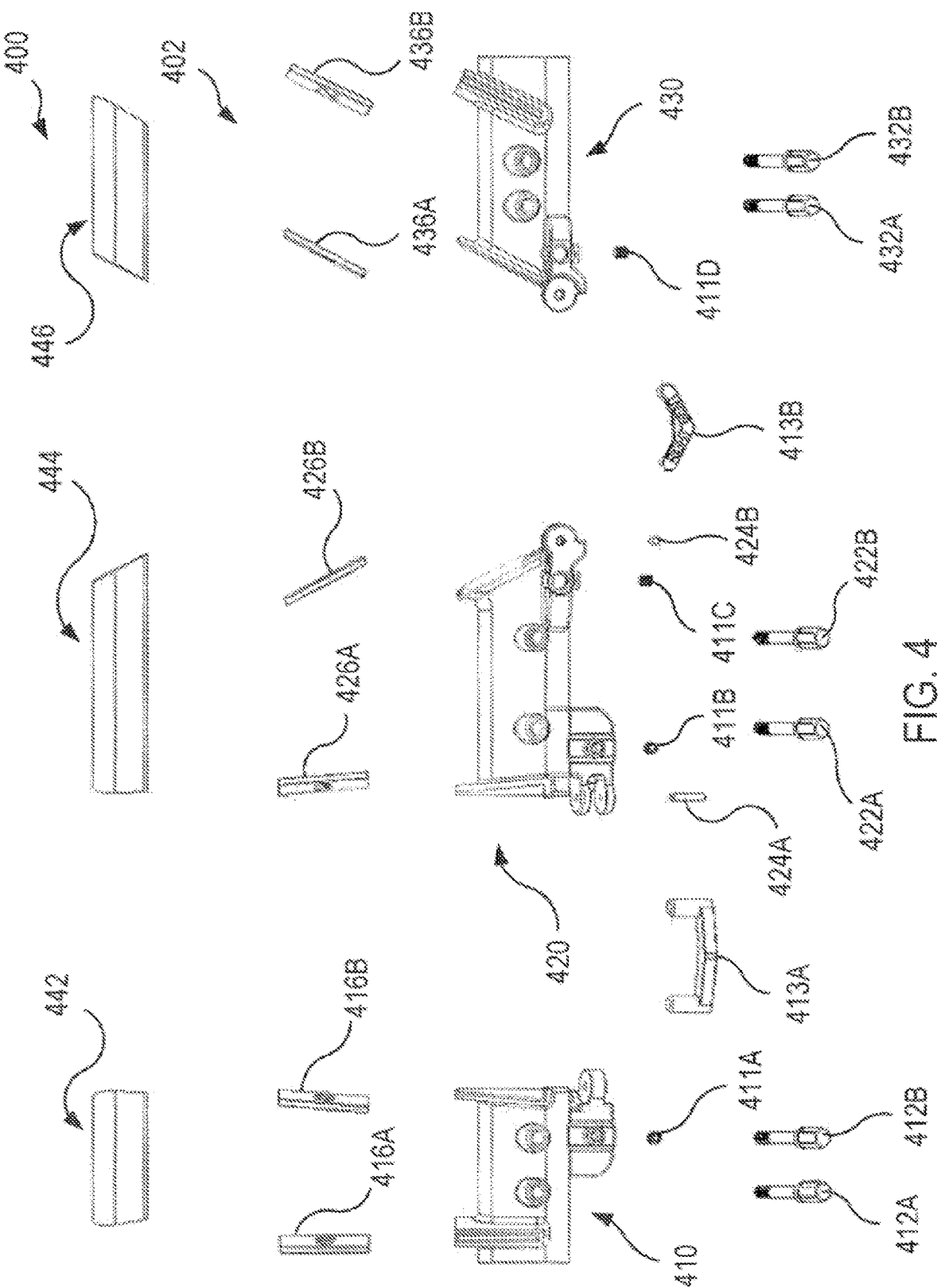
FIG. 4 provides an exploded view of aspects of a surgical system or neo-mandible, in accordance with some embodiments.

FIG. 4 provides an exploded view of aspects of an exemplary surgical system 400 according to embodiments of the present invention. As shown here, system 400 includes a cutting/alignment guide assembly 402 that includes multiple parts, namely a left cutting guide or section 410, a middle cutting guide or section 420, and a right cutting guide or section 430. The assembly 402 also includes temporary fixation screws 412A, 412B, 422A, 422B, 432A, 432B, dowel pin hinges 424A, 424B, and magnets 416A, 416B, 426A, 426B, 436A, 436B. In some embodiments, magnets can be optional. As shown in FIG. 4, system 400 also includes a first fibula graft 442, a second fibula graft 444, and a third fibula graft 446, as well as set screws 411A, 411B, 411C, 411D, a left angle locker 413A, and a right angle locker 413B.

According to some embodiments, magnets on one side of each cutting guide surface can operate to maintain a constant bias to one side and to reduce blade chatter. In some embodiments, systems may include a two sectioned cutting/alignment guide. In some embodiments, systems may include a four or more sectioned cutting/alignment guide.

Cutting guides may be 3D printed out of biocompatible surgical guide resin, or may be machined out of Radel® polyphenylsulfone (PPSU), stainless steel, or any other biocompatible material. A triangular plate may be 3D printed out of biocompatible titanium alloys such as Ti 6Al-4V, or may be machined out of stainless steel, titanium or any other biocompatible alloy.

Embodiments of the present invention encompass systems and methods that involve a cutting/alignment guide that is configured to cut bone grafts ranging in size from 20 to 100 millimeters in length. In some cases, a cutting/alignment guide can be configured to cut bone grafts ranging in size from 30 to 50 millimeters in length. In some instances, the cutting guides can be configured to accommodate blades 25 to 45 millimeters in cutting edge length and blade thicknesses of up to 0.5 millimeters thick. In some cases, systems or devices can incorporate flexural hinges instead of pinned hinges. In some cases, systems or devices can incorporate one long patient specific anterior plate. In some cases, systems or devices can incorporate one or more mini-plates to secure a single row of fibular grafts instead of a triangular plate. In some cases, systems or devices can incorporate one or more mini-plates in a double barrel configuration.

Advantageously, embodiments disclosed herein provide the ability to be used for both cutting and forming bone graft for any section of the mandible and the ability to conform to varying patient mandible sizes and shapes. What is more, exemplary embodiments, encompass techniques that involve nesting a triangular plate and screws between fibular grafts, which can reduce irritation while also utilizing the negative space between two rows of fibular graft. Additionally, a triangular plate has greater structural rigidity in multiple axes of rotation than that of a thin anterior rectangular plate. Hence, systems and methods disclosed herein can be preferred over existing plate and screw devices that protrude into the soft tissue around them and that cause irritation. Yet further still, exemplary systems and methods disclosed herein enable the use of a reduced number of parts and steps involved with cutting and forming fibular grafts into final position. The simplicity exemplary devices enables easy operation and reduces the likelihood of surgeon misplacing or mixing up parts.

Figure 5:
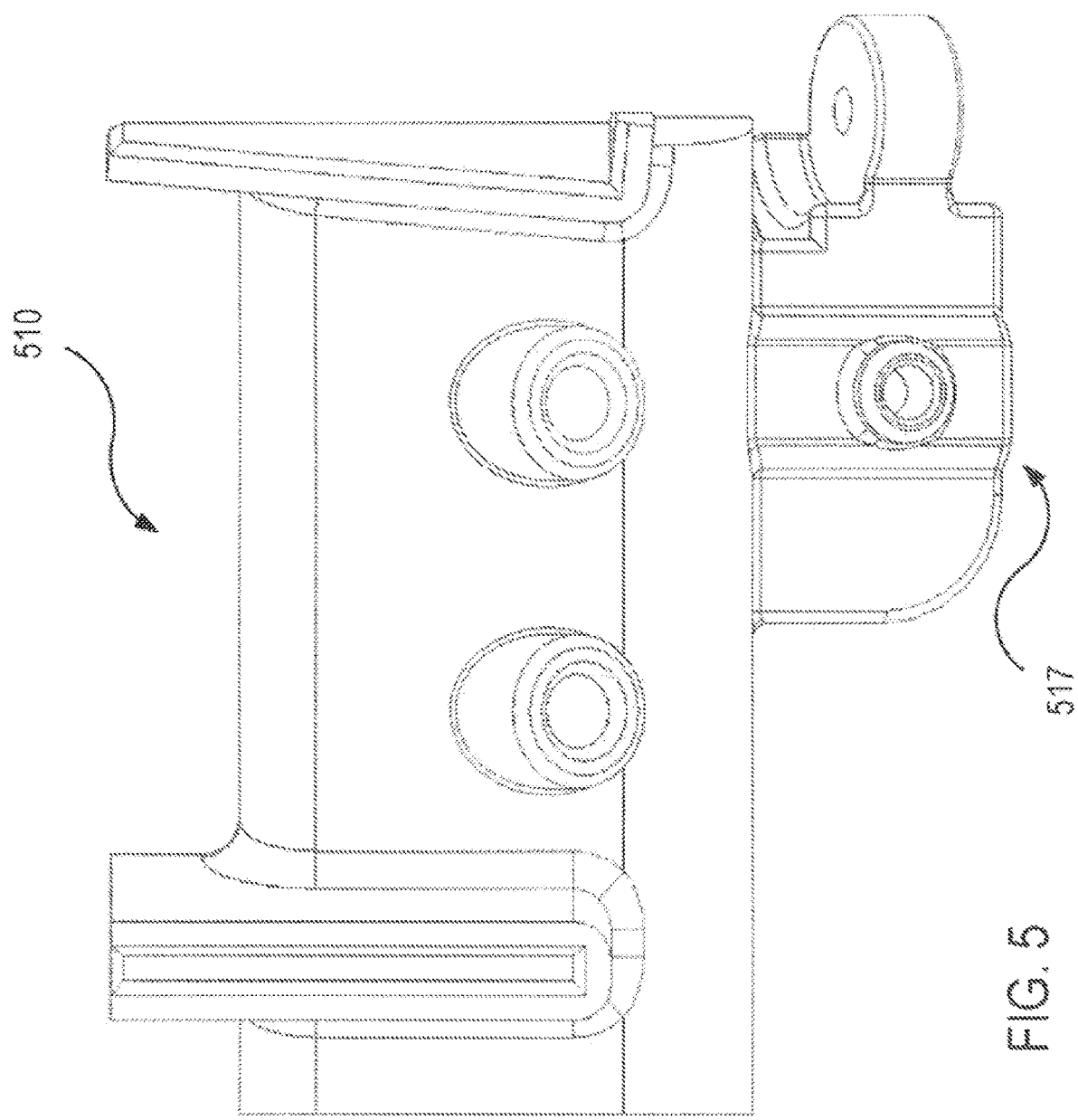
FIG. 5 illustrates aspects of a cutting guide, in accordance with some embodiments.
Figure 6:
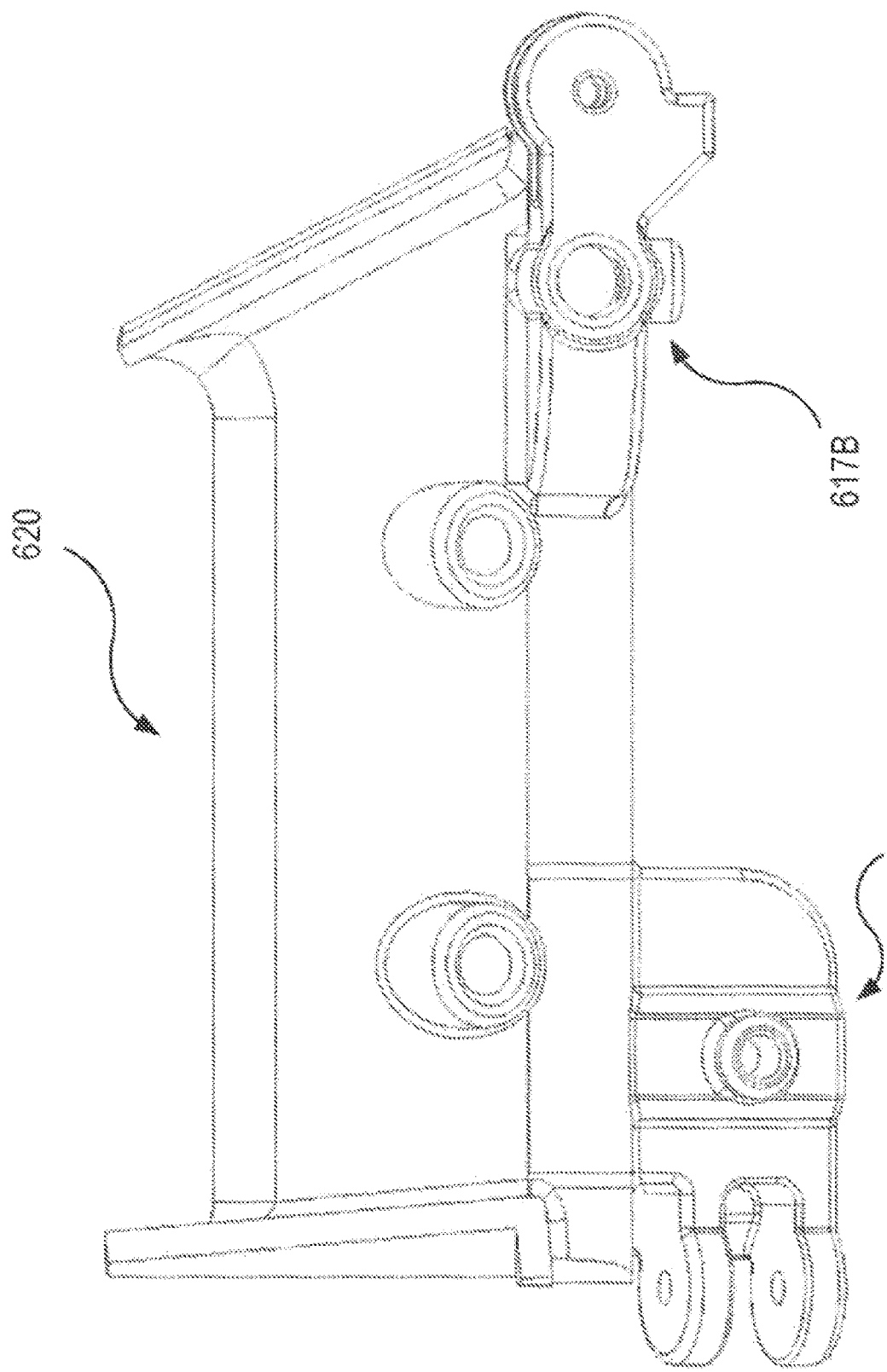
FIG. 6 illustrates aspects of a cutting guide, in accordance with some embodiments.
Figure 7:
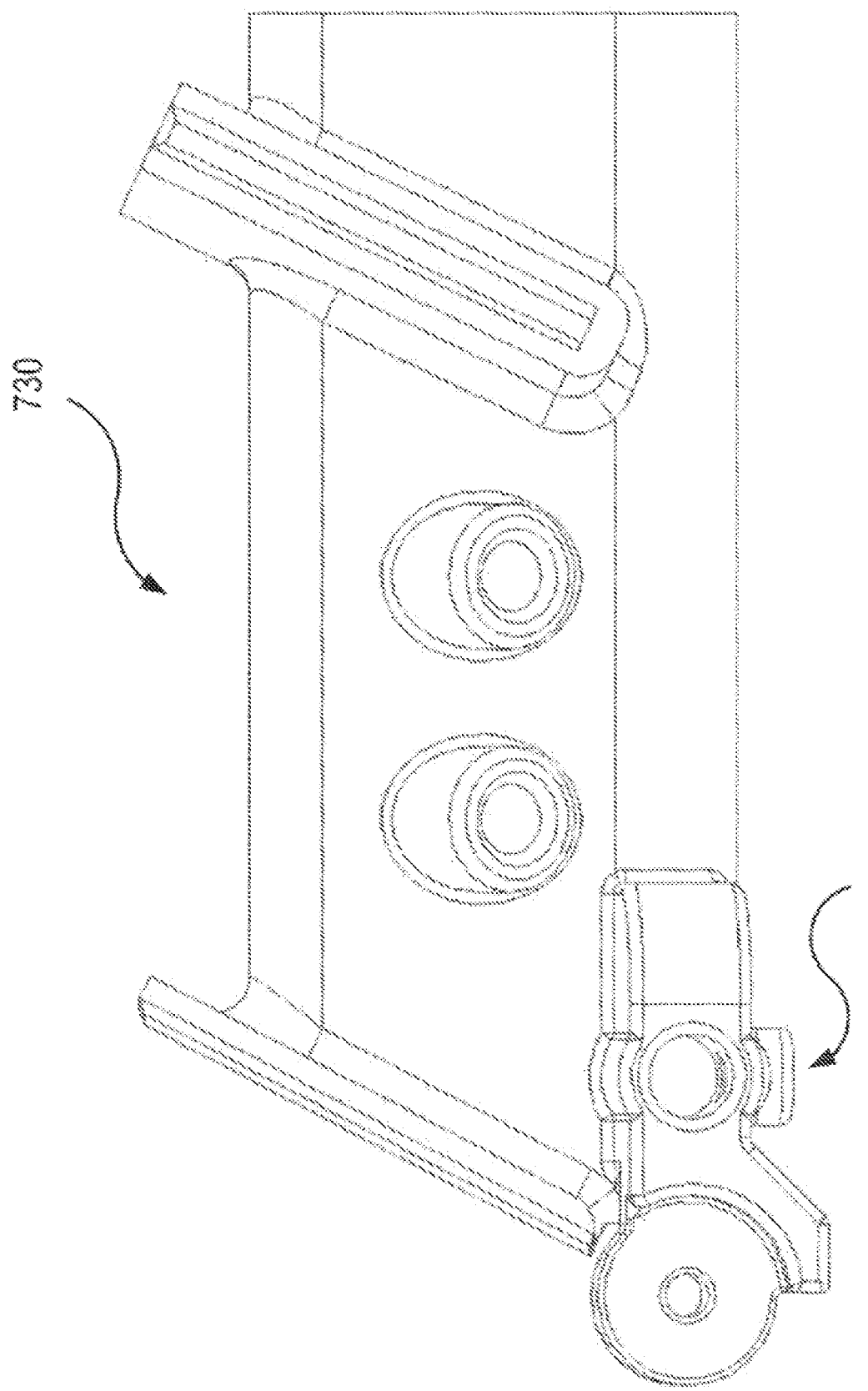
FIG. 7 illustrates aspects of a cutting guide, in accordance with some embodiments.
Figure 8A:
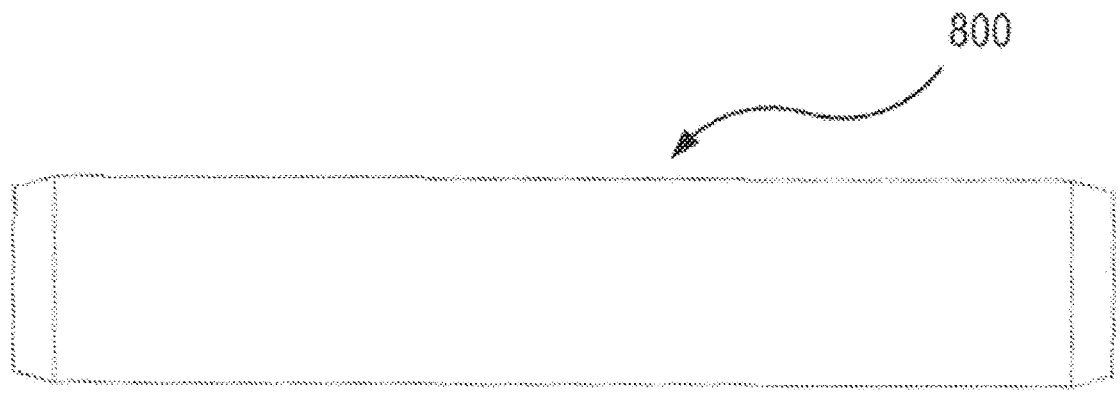
FIG. 8A illustrates aspects of a pin, in accordance with some embodiments.
Figure 8B:
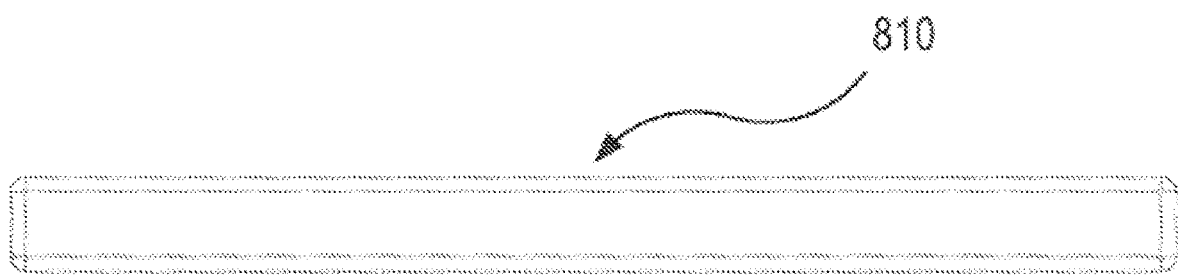
FIGS. 8B and 8C illustrate aspects of a magnet, in accordance with some embodiments.
Figure 8C:
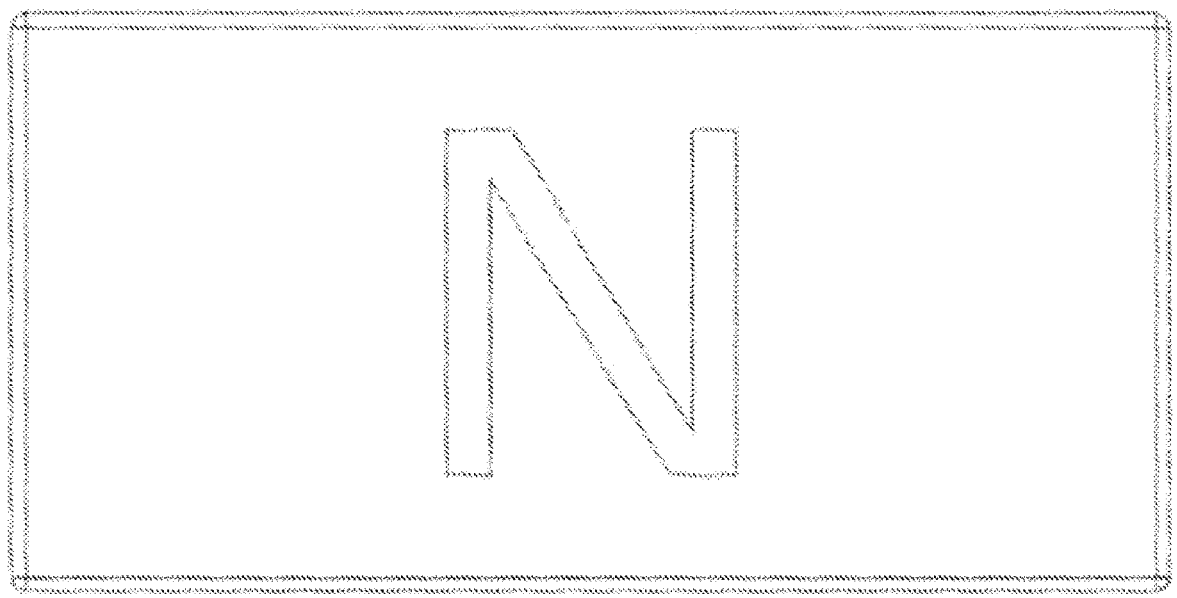

FIG. 5 depicts aspects of a left cutting guide 510, which includes an angle lock holder 517. FIG. 6 depicts aspects of a middle cutting guide 620, which includes a first angle lock holder 617A and a second angle lock holder 617B. FIG. 7 depicts aspects of a right cutting guide 730, which includes an angle lock holder 717. FIG. 8A depicts aspects of a pin 800, such as a M2×8 dowel pin. FIGS. 8B and 8C depict aspects of a magnet 810 according to embodiments of the present invention. In some cases, a magnet 810 can be a 10×20×1.7 mm neodymium magnet.

Figure 9A:
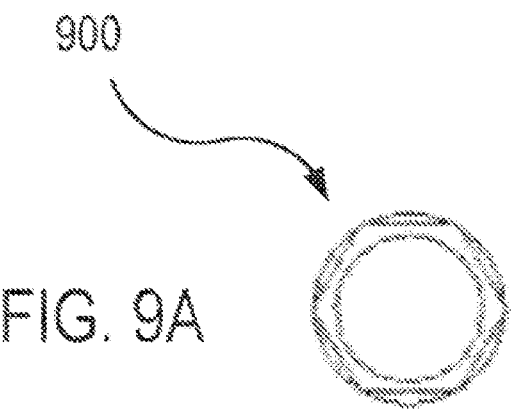
FIGS. 9A and 9B illustrate aspects of a temporary fixation screw, in accordance with some embodiments.
Figure 9B:
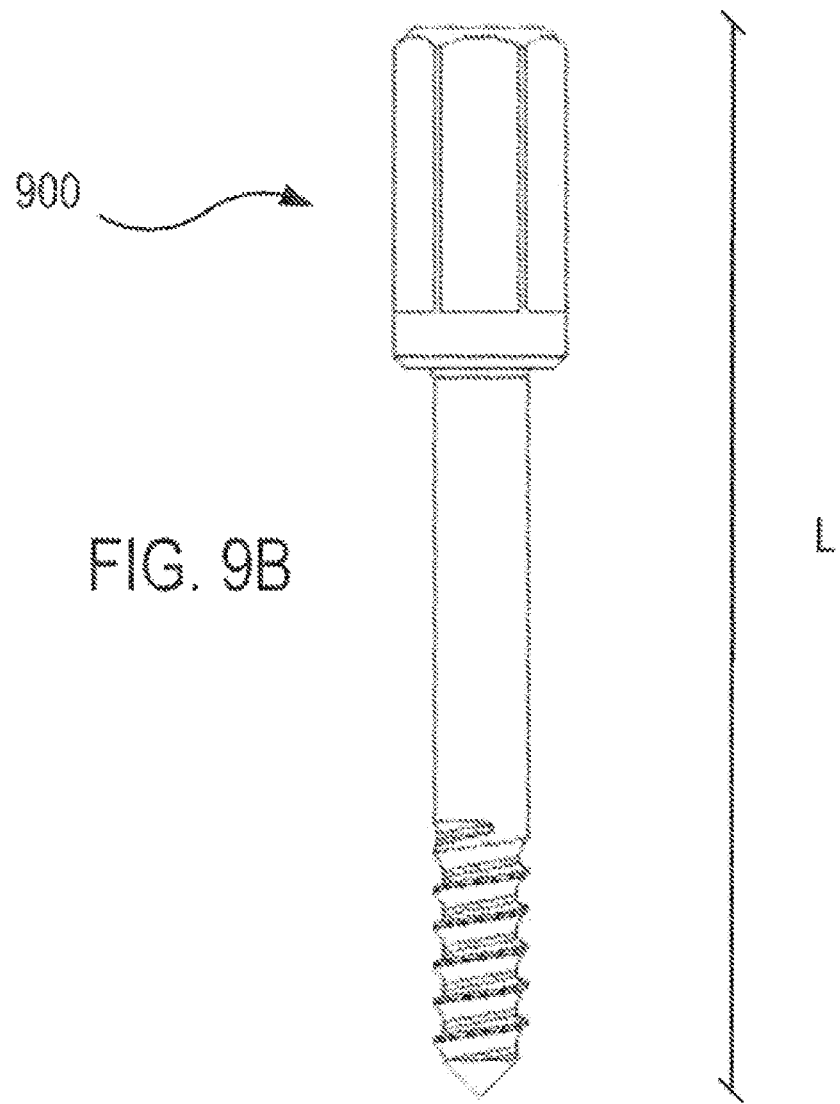

FIGS. 9A and 9B depict aspects of a temporary fixation screw 900 according to embodiments of the present invention. In some cases, a fixation screw 900 can be a 4 mm hex driven screw. In some cases, a fixation screw 900 can have a length L of about 20 mm. Embodiments of the present invention encompass alternative configurations as well.

Figure 10:
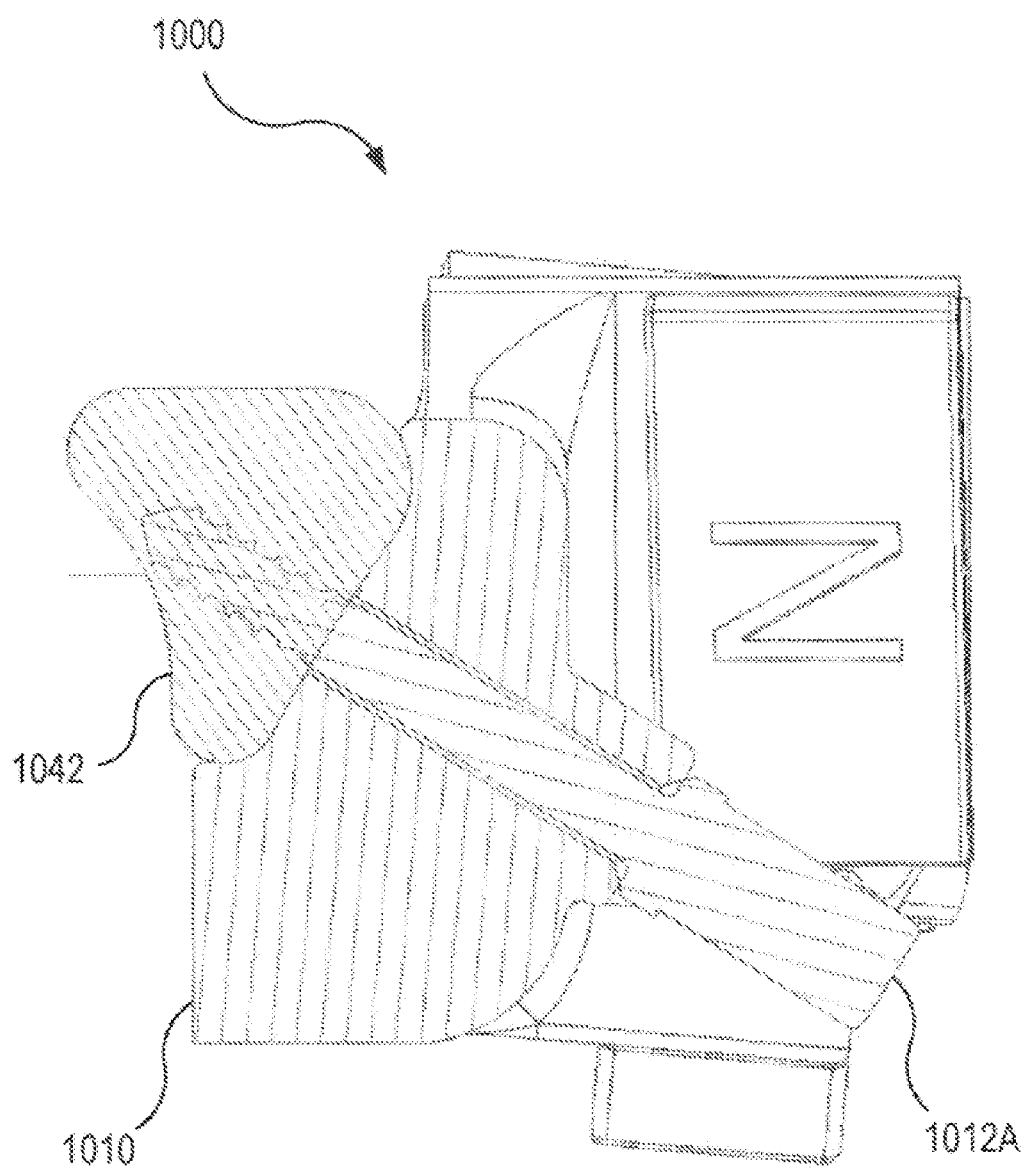
FIG. 10 illustrates aspects of a surgical system, in accordance with some embodiments.

FIG. 10 provides a cross-section view of aspects of a surgical system 1000, according to embodiments of the present invention. As shown here, surgical system 1000 includes a fibular graft segment 1042, a cutting guide section 1010, and a temporary fixation screw 1012A.

Figure 11A:
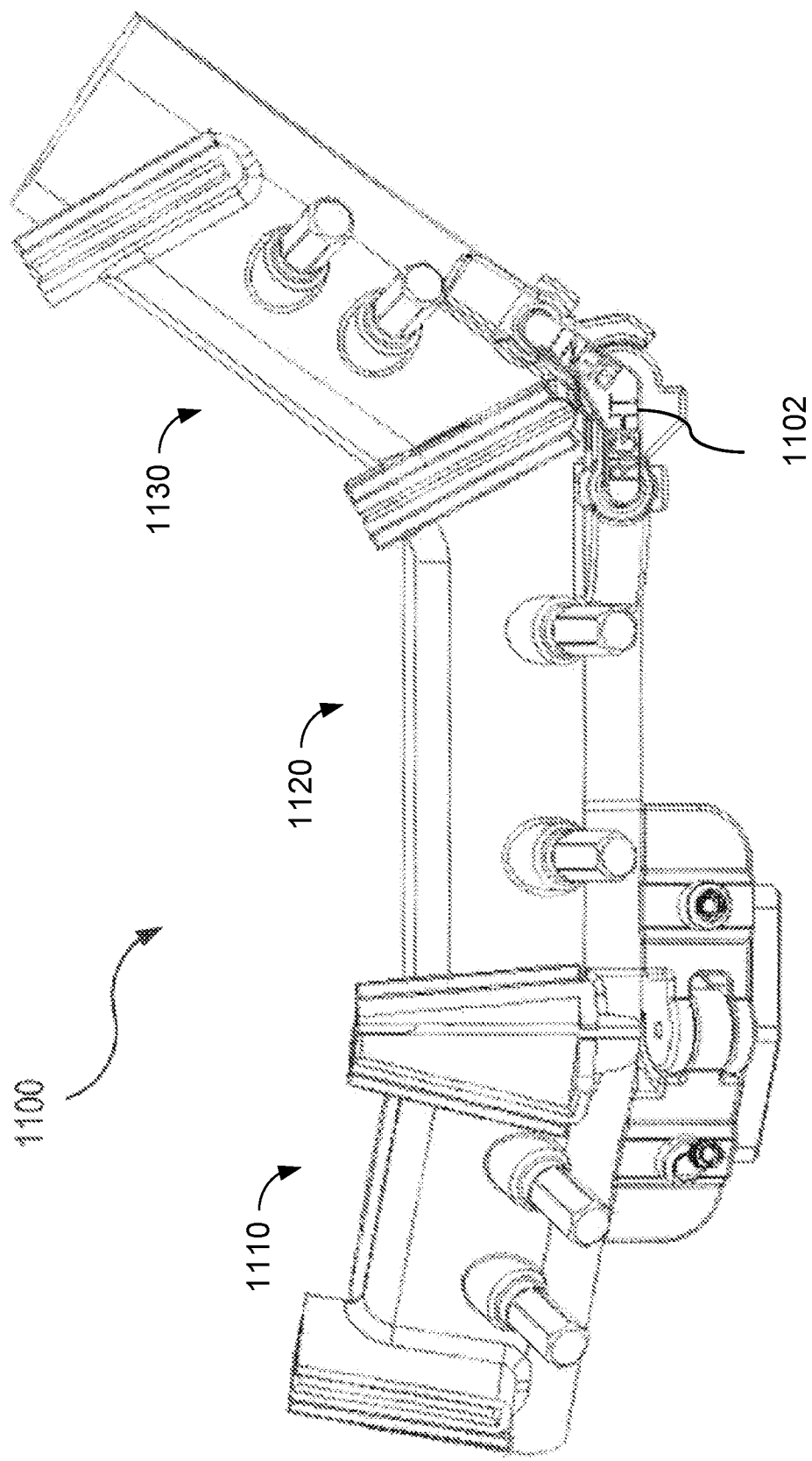
FIGS. 11A and 11B illustrate aspects of a surgical system, in accordance with some embodiments.
Figure 11B:
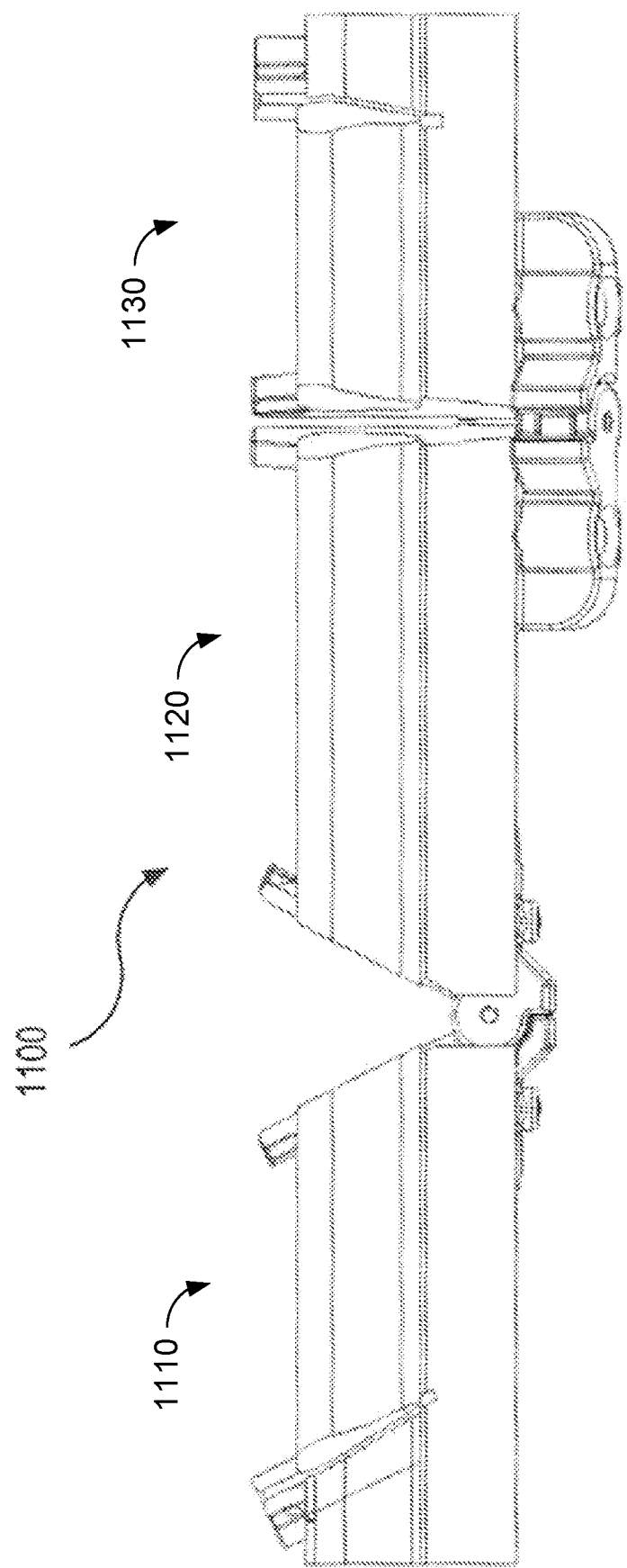

FIG. 11A depicts a surgical system 1100 in a bent configuration or orientation. Referring to FIG. 11A, the surgical system 1100 includes a left section 1110, a middle section 1120, and a right section 1130. Also shown in FIG. 11A is a right hinge angle lock 1102 installed on the hinge joining the middle section 1120 and the right section 1130. The right hinge angle lock 1102 is depicted in more detail in FIGS. 35A,B. FIG. 11B depicts the surgical system 1100 of FIG. 11A in a straight configuration or orientation.

Figure 12A:
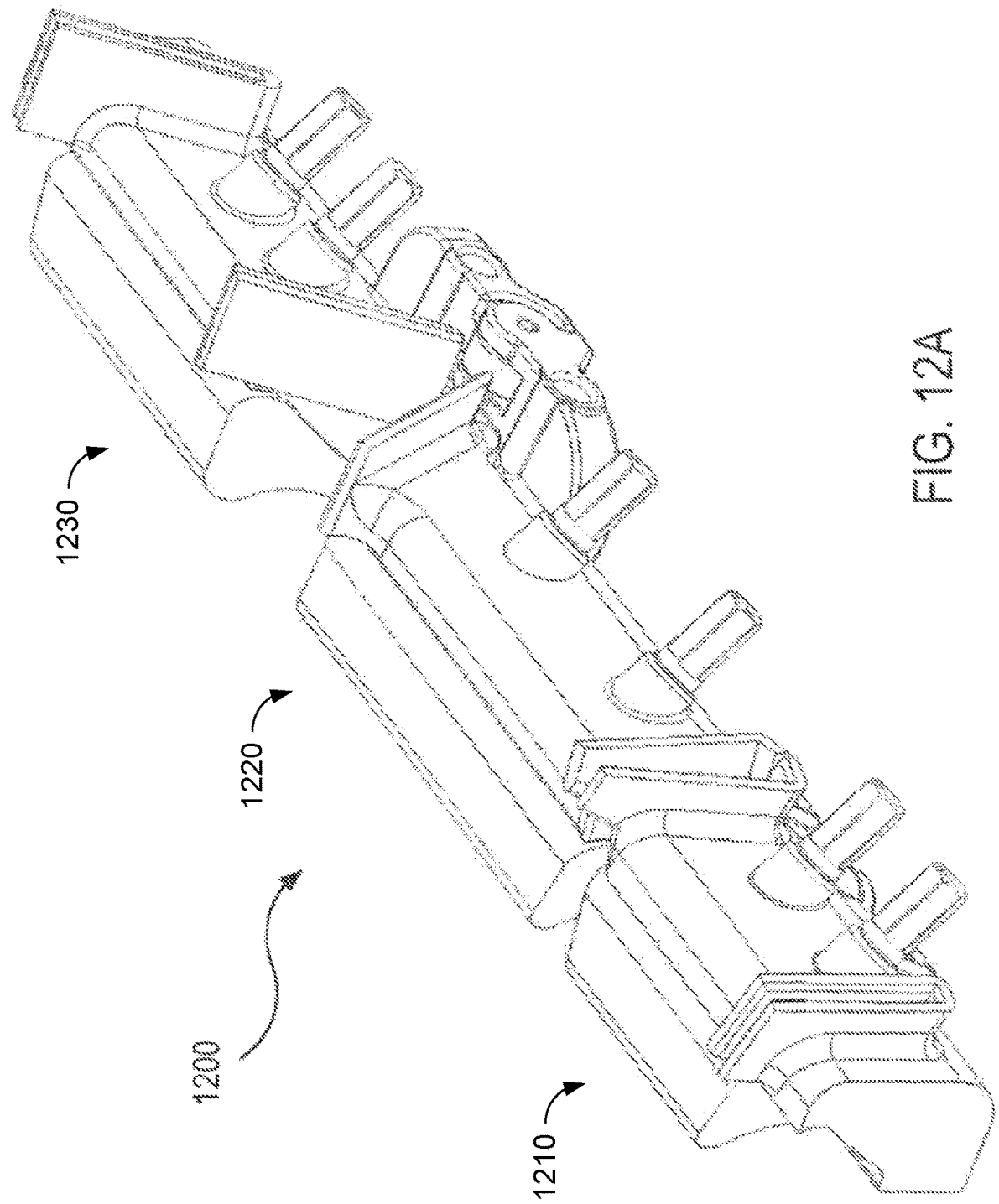
FIGS. 12A and 12B illustrate aspects of a surgical system, in accordance with some embodiments.
Figure 12B:
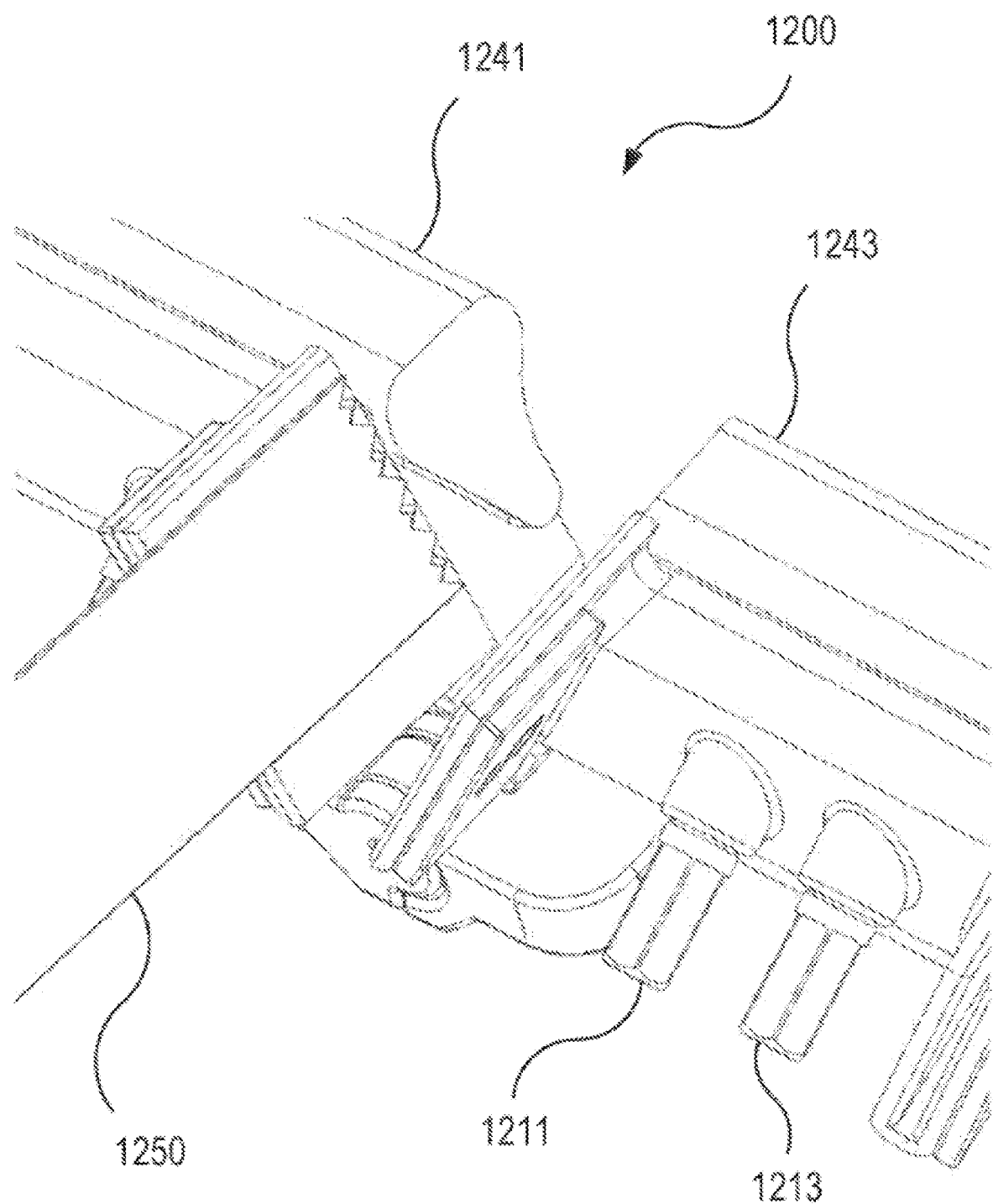

FIG. 12A provides an isometric view of a surgical system 1200, according to embodiments of the present invention. Referring to FIG. 12A, the surgical system 1200 includes a left section 1210, a middle section 1220, and a right section 1230. The sections 1210, 1220, and 1230 may be joined by hinges or other devices as depicted, or not joined at all. FIG. 12B illustrates aspects of a surgical system 1200 according to embodiments, of the present invention. As shown here, surgical system 1200 includes fibular grafts 1241, 1243, a sagittal saw blade 1250, and temporary fixation screws 1211, 1213. In some embodiments, a cutting/alignment guide can be designed to cut bone grafts ranging in size from 20 to 100 millimeters in length, though sizes ranging from 30 to 50 millimeters may be more common. Exemplary cutting guides can accommodate blades 25 to 45 millimeters in cutting edge length and blade thicknesses of up to 0.5 millimeters thick.

Figure 13A:
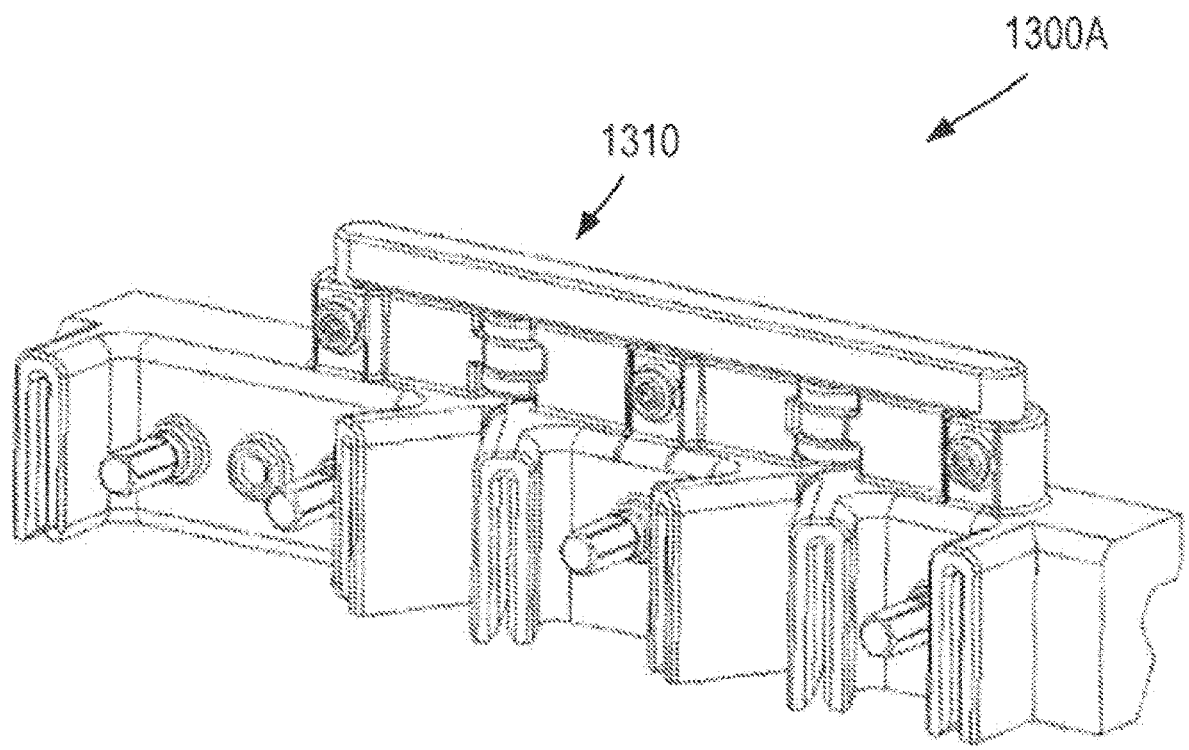
FIGS. 13A and 13B illustrate aspects of a cutting guide assembly, in accordance with some embodiments.
Figure 13B:
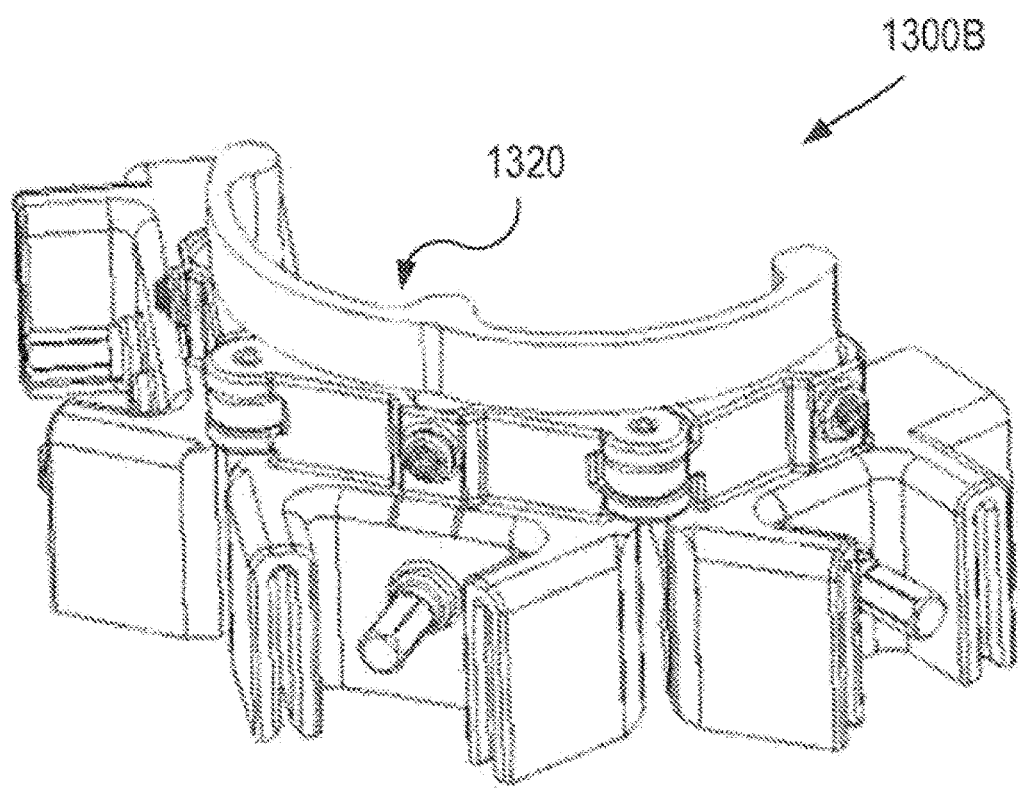

FIGS. 13A and 13B depict aspects of a cutting/alignment guide assembly, according to embodiments of the present invention. This embodiment provides a parasymphysis to parasymphysis (straight) cutting guide. As shown in FIG. 13A, a cutting/alignment guide assembly 1300A can include a cutting/alignment guide rigid bar 1310. The sections of the cutting/alignment guide assembly 1300A may be joined by hinges or other devices as depicted, or not joined at all. As shown in FIG. 13B, a cutting/alignment guide assembly 1300B (bent orientation) can include a cutting/alignment guide spring 1320. The sections of the cutting/alignment guide assembly 1300B may be joined by hinges or other devices as depicted, or not joined at all. FIG. 14A provides a cross-section view of aspects of a surgical system 1400 having a patient specific triangular plate 1470, according to embodiments of the present invention. System 1400 also includes an upper fibular graft 1442 and a lower fibular graft 1444. As shown in FIG. 14B, surgical system 1400 can also include a dental implant 1480 and one or more monocortical screws 1482A, 1482B. In some cases, a patient specific triangular plate can be installed between two rows of fibular grafts to provide the jaw structure while also allowing the screws going into fibular grafts to be recessed. Two rows of fibular grafts may be used on a case-by-case basis to build up bone height for positioning dental implants to be installed concurrently. In some cases, a triangular cross-section plate or a dental implant can include one or more recessed holes for receiving one or more screws, respectively.

Figure 15:
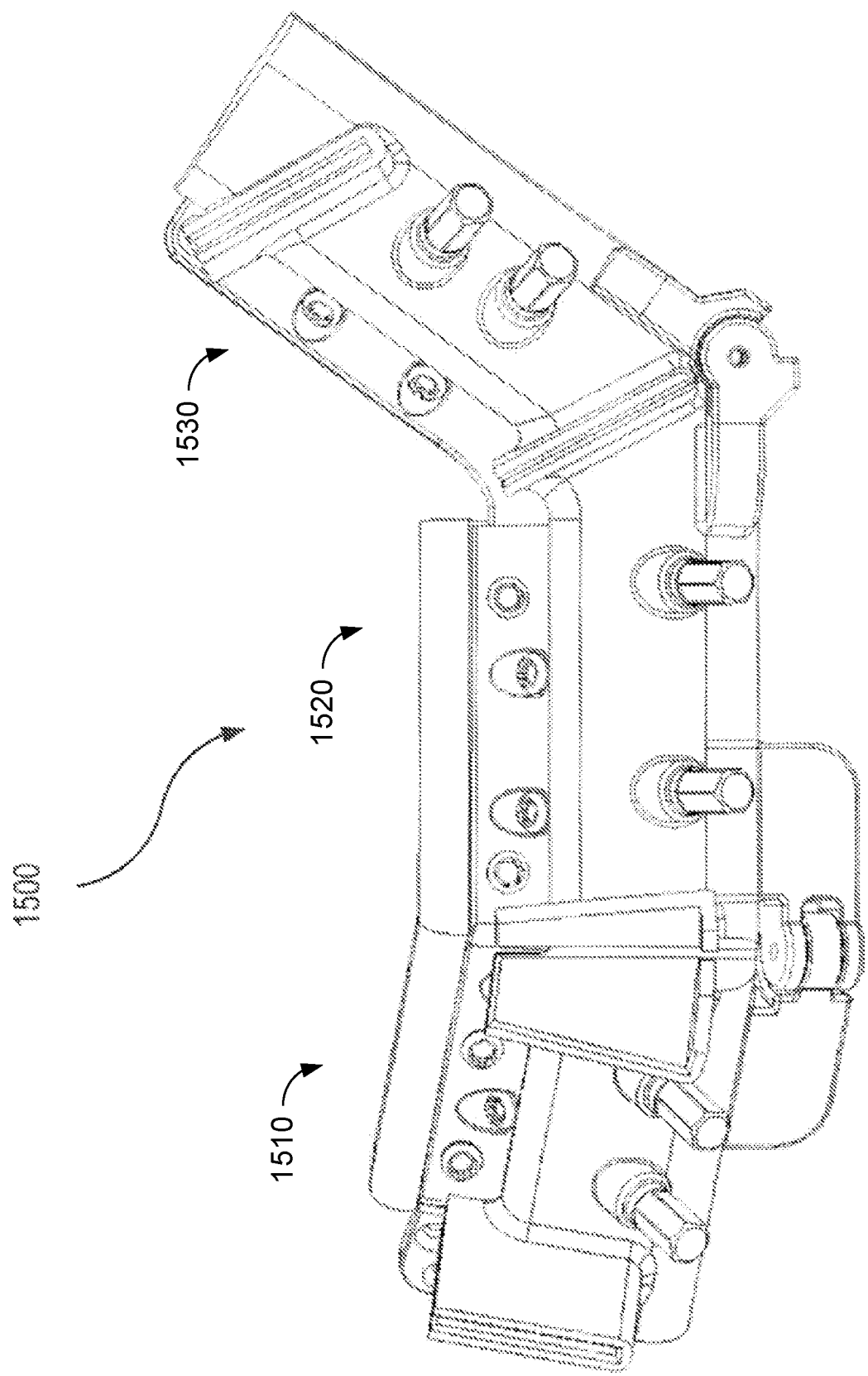
FIG. 15 illustrates aspects of a cutting guide assembly, in accordance with some embodiments.

FIG. 15 depicts aspects of a cutting/alignment guide assembly 1500 in a bent orientation, according to embodiments of the present invention. Referring to FIG. 15, the surgical system 1500 includes a left section 1510, a middle section 1520, and a right section 1530.

Figure 16:
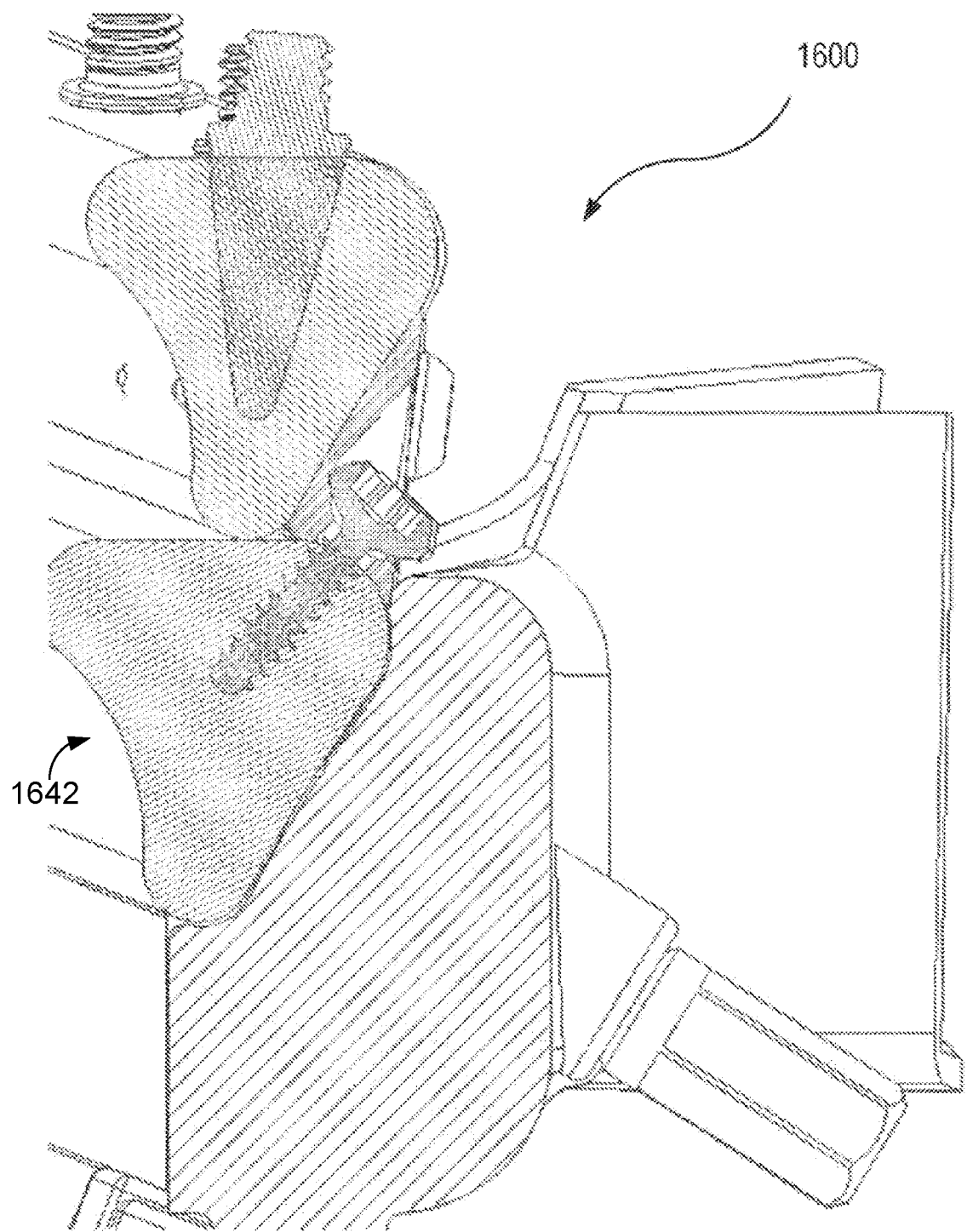
FIG. 16 illustrates aspects of a surgical system, in accordance with some embodiments.

FIG. 16 depicts aspects of a surgical system 1600, according to embodiments of the present invention. System 1600 also includes an upper fibular graft 1642 and a lower fibular graft 1644.

Figure 17:
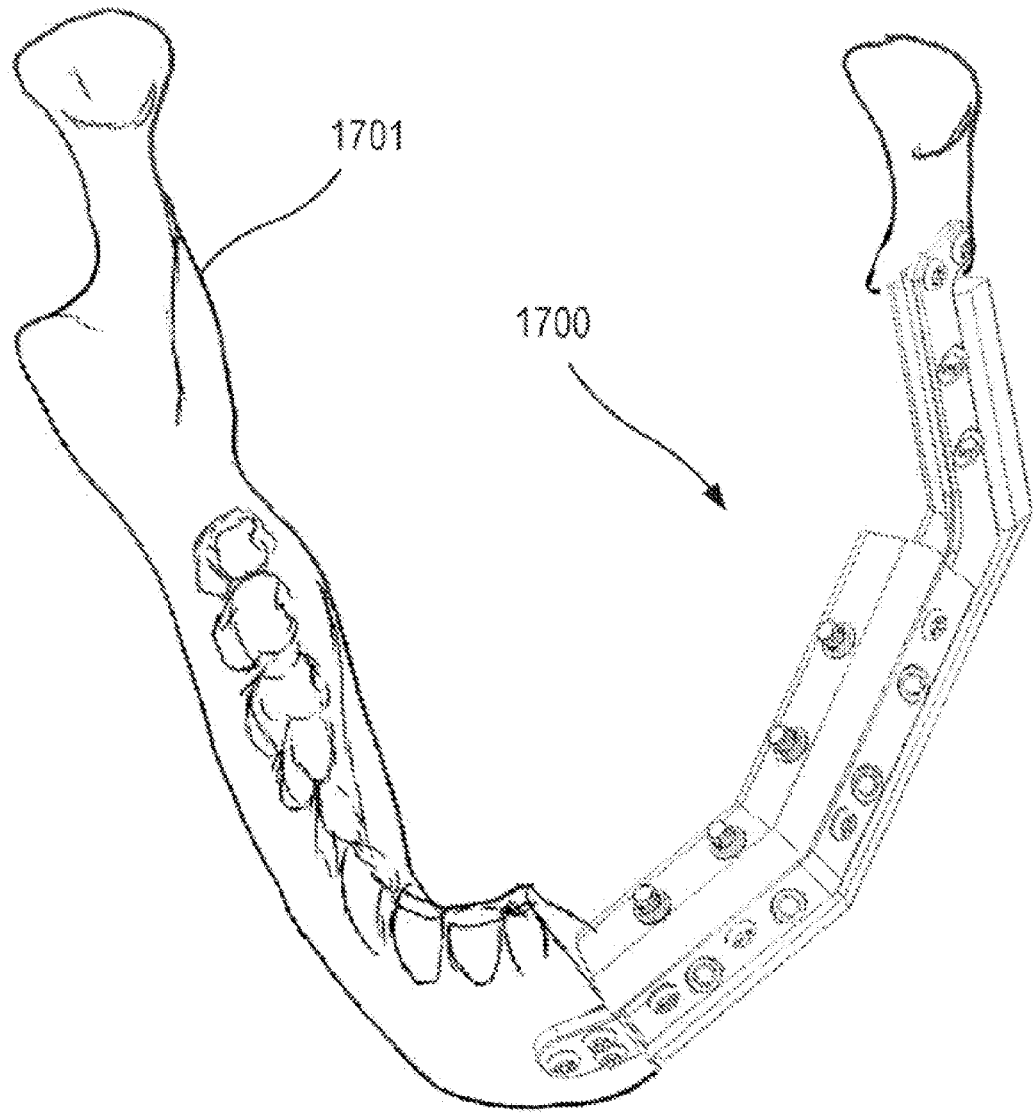
FIG. 17 illustrates aspects of a surgical system, in accordance with some embodiments.

FIG. 17 depicts aspects of a surgical system 1700, according to embodiments of the present invention. As shown in this superior view, the fibular grafts are installed in a native mandible or native mandibular defect 1701. This image shows the three screws on the native symphysis with two stacked on top of each other. It is understood that in exemplary embodiments, this can be done with all three screws positioned in a row.

Figure 18:
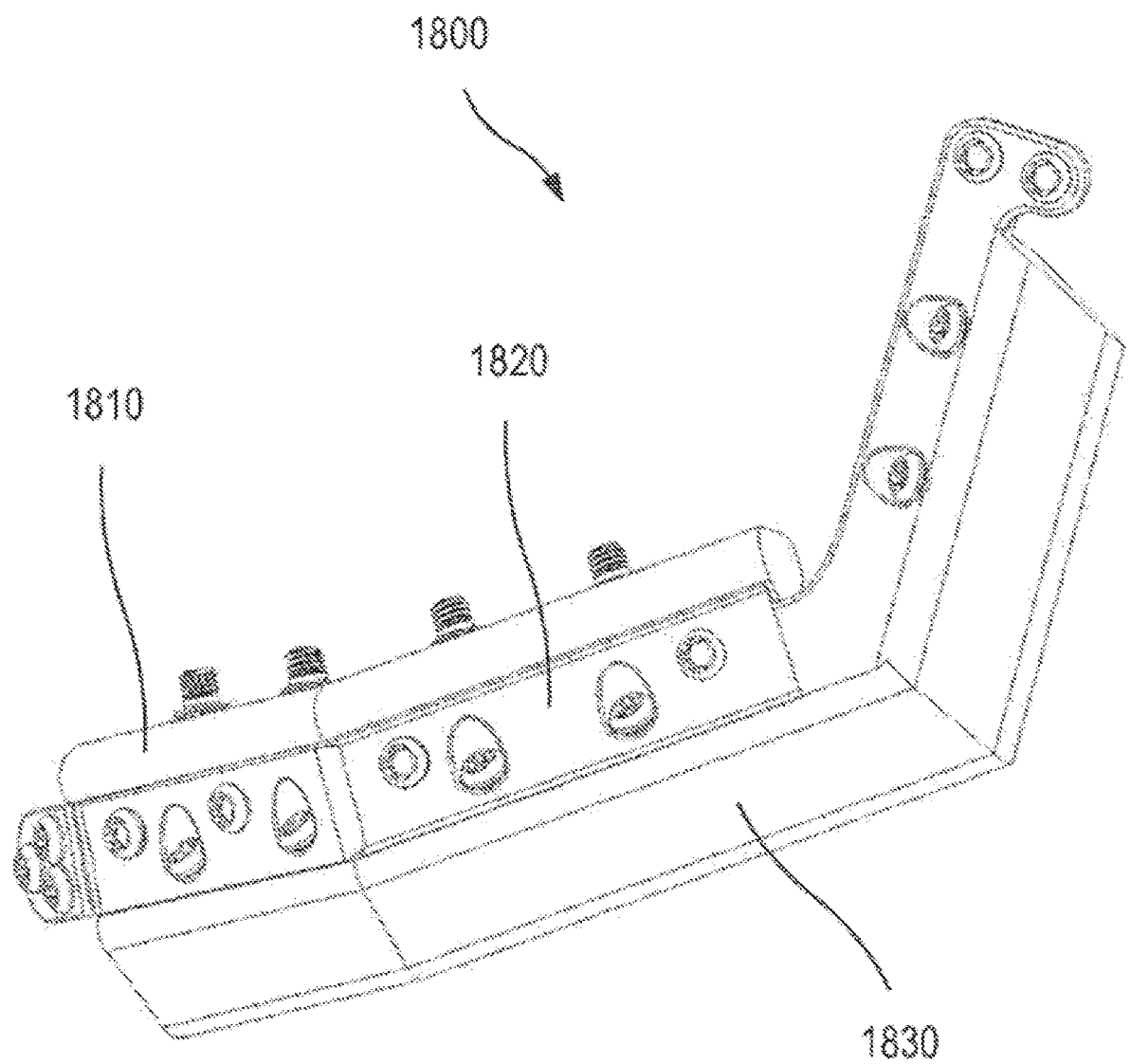
FIG. 18 illustrates aspects of a neo-mandible, in accordance with some embodiments.

FIG. 18 depicts aspects of a double rowed neo-mandible embodiment. The surgical system 1800 includes an upper fibular graft row 1810, a triangular plate 1820, and a lower fibular graft row 1830. In some cases, a patient specific triangular plate can be installed between two rows of fibular grafts to provide the jaw structure while also allowing the screws going into fibular grafts to be recessed. Two rows of fibular grafts may be used on a case-by-case basis to build up bone height for positioning dental implants to be installed concurrently.

Figure 19:
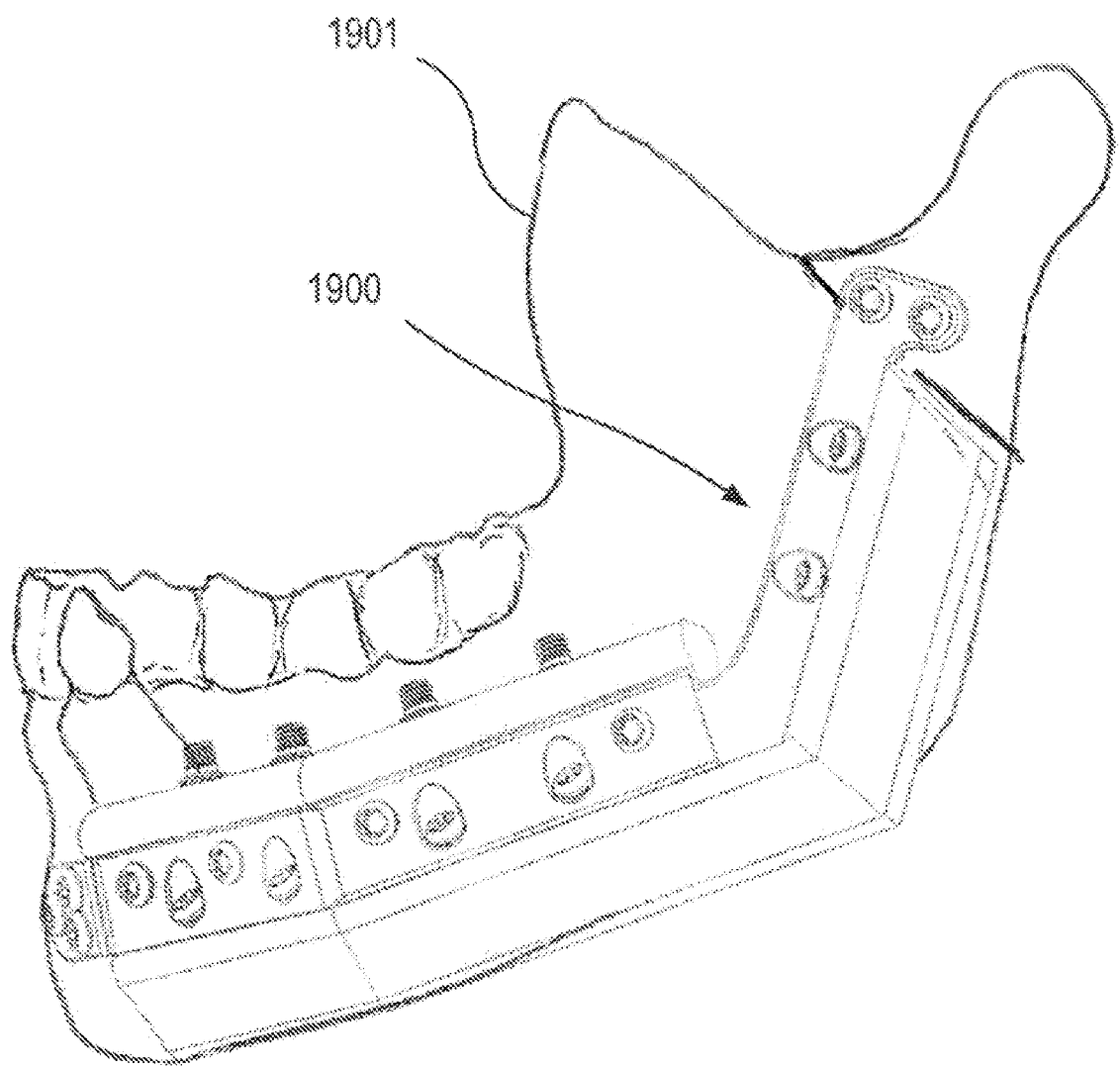
FIG. 19 illustrates aspects of a surgical system, in accordance with some embodiments.
Figure 20A:
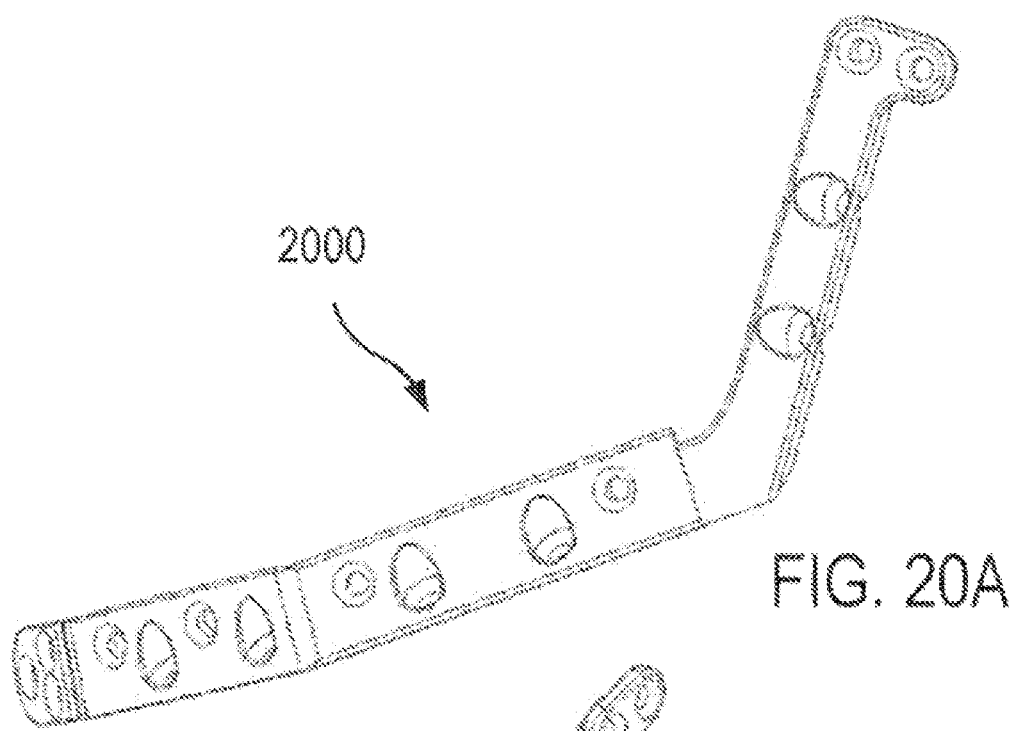
FIGS. 20A and 20B illustrate aspects of a triangular cross-section plate, in accordance with some embodiments.
Figure 20B:
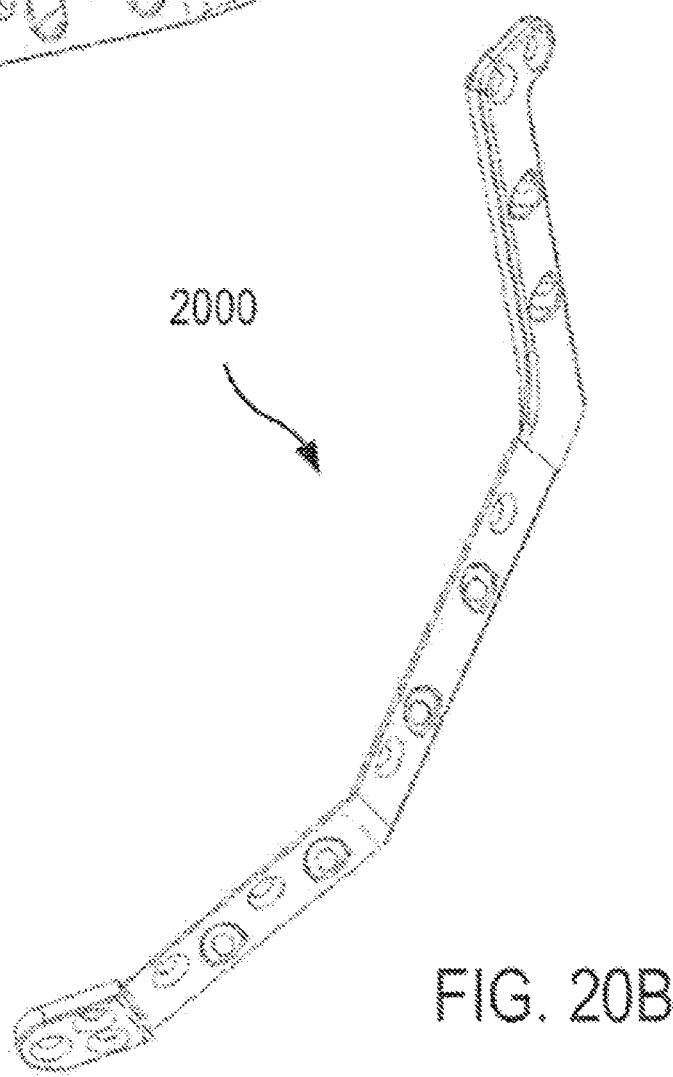

FIG. 19 depicts aspects of a surgical system 1900, according to embodiments of the present invention. As shown in this lateral view, the fibular grafts are installed in a native mandible or native mandibular defect 1901. FIGS. 20A and 20B depict aspects of a triangular plate 2000, according to embodiments of the present invention.

Figure 21A:
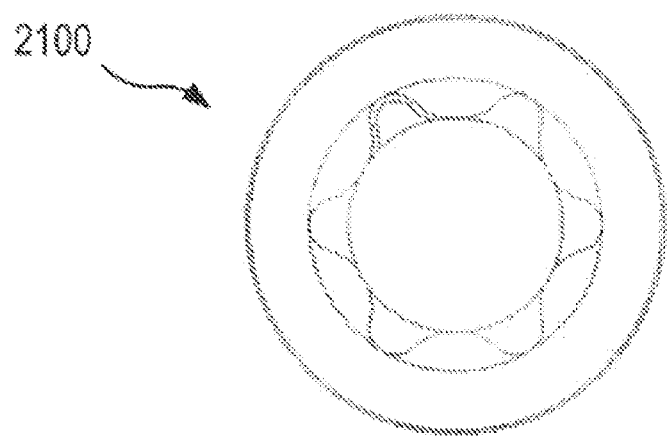
FIGS. 21A and 21B illustrate aspects of a screw, in accordance with some embodiments.
Figure 21B:
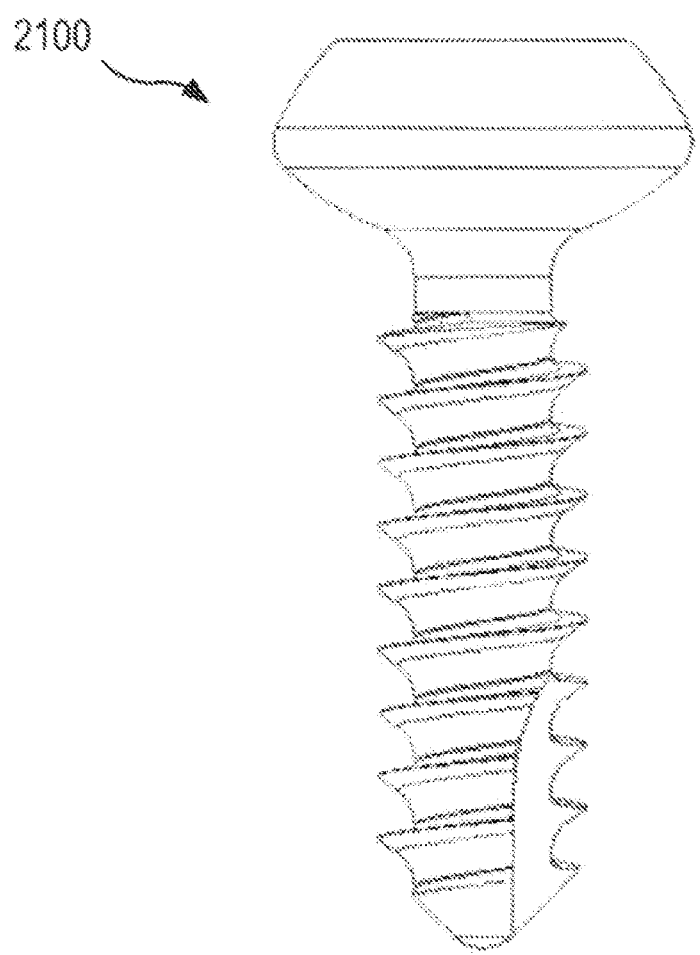

FIGS. 21A and 21B depict aspects of a monocortical fixation screw 2100, according to embodiments of the present invention. In some cases, the screw 2100 can be a HA 2×7 mm T10 hexalobe screw.

Figure 22A:
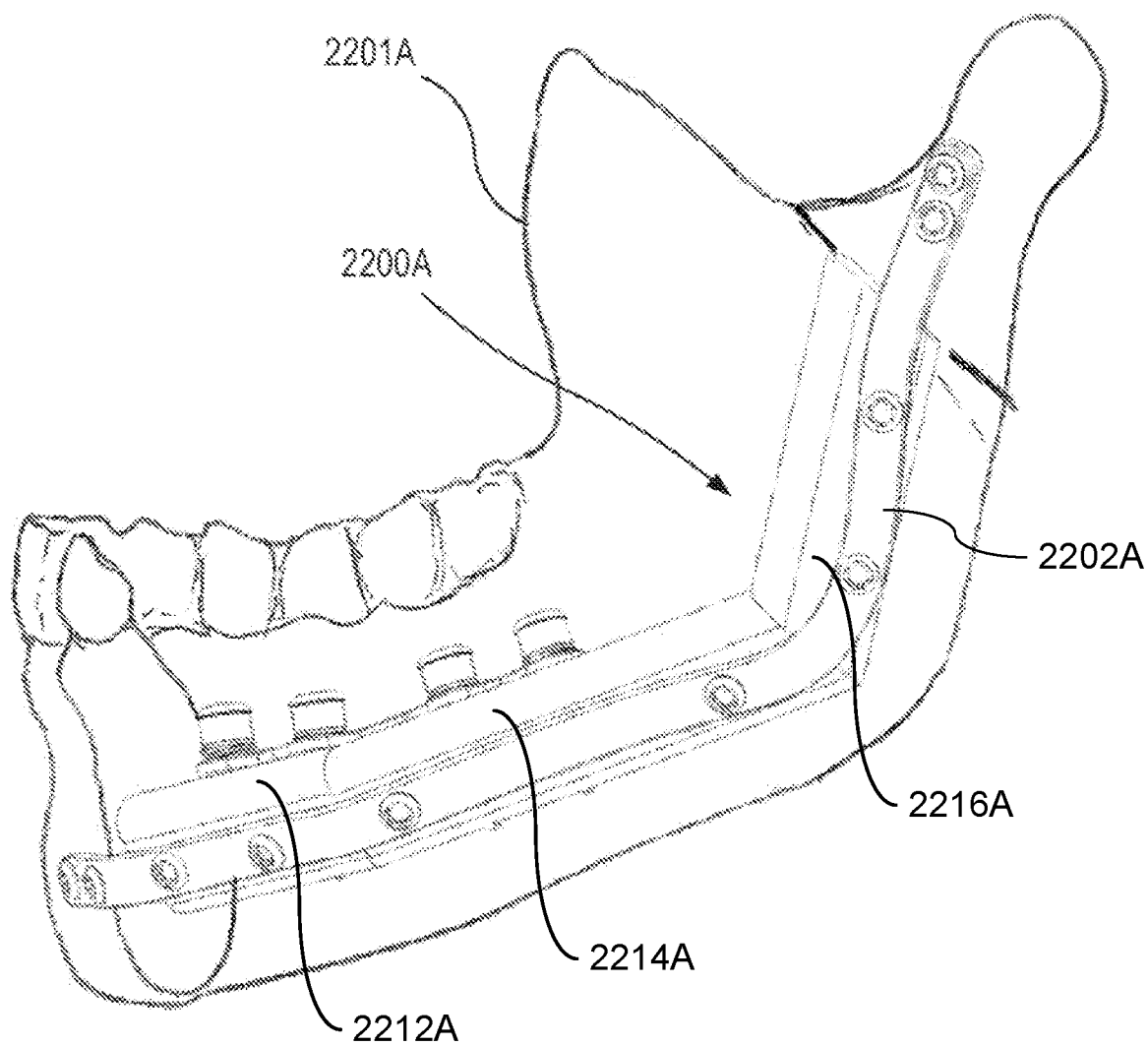
FIG. 22A illustrates aspects of a surgical system, in accordance with some embodiments.

FIG. 22A depicts aspects of a surgical system 2200A, according to embodiments of the present invention. As shown in this lateral view, three fibular grafts 2212A, 2214A, and 2216A are installed in a native mandible 2201A. In this figure, the surgical system 2200A is provided as a single fibular graft row embodiment, and a tension band 2202A engages two of the three segments, while the third segment is free.

Figure 22B:
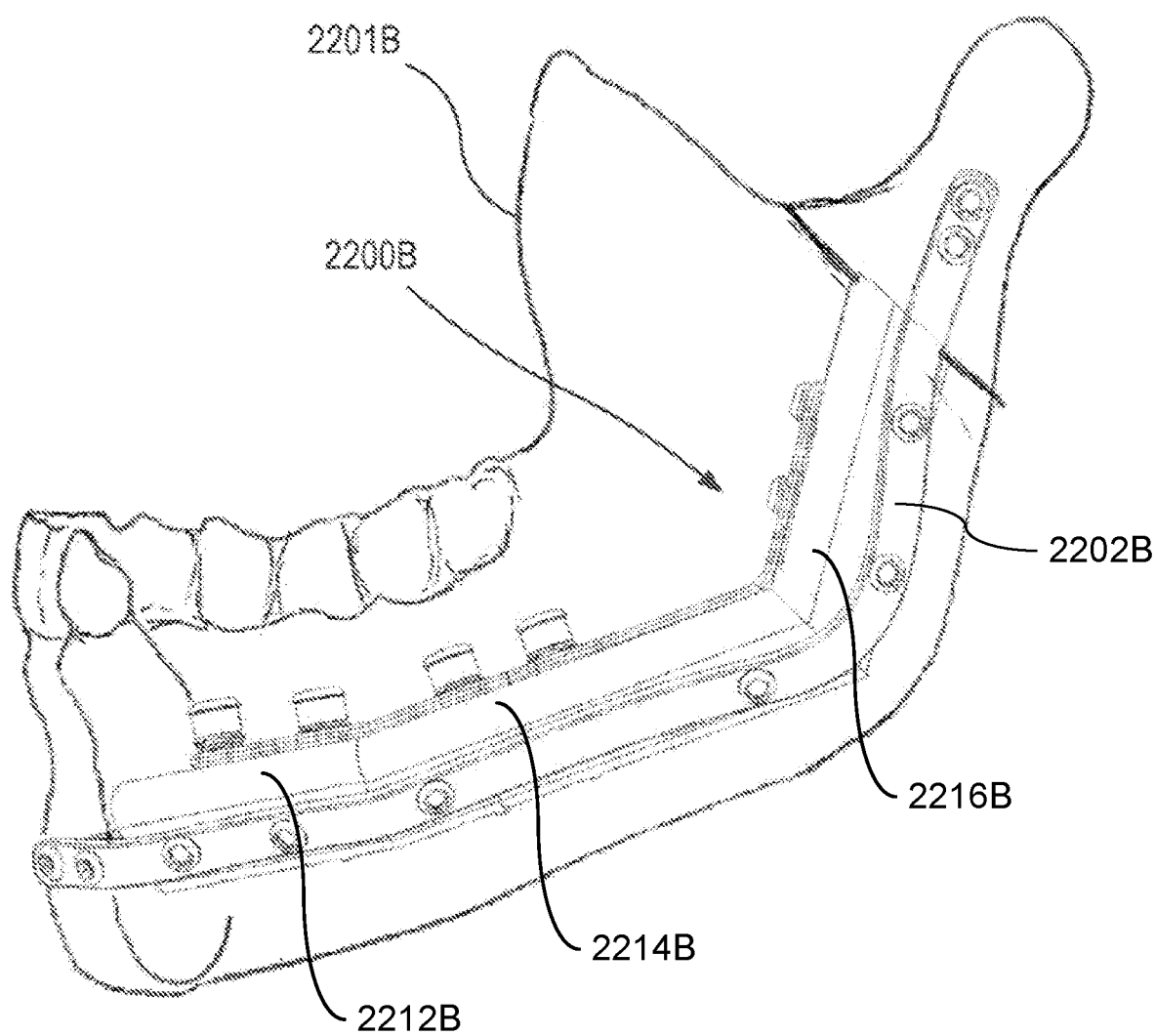
FIGS. 22B and 22C illustrate aspects of a related surgical system, in accordance with some embodiments.

FIG. 22B depicts aspects of a surgical system 2200B, according to embodiments of the present invention. As shown in this lateral view, three fibular grafts 2212B, 2214B, and 2216B are installed in a native mandible 2201B. In this figure, the surgical system 2200B is provided as a single fibular graft row embodiment, and a tension band 2202B engages each of the three segments. Hence, in contrast to FIG. 22A, it can be seen in FIG. 22B that a tensioning plate can be extended to interface with the third fibular graft 2216B.

Figure 22C:
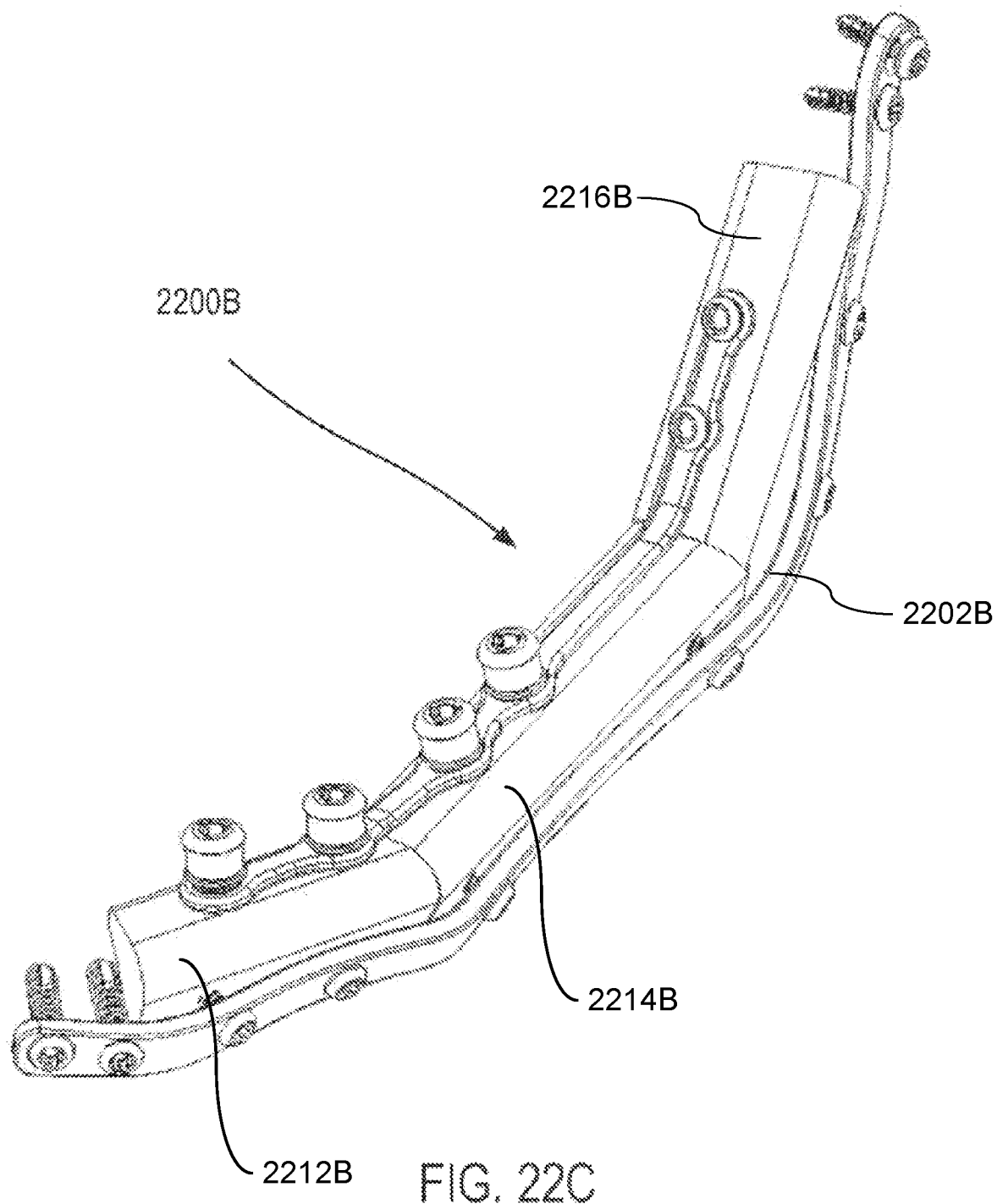

FIG. 22C provides another view of aspects of surgical system 2200B. In this view, it can be seen that embodiments of the present invention encompass a single rowed neo-mandible having three fibular grafts 2212B, 2214B, and 2216B with a tensioning band 2202B that connects to the third fibular graft 2216B with mono-cortical screws. Hence, the tensioning band 2202B can involve all segments and the screws on the tensioning band 2202B in the non-implant position can simply be monocortical screws. Accordingly, with the tensioning band 2202B going over all segments, the fibular grafts 2212B, 2214B, and 2216B can maintain their 3-D relationship throughout the reconstruction, which is one of the major advantages of this system. In this image depicting a single fibular graft row with a rectangular plate and dental tensioning band 2202B, there is little or no space between the plate and the upper ramus section of the neo-mandible.

Figure 23:
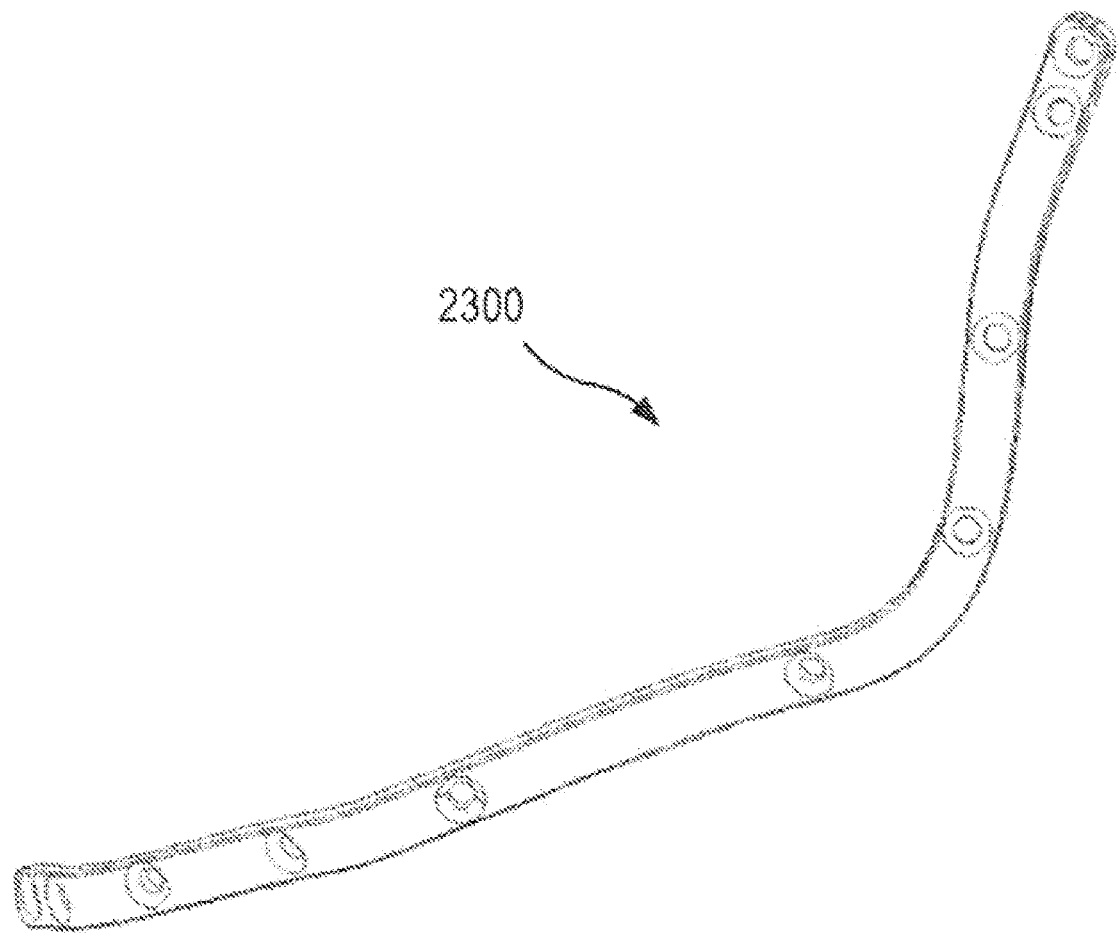
FIG. 23 illustrates aspects of a rectangular cross-section plate, in accordance with some embodiments.

FIG. 23 depicts aspects of a tensioning band 2300, according to embodiments of the present invention. In some cases, a rectangular plate can be used in the mid-mandibular position with the tensioning band for dental implantation. It is understood that embodiments of the present invention encompass two reconstruction formations with the single barrel configuration. In one reconstruction formation with a triangular plate, the fibular pieces are held in place as with the double barrel configuration and the fixation plate is placed against the fibula to make the neo-mandible. In another reconstruction formation with a rectangular plate, the tension band is placed, the temporary screws and fixation holding the fibular pieces is removed, and the rectangular plate is applied.

FIGS. 24A, 24B, 24C, and 24D depict certain optional aspects of preoperative planning cutting planes, according to some embodiments of the present invention. In some embodiments, cuts can be made equally about the orthogonal axis. In some instances, not having equal cuts may result in an offset on one side. In some embodiments, fibular cuts can be made equally about the orthogonal axis. In some instances, not having equally angled cuts can result in an offset on one side on the graft. Notwithstanding the above, it is understood that in some embodiments, configurations may not be designed as they are shown here. In some cases, the fibula changes caliber and therefore the osteotomies are intentionally not designed exactly around the orthogonal axis so as to create the correction for what would otherwise be a mismatch.

Figure 25:
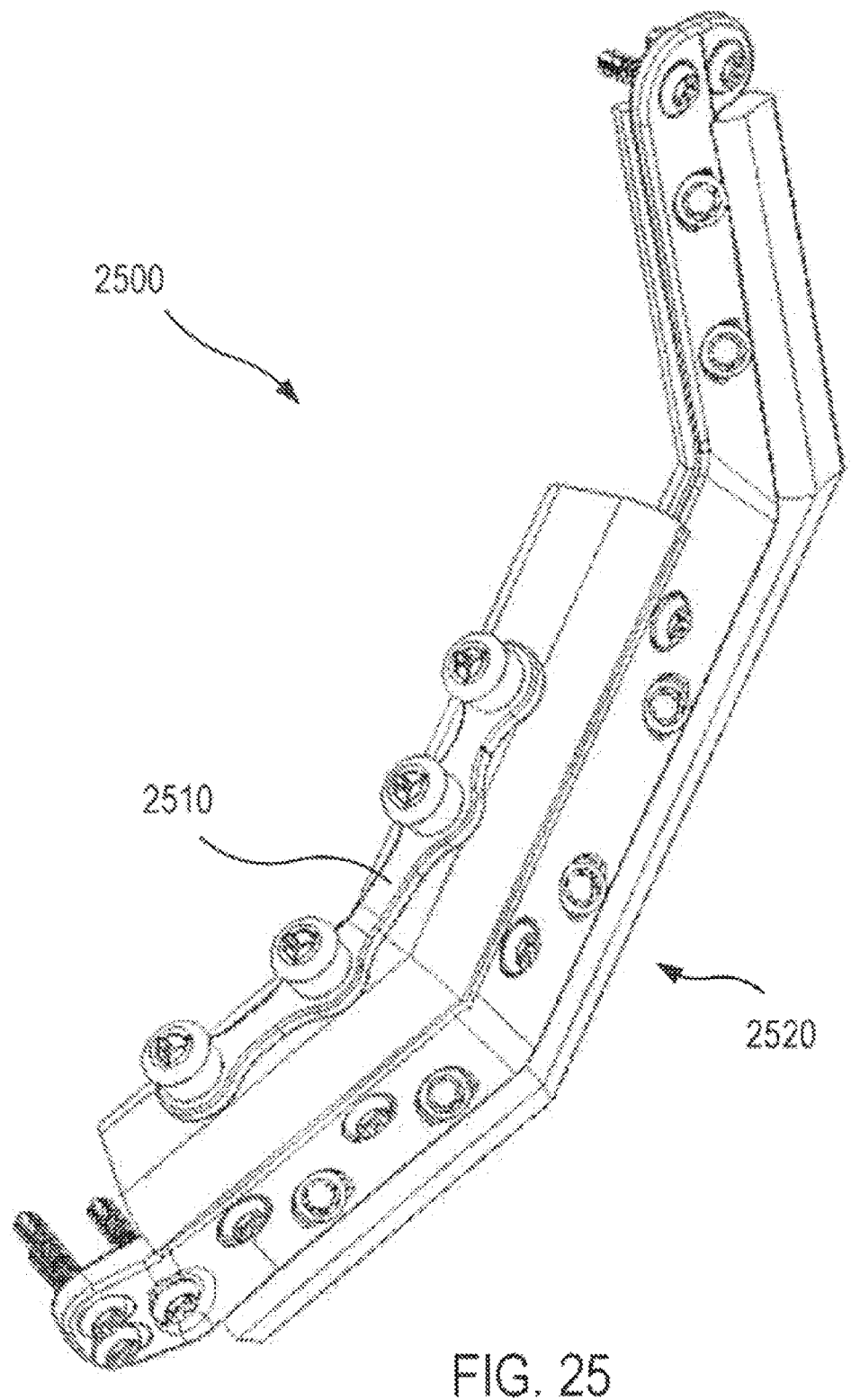
FIG. 25 illustrates aspects of a surgical system, in accordance with some embodiments.
Figure 26:
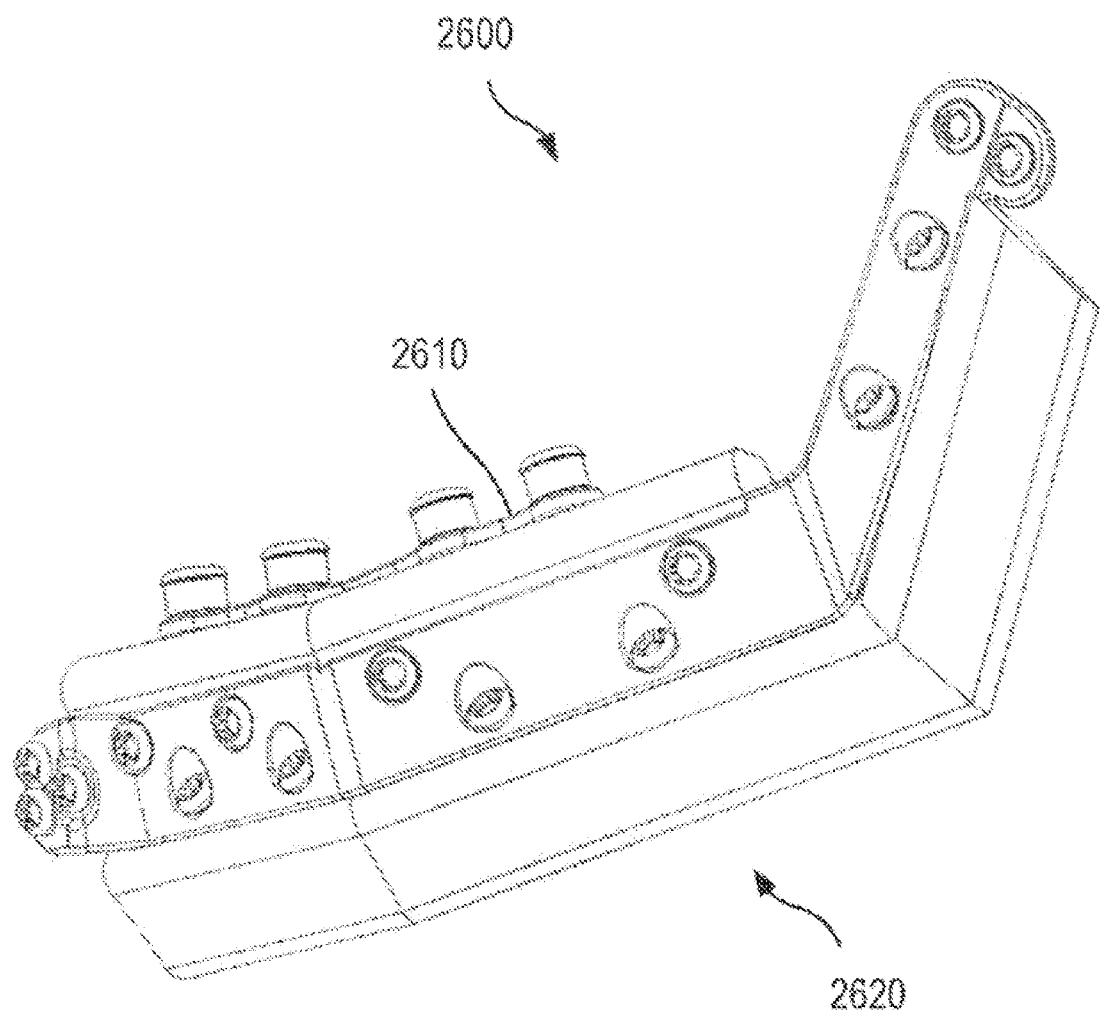
FIG. 26 illustrates aspects of a surgical system, in accordance with some embodiments.

FIG. 25 depicts aspects of a surgical system 2500, according to embodiments of the present invention. As shown here, a system 2500 can include a dental tensioning plate 2510 placed on a neo-mandible 2520. In some embodiments, the neo-mandible assembly 2520 includes one or more sections coupled with one or more respective bone graft segments. An individual bone graft segment can be a fibular bone graft segment, for example. FIG. 26 depicts aspects of a surgical system 2600, according to embodiments of the present invention. As shown here, a system 2600 can include a dental tensioning plate 2610 placed on a neo-mandible assembly 2620.

Figure 27:
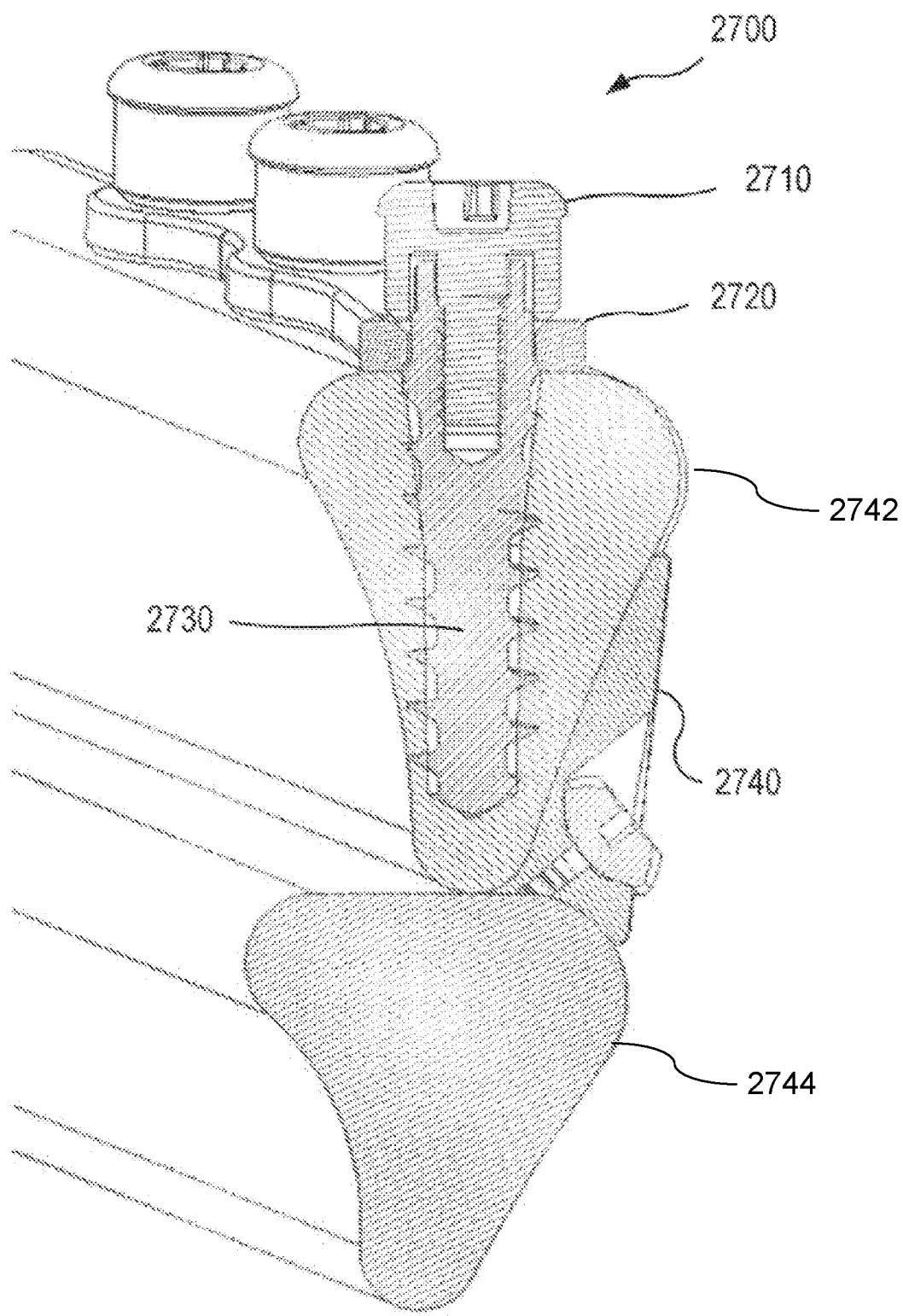
FIG. 27 illustrates aspects of a surgical system, in accordance with some embodiments.

FIG. 27 depicts aspects of a surgical system 2700, according to embodiments of the present invention. Referring to FIG. 27, the system 2700 includes an upper fibular graft 2742 and a lower fibular graft 2744. As shown here, a system 2700 can include a snap abutment 2710, a dental tensioning plate 2720, a dental screw 2730, and a triangular plate 2740. As illustrated in this figure, the surgical system 2700 can be provided as a dental plate and orthopedic dental implant embodiment. In some cases, a patient specific triangular plate can be installed between two rows of fibular grafts to provide the jaw structure while also allowing the screws going into fibular grafts to be recessed. Two rows of fibular grafts may be used on a case-by-case basis to build up bone height for positioning dental implants to be installed concurrently.

Figure 28:
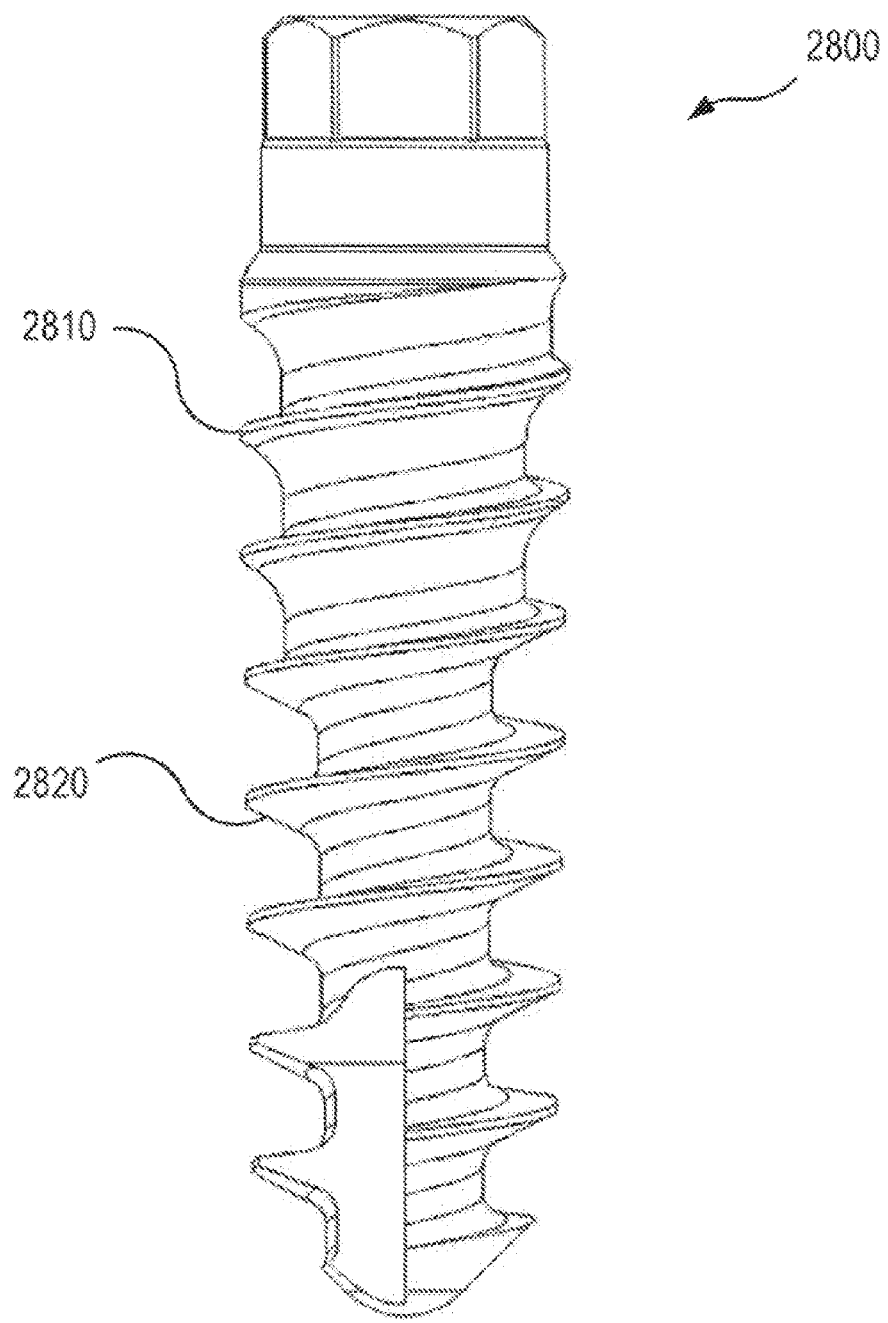
FIG. 28 illustrates aspects of a screw, in accordance with some embodiments.
Figure 29A:
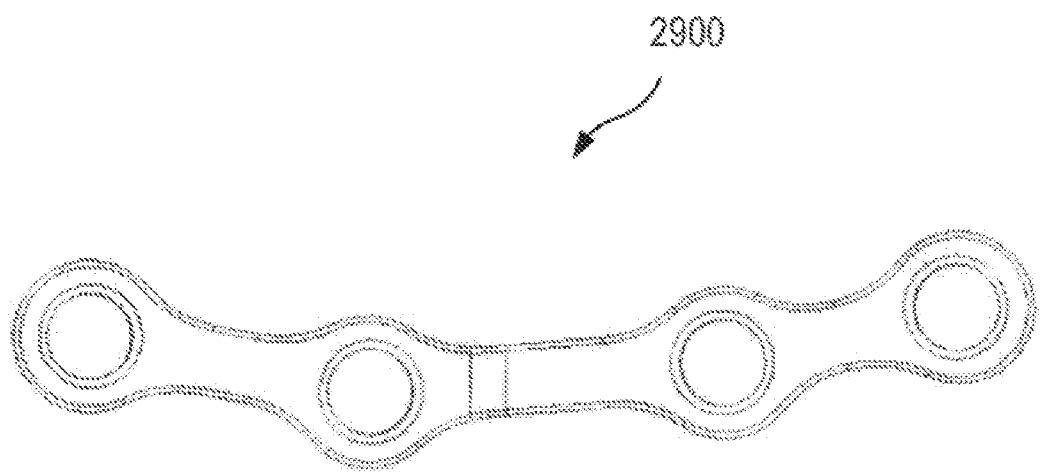
FIGS. 29A and 29B illustrate aspects of a dental tensioning plate, in accordance with some embodiments.
Figure 29B:
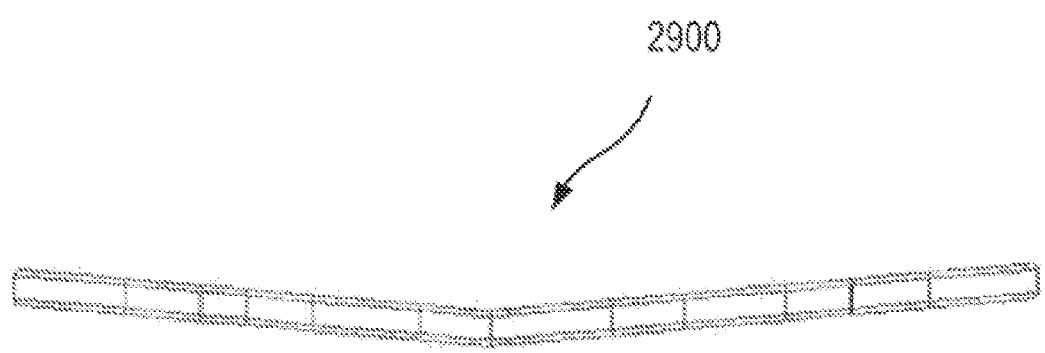
Figure 30:
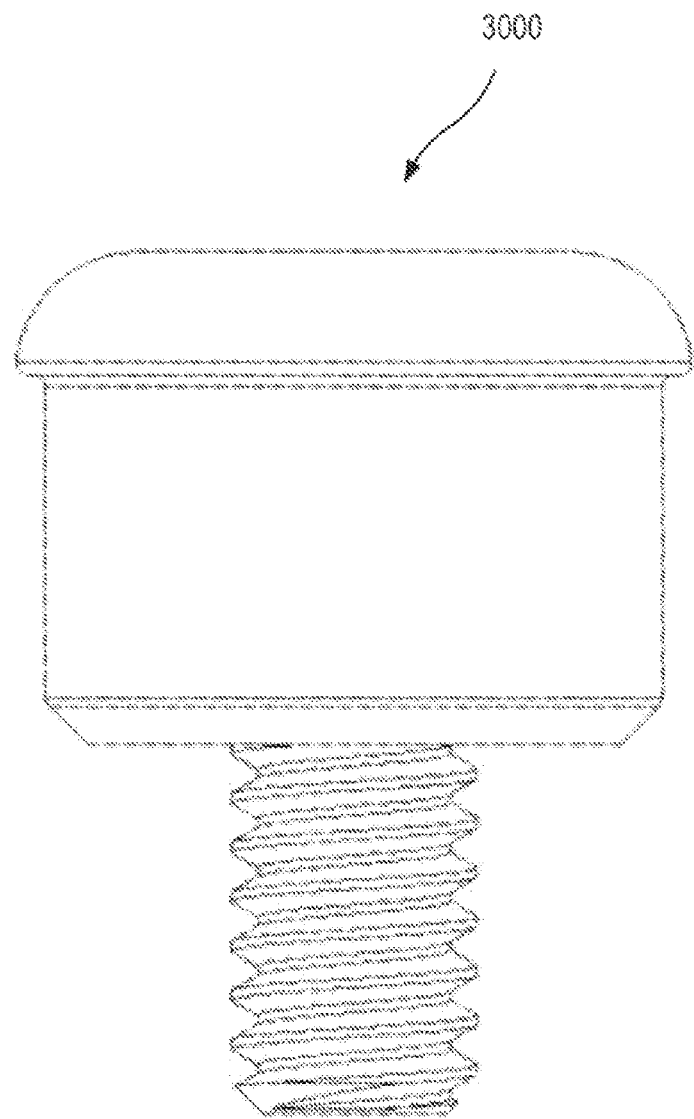
FIG. 30 illustrates aspects of a denial locator abutment, in accordance with some embodiments.

FIG. 28 depicts aspects of a screw 2800, according to embodiments of the present invention. In some cases, the screw 2800 can be a monocortical dental screw. In some cases, the screw 2800 can include a cortical fixation thread 2810 and a cancellous fixation thread 2820. In some embodiments surface treatments or coating (porous structure) may be used to enhance osteointegration. FIGS. 29A and 29B depict aspects of a dental tensioning plate 2900, according to embodiments of the present invention. FIG. 30 depicts aspects of a dental locator abutment 3000, according to embodiments of the present invention.

Figure 31:
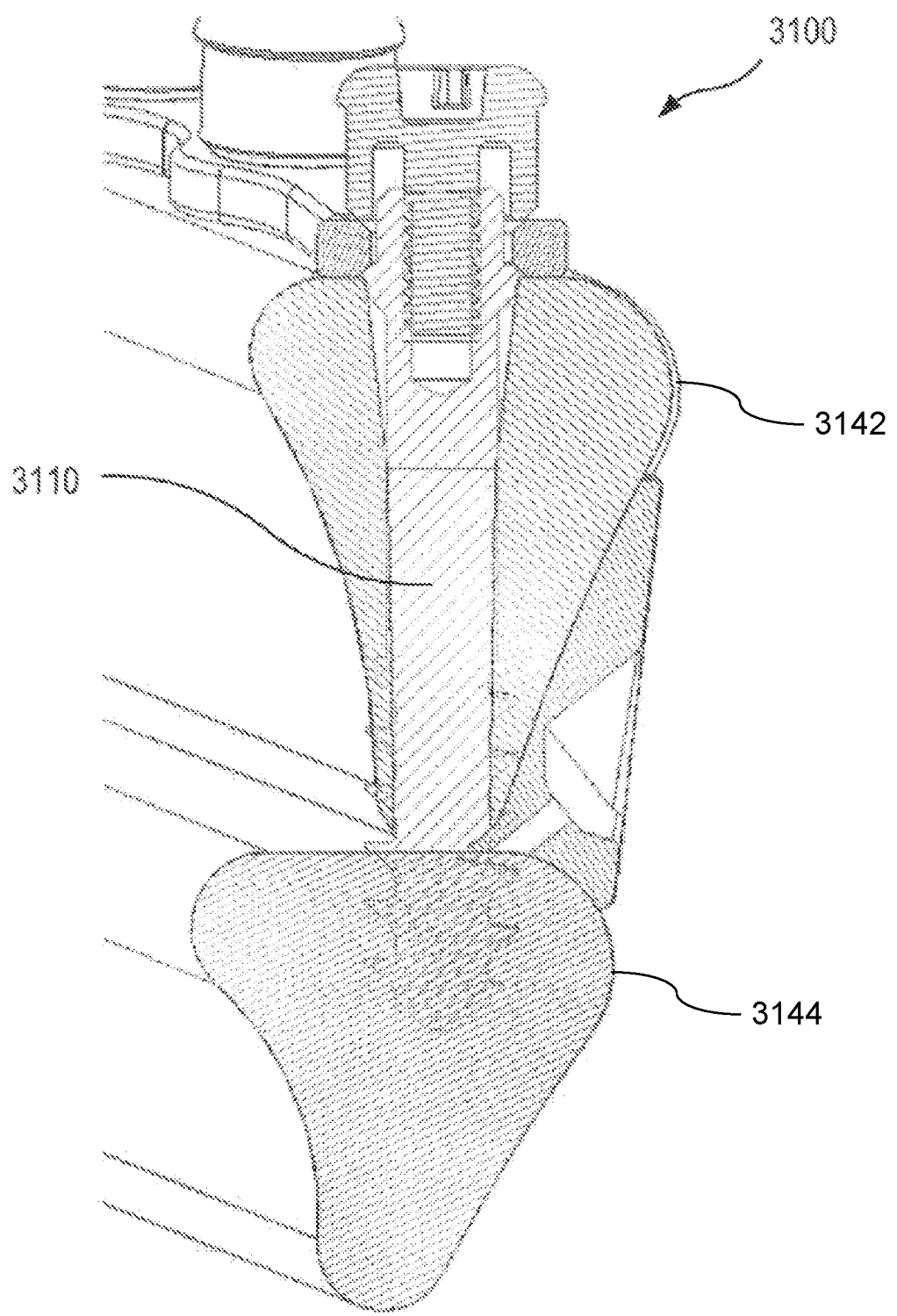
FIG. 31 illustrates aspects of a surgical system, in accordance with some embodiments.
Figure 32:
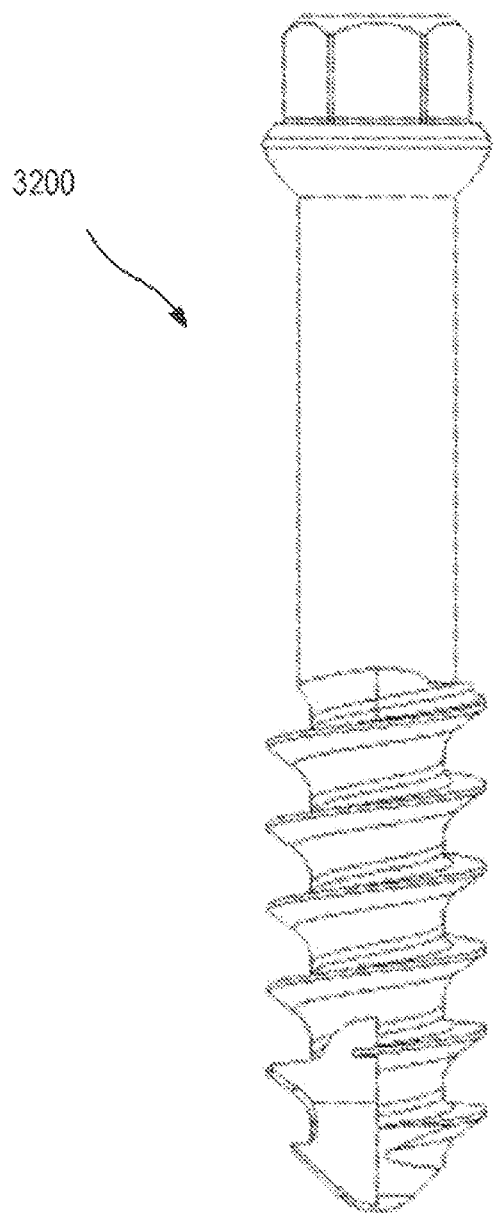
FIG. 32 illustrates aspects of a dental lag screw, in accordance with some embodiments.
Figure 33:
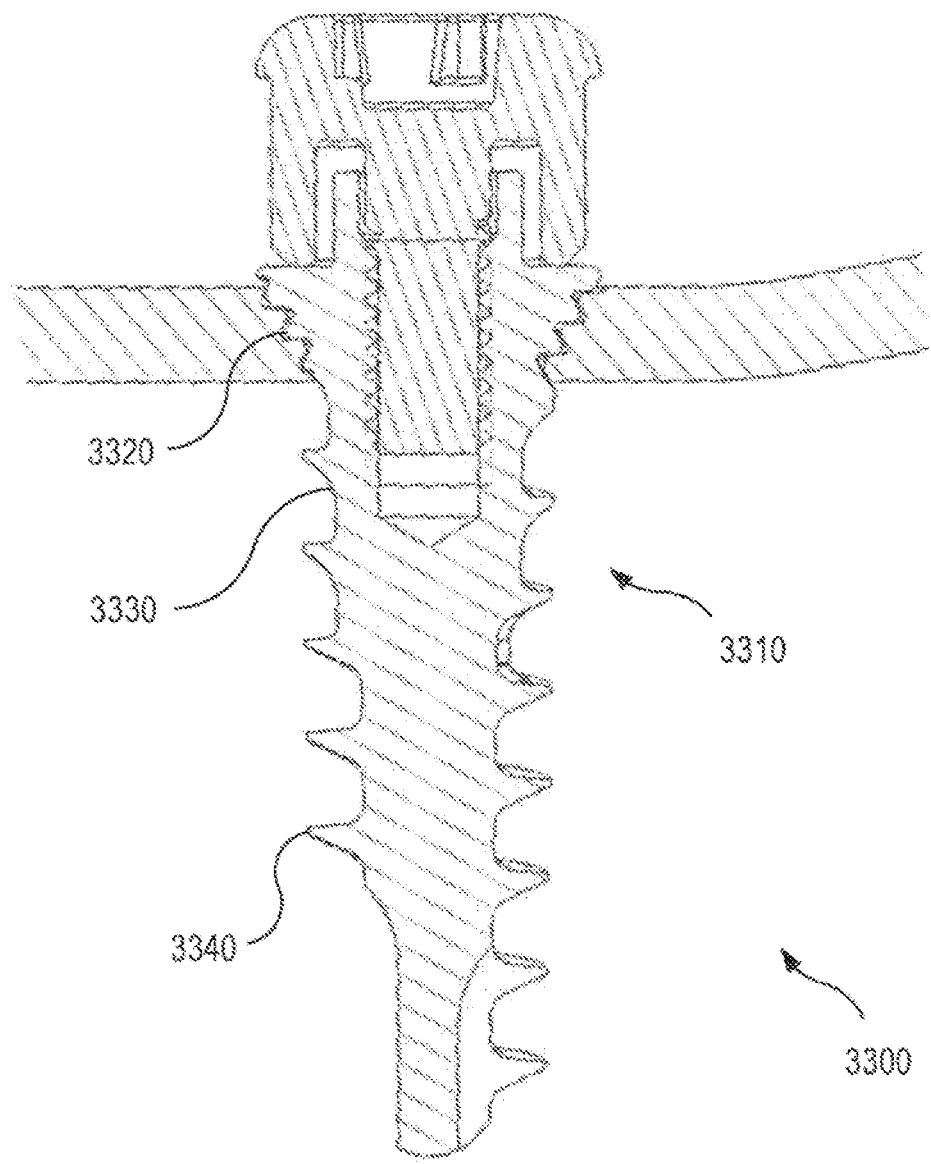
FIG. 33 illustrates aspects of a threaded plate and locking dental screw combination, in accordance with some embodiments.
Figure 34:
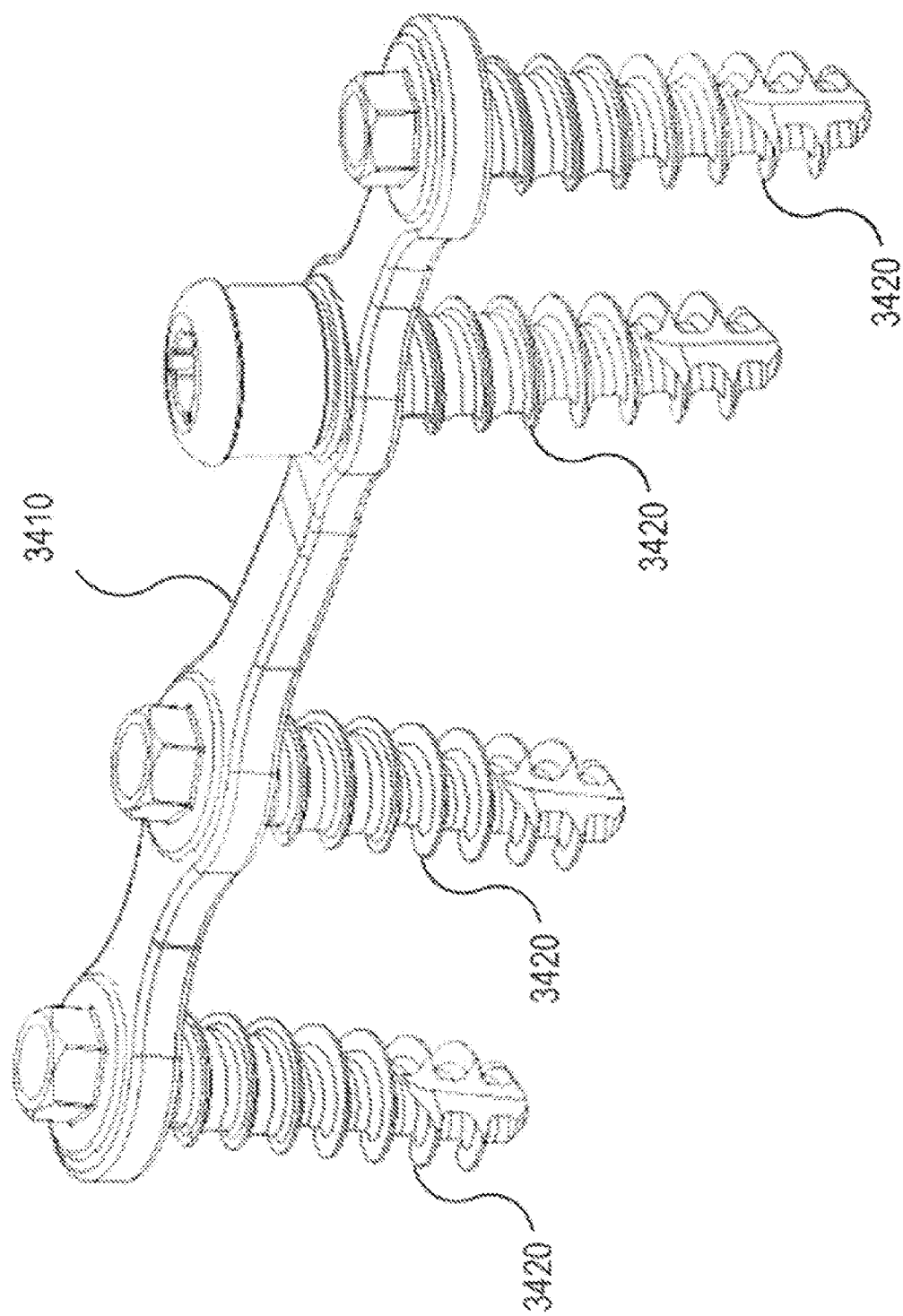
FIG. 34 illustrates aspects of a threaded plate and locking dental screw combination, in accordance with some embodiments.

FIG. 31 depicts aspects of a surgical system 3100, according to embodiments of the present invention. Referring to FIG. 31, the system 3100 includes an upper fibular graft 3142 and a lower fibular graft 3144. As shown here, a system 3100 can include a lag screw 3110 that goes through both rows of fibula. FIG. 32 depicts aspects of a dental lag screw 3200, according to embodiments of the present invention. FIG. 33 provides a cross-section view of a threaded plate and locking dental screw embodiment. As shown here, the surgical system 3300 includes a screw 3310 having a triple-lead m thread 3320, a cortical fixation thread 3330, and a cancellous fixation thread 3340. In some cases, all threads have the same pitch. FIG. 34 depicts aspects of an embodiment having a threaded plate 3410 and locking dental screws 3420.

Figure 35A:
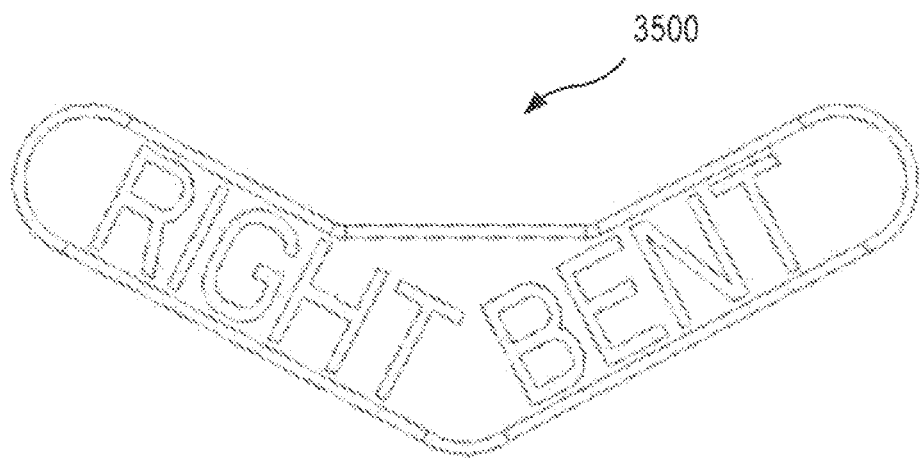
FIGS. 35A and 35B illustrate aspects of a right hinge angle lock, in accordance with some embodiments.
Figure 35B:
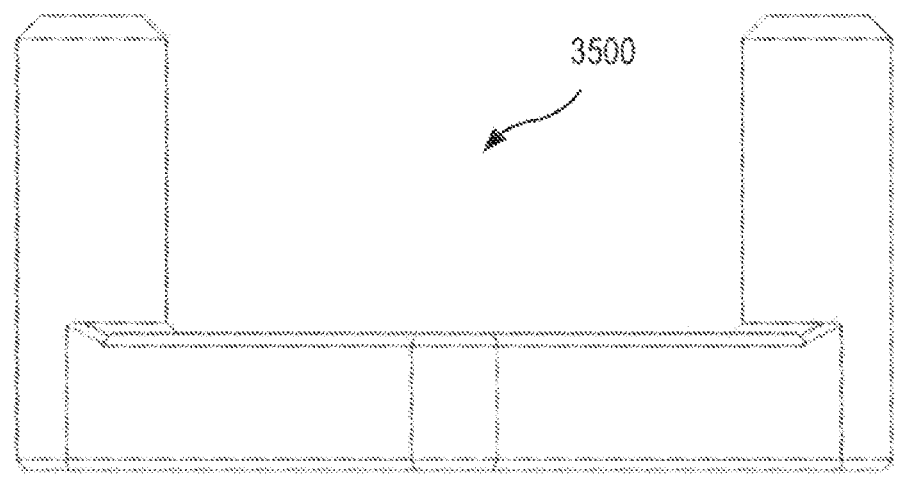
Figure 36A:
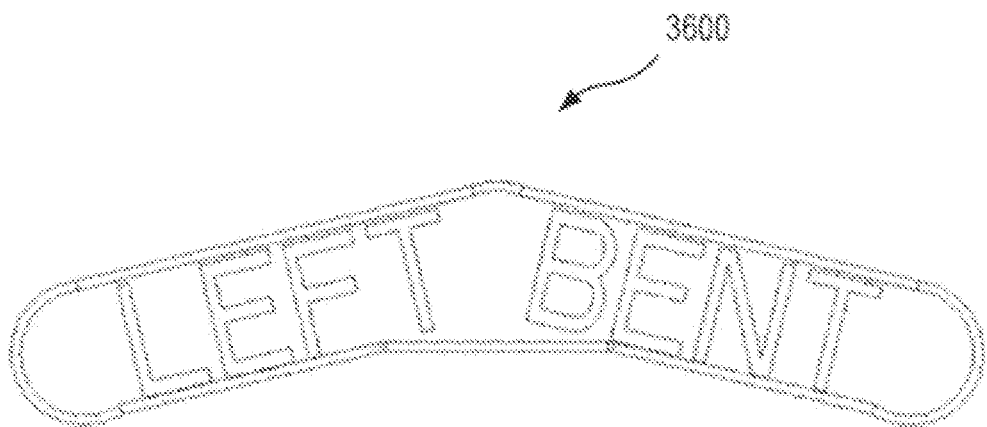
FIGS. 36A and 36B illustrate aspects of a left hinge angle lock, in accordance with some embodiments.
Figure 36B:
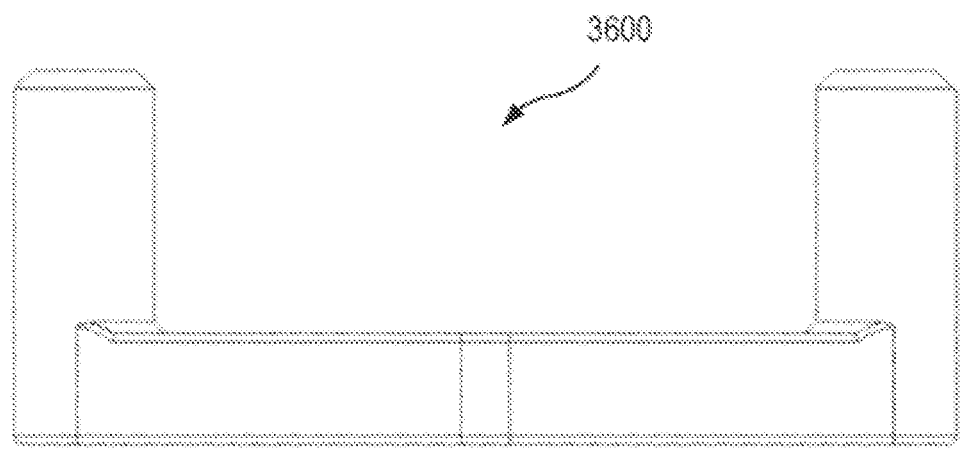
Figure 37A:
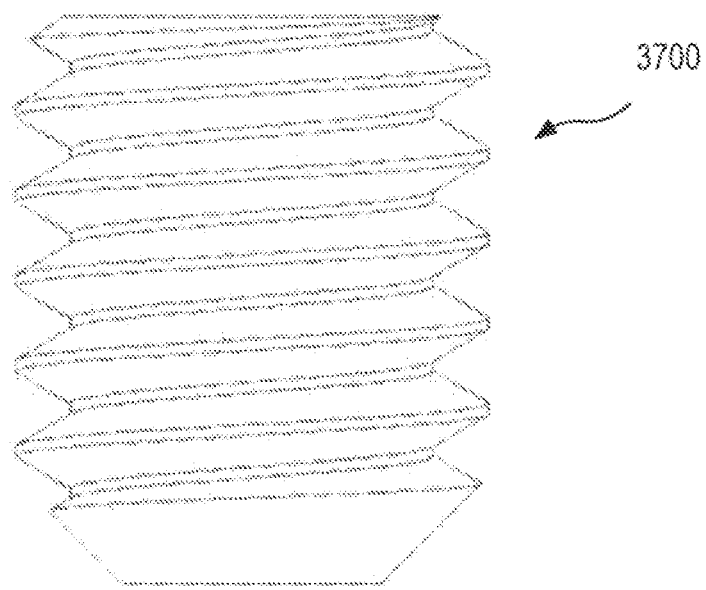
FIGS. 37A and 37B illustrate aspects of a set screw, in accordance with some embodiments.
Figure 37B:
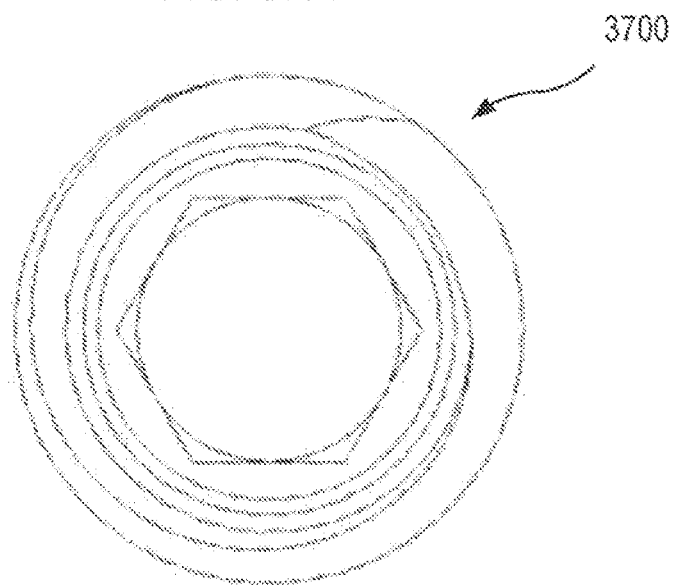
Figure 38:
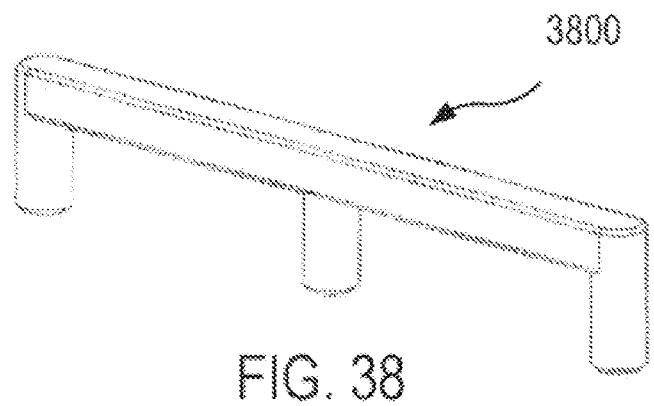
FIG. 38 illustrates aspects of a cutting/alignment guide rigid bar, in accordance with some embodiments.
Figure 39A:
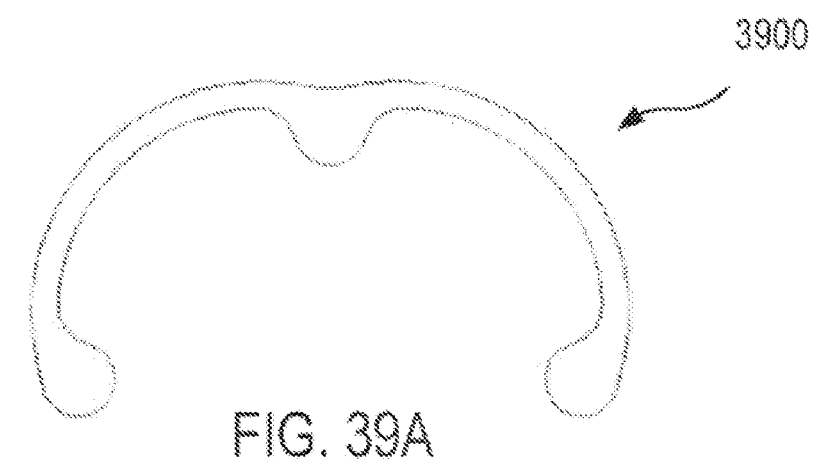
FIGS. 39A and 39B illustrate aspects of a cutting/alignment guide spring, in accordance with some embodiments.
Figure 39B:
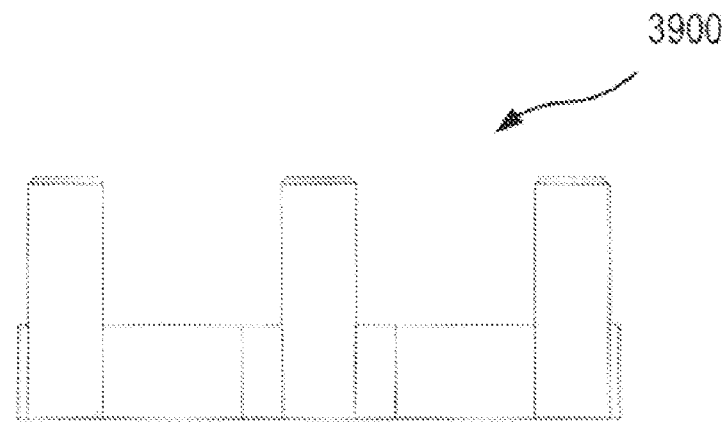

FIGS. 35A and 35B depict aspects of a right hinge angle lock 3500, according to embodiments of the present invention. FIGS. 36A and 36B depict aspects of a left hinge angle lock 3600, according to embodiments of the present invention. FIGS. 37A and 37B depict aspects of a set screw 3700, according to embodiments of the present invention. In some cases, a set screw 3700 can be a M2.5×3 mm set screw. FIG. 38 depicts aspects of a cutting/alignment guide rigid bar 3800, according to embodiments of the present invention. FIGS. 39A and 39B depict aspects of a cutting/alignment guide spring 3900, according to embodiments of the present invention.

Figure 40:
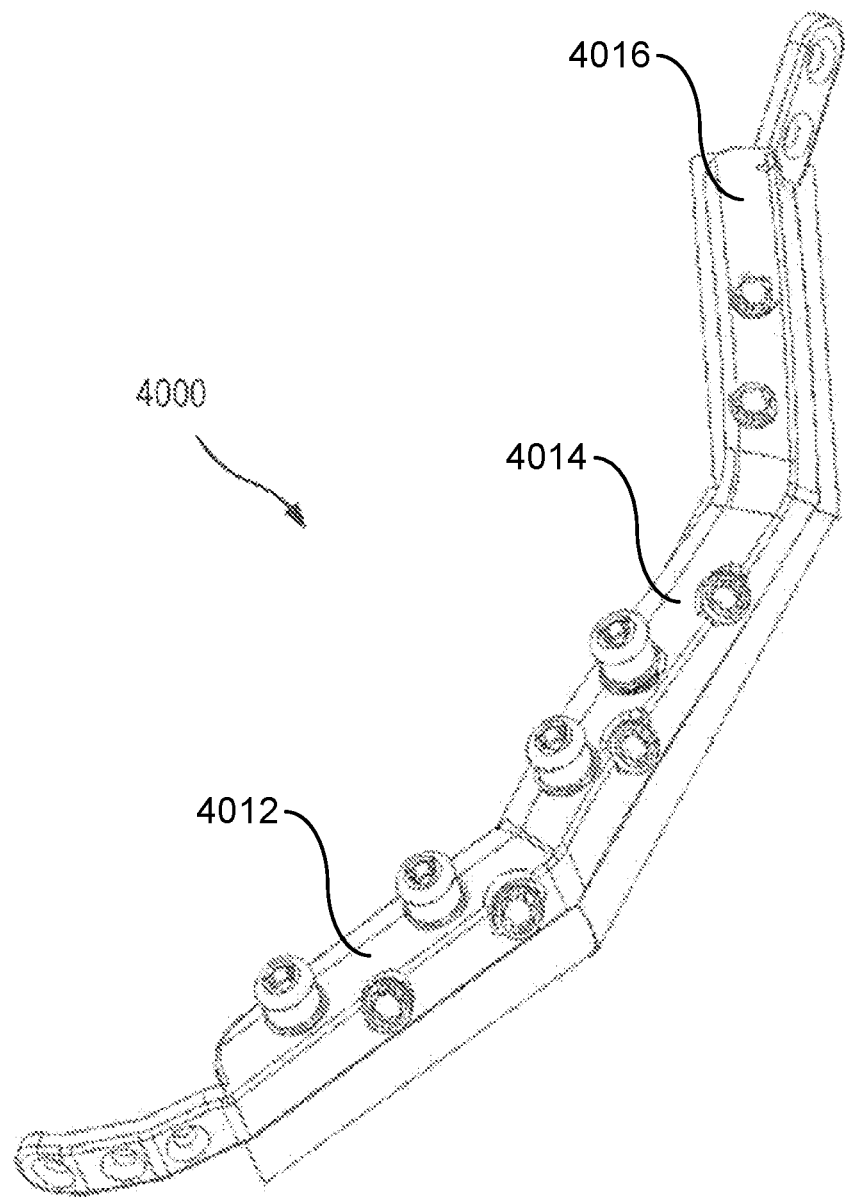
FIG. 40 illustrates aspects of a surgical system, in accordance with some embodiments.
Figure 41:
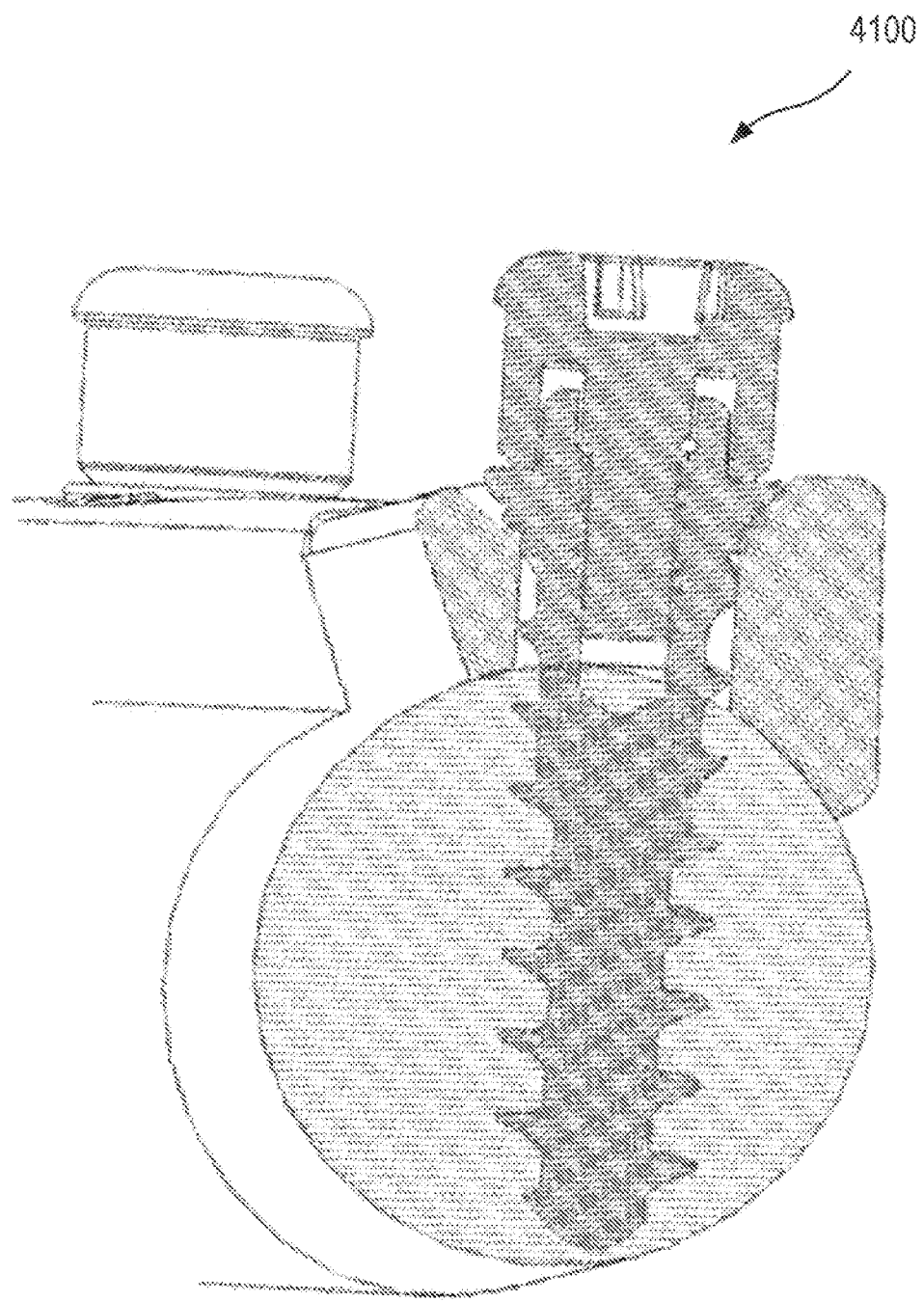
FIG. 41 illustrates aspects of a surgical system, in accordance with some embodiments.
Figure 42:
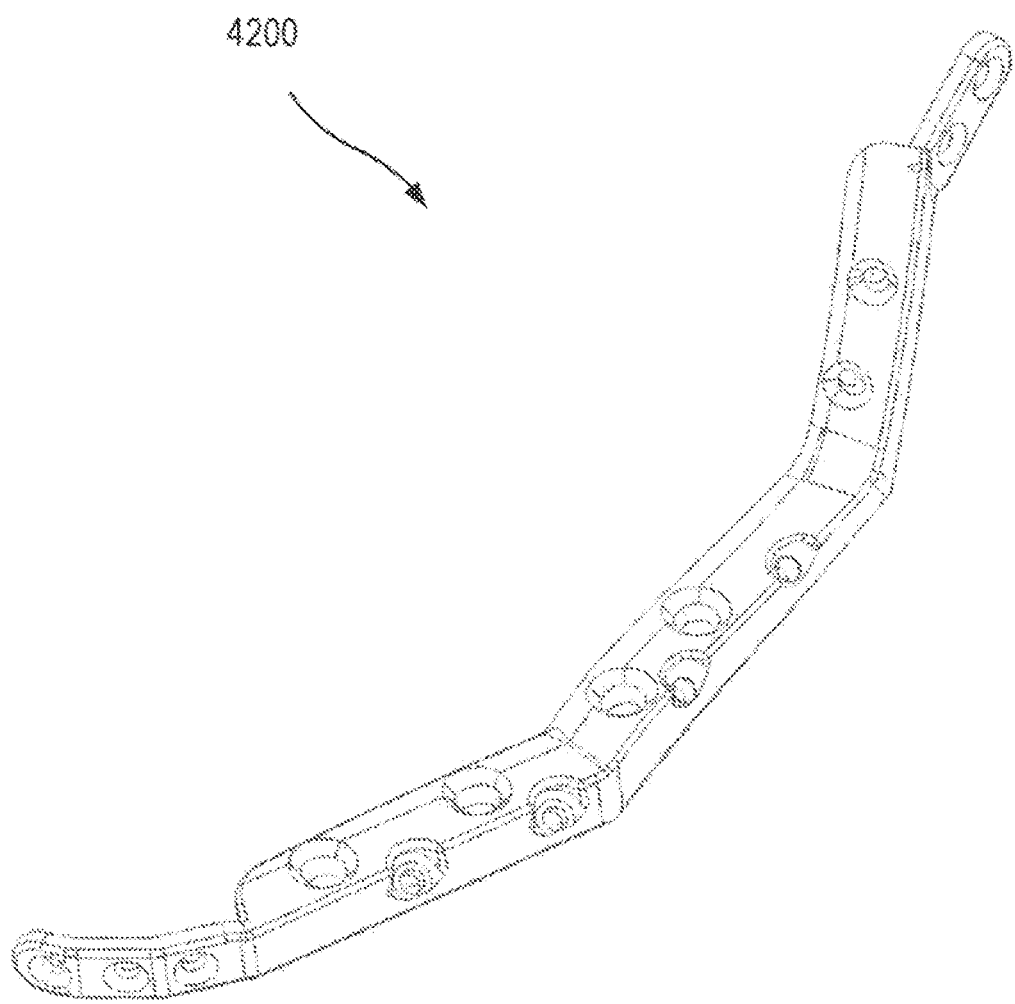
FIG. 42 illustrates aspects of a surgical system, in accordance with some embodiments.

FIG. 40 depicts aspects of a surgical system 4000, according to embodiments of the present invention. As shown here, a system 4000 can include a single row of three fibular grafts 4012, 4014, and 4016 neo-mandibular construct with non-protruding plate and dental implants. FIG. 41 depicts aspects of a surgical system 4100, according to embodiments of the present invention. As shown in this cross-sectional view, a system 4100 can include a single barrel neo-mandible with a non-protruding plate. FIG. 42 depicts aspects of a surgical system 4200, according to embodiments of the present invention. As shown here, a system 4200 can include a non-protruding plate and dental implant locator.

Embodiments of the present invention encompass various techniques for achieving the double barrel conformation. The cutting guide can be fixed to the fibula and the fibula is cut, and the lower and upper rows can come together. This can be accomplished with an all-in-one system design that involves rotation around a hinge. Alternatively, this can be accomplished with a two-part system design that allows the two barrels to move independently.

Figure 43A:
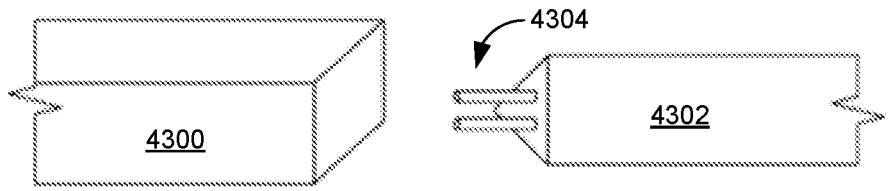
FIGS. 43A-E illustrate "buried fixation" of the neo-mandible to the native mandible according to some embodiments of the disclosed technologies.

FIGS. 43A-E illustrate "buried fixation" of the neo-mandible to the native mandible according to some embodiments of the disclosed technologies. FIG. 43A illustrates the native mandible 4300 and the first section 4302 according to some embodiments of the disclosed technologies. The first section 4302 may include two or more round phalanges 4304 that extend from the first section 4302 towards the native mandible 4300. In the embodiment of FIG. 43A the first section 4302 has a triangular cross-section. In other embodiments the first section 4302 may have cross-sections of other shapes.

Figure 43B:
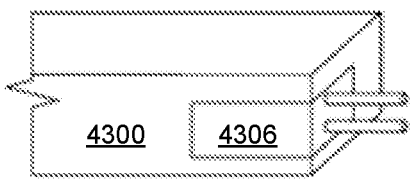

FIG. 43B illustrates the native mandible 4300 with a drill guide 4306 attached according to some embodiments of the disclosed technologies. The drill guide 4306 may be attached to the native mandible 4300 in any manner. For example, the drill guide 4306 may be attached to the native mandible 4300 with one or more screws. The drill guide 4306 may wrap around two surfaces of the native mandible, for example as shown in FIG. 43B. The drill guide 4306 may include two or more tubes to guide the drill to prevent the driller from tilting the drill off axis.

Figure 43C:
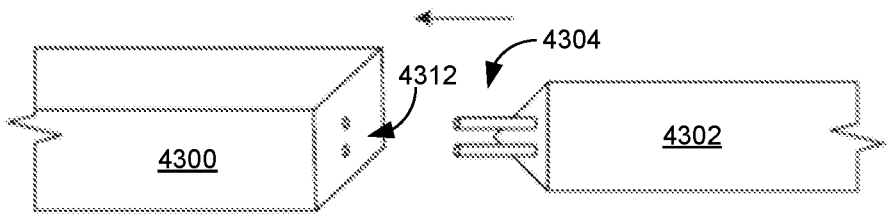

FIG. 43C illustrates the native mandible 4300 and the first section 4302 after drilling holes 4312 in the native mandible 4300 according to some embodiments of the disclosed technologies. After drilling the holes 4312, the native mandible 4300 and the first section 4302 may be joined by inserting the phalanges 4304 into the holes 4312, as shown by the horizontal arrow in FIG. 43C.

Figure 43D:
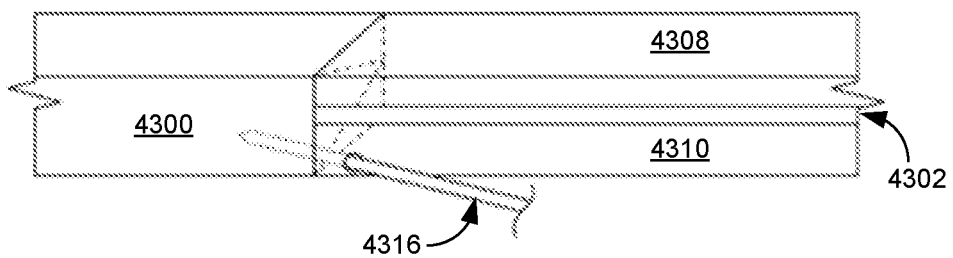

FIG. 43D illustrates the native mandible 4300 after being joined with the first section 4302 according to some embodiments of the disclosed technologies. Also shown attached to the first section 4302 are a first upper bone graft section 4308 and a first lower bone graft section 4310. FIG. 43D also illustrates a K wire 4316 inserted through the first lower bone graft section 4310 and into the native mandible 4300.

Figure 43E:
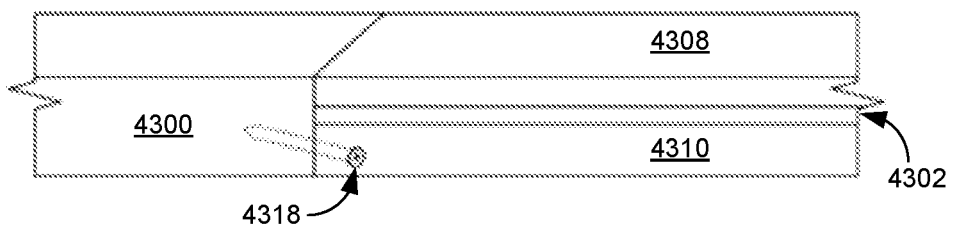

FIG. 43E illustrates the joined native mandible 4300 and first section 4302 with a compression screw 4318 driven over the K wire 4314 in the first lower bone graft section 4310 and into the native mandible 4300 according to some embodiments of the disclosed technologies. In other embodiments, other methods of fixation may be used.

FIGS. 44-48 further illustrate "buried fixation" of the neo-mandible to the native mandible according to some embodiments of the disclosed technologies.

Figure 44:
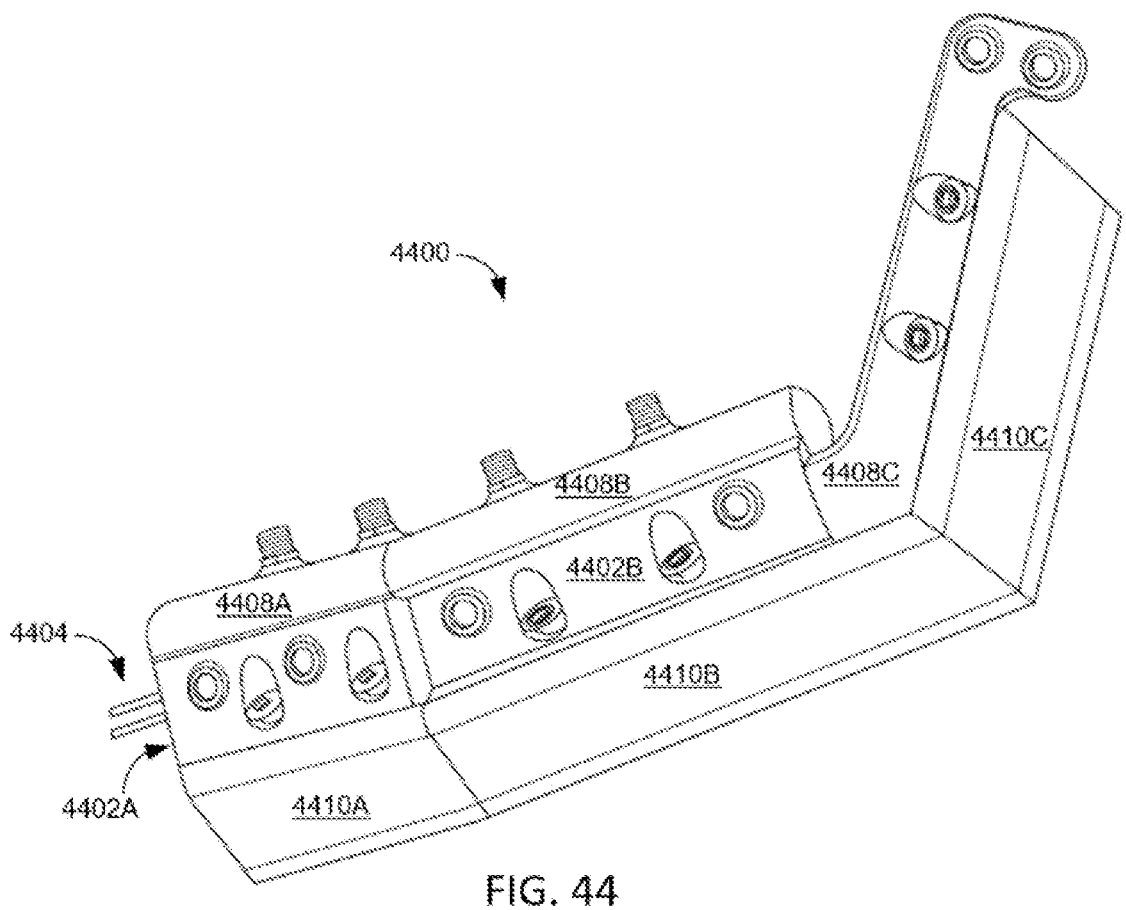
FIGS. 44-48 further illustrate "buried fixation" of the neo-mandible to the native mandible according to some embodiments of the disclosed technologies.

FIG. 44 illustrates a neo-mandible 4400 according to some embodiments of the disclosed technologies. Referring to FIG. 44, the neo-mandible 4400 may include three sections 4402A,B,C. The neo-mandible 4400 may also include upper bone graft sections 4408A,B and lower bone graft sections 4410A,B,C. The upper bone graft sections 4408A,B may be attached to sections 4402A,B, respectively, while the lower bone graft sections 4410A,B,C may be attached to sections 4402A,B,C, respectively. The first section 4402A may include two or more phalanges 4404 for insertion into the native mandible. Other embodiments may have more or fewer sections.

Figure 45:
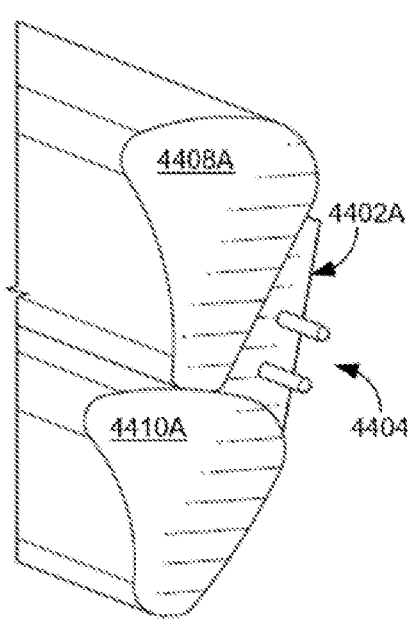

FIG. 45 is a left-side view of the neo-mandible 4400 of FIG. 44 according to some embodiments of the disclosed technologies. Referring to FIG. 45, the first section 4402A, the phalanges 4404, and the first upper and lower bone graft sections 4408A, 4410A are shown.

Figure 46:
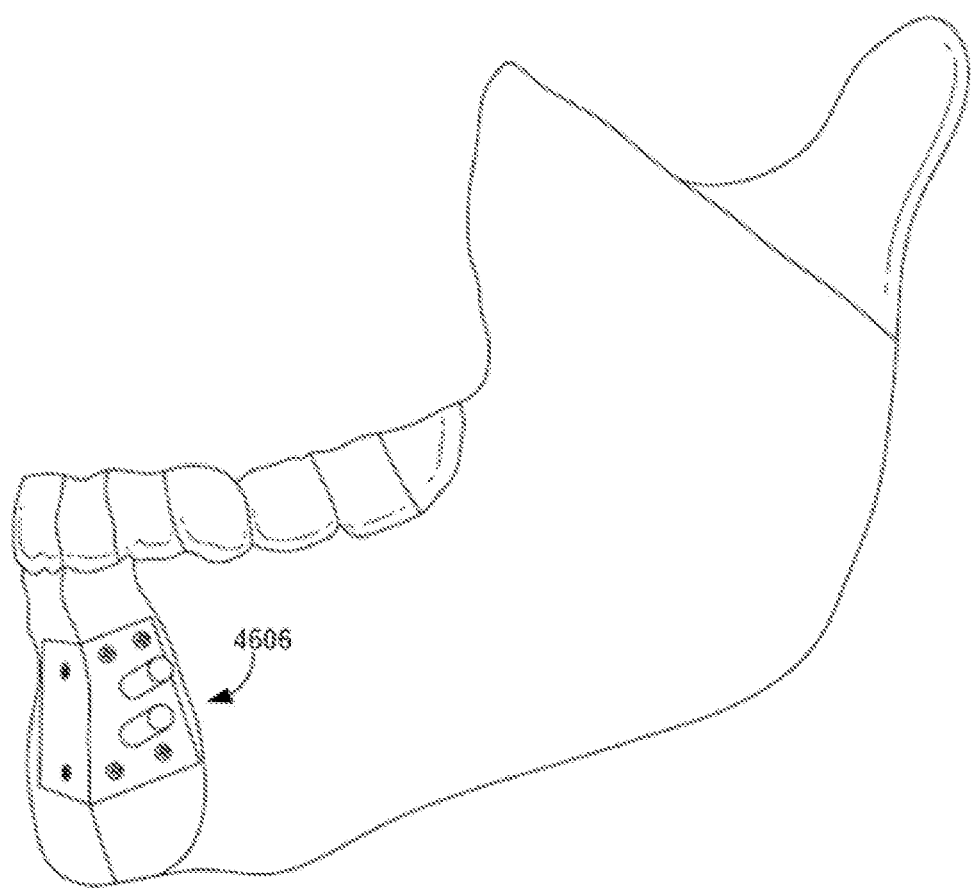

FIG. 46 illustrates the native mandible with a drilling guide 4606 installed according to some embodiments of the disclosed technologies. Fixation may be at least monocortical and thus on the buccal surface of the mandible.

Figure 47:
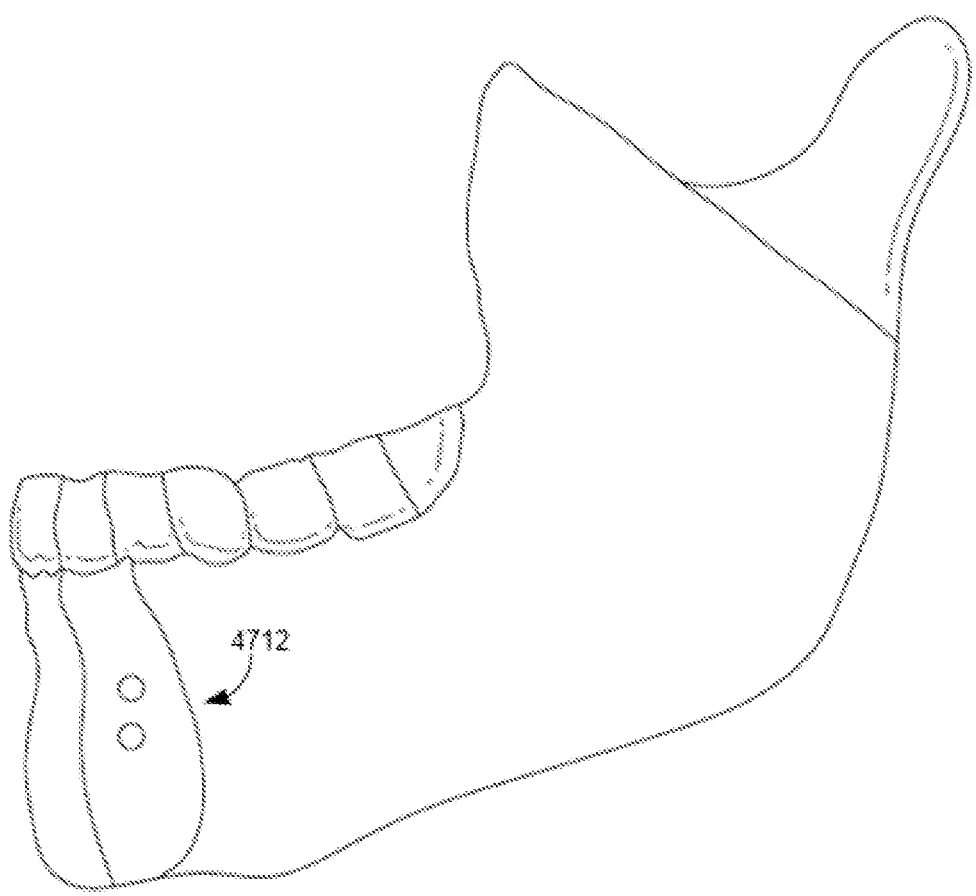

FIG. 47 illustrates the native mandible after drilling holes 4712 in the native mandible using the drilling guide 4606 according to some embodiments of the disclosed technologies.

Figure 48:
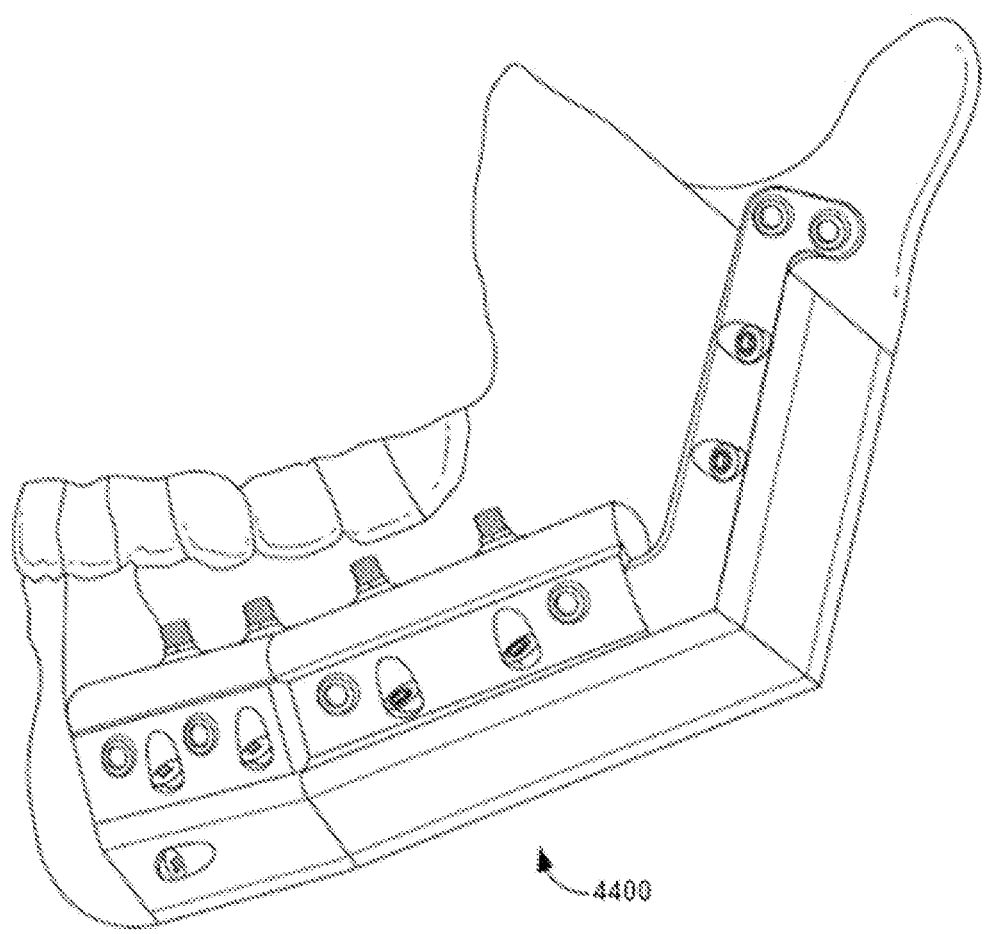

FIG. 48 illustrates the native mandible with the neo-mandible 4400 installed in the native mandible according to some embodiments of the disclosed technologies.

Figure 49:
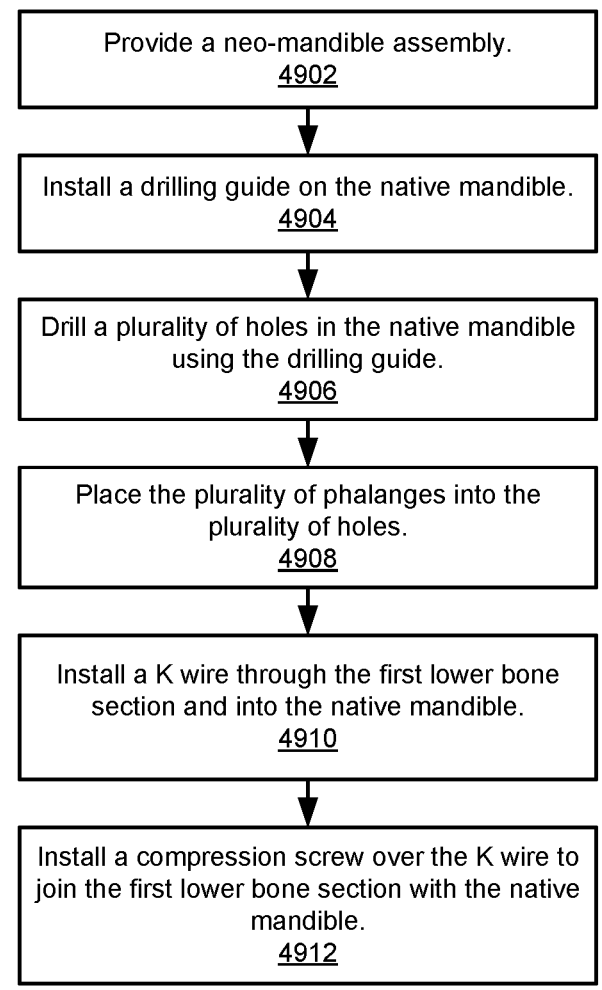
FIG. 49 is a flowchart illustrating a process for implanting a neo-mandible assembly on a mandibular defect region of a patient using buried fixation according to some embodiments of the disclosed technologies.

FIG. 49 is a flowchart illustrating a process 4900 for implanting a neo-mandible assembly on a mandibular defect region of a patient using buried fixation according to some embodiments of the disclosed technologies. The elements of the processes described in this disclosure are presented in one arrangement. However, it should be understood that one or more elements of each process may be performed in a different order, in parallel, omitted entirely, and the like. Furthermore, each process may include other elements in addition to those presented.

Referring to FIG. 49, the process 4900 may include providing a neo-mandible assembly, at 4902. For example, the neo-mandible assembly 4400 of FIG. 44 may be provided. The neo-mandible assembly may include a first section, a first upper bone graft section, a first lower bone graft section, a first upper fixation mechanism that secures the first section with the first upper bone graft section, a first lower fixation mechanism that secures the first section with the first lower bone graft section, and a plurality of phalanges extending from the first section and arranged to mate with corresponding holes in the native mandible, for example as illustrated in FIGS. 43A-E and 44.

Referring again to FIG. 49, the process 4900 may include installing a drilling guide on the native mandible, at 4904. For example, the drilling guide may be as shown in FIGS. 43B and 46 and described with reference thereto.

Referring again to FIG. 49, the process 4900 may include drilling a plurality of holes in the native mandible using the drilling guide, at 4906. For example, the holes may be as shown in FIGS. 43C and 47 and described with reference thereto. Referring again to FIG. 49, the process 4900 may include placing the plurality of phalanges into the plurality of holes, at 4908.

The process 4900 may include installing a K wire through the first lower bone graft section and into the native mandible, at 4910. For example, the K wire may be inserted as shown in FIG. 43D and described with reference thereto.

Referring again to FIG. 49, the process 4900 may include installing a compression screw over the K wire to join the first lower bone section with the native mandible, at 4912. For example, the compression screw may be installed as shown in FIG. 43E and described with reference thereto. In other embodiments, other methods of fixation may be used.

Figure 50A:
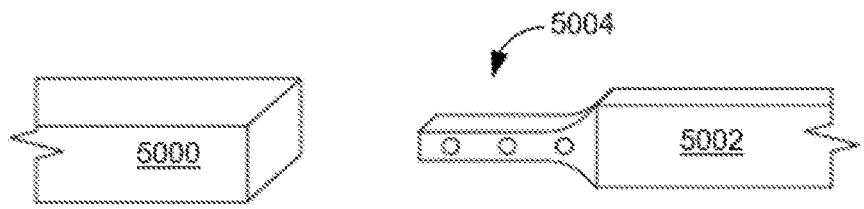
FIGS. 50A-E illustrate "countersunk fixation" of the neo-mandible to the native mandible according to some embodiments of the disclosed technologies.

FIGS. 50A-E illustrate "countersunk fixation" of the neo-mandible to the native mandible according to some embodiments of the disclosed technologies. FIG. 50A illustrates the native mandible 5000 and the first section 5002 according to some embodiments of the disclosed technologies. The first section 5002 may include a phalange 5004 that extend from the first section 5002 towards the native mandible 5000. The phalange 5004 may include a plurality of through-holes as shown. For example, the phalange 5004 may include three or four through-holes, although other numbers of holes may be used instead. In the embodiment of FIG. 50A the first section 5002 has a rectangular cross-section. In other embodiments the first section 5002 may have cross-sections of other shapes.

Figure 50B:
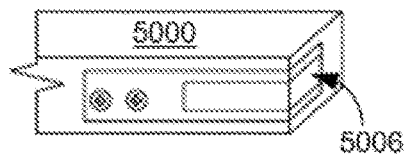

FIG. 50B illustrates the native mandible 5000 with a cutting guide 5006 attached according to some embodiments of the disclosed technologies. The cutting guide 5006 may be attached to the native mandible 5000 in any manner. For example, the cutting guide 5006 may be attached to the native mandible 5000 with two or more screws for torsional stability, as shown. The cutting guide 5006 may wrap around two surfaces of the native mandible, for example as shown in FIG. 50B.

Figure 50C:
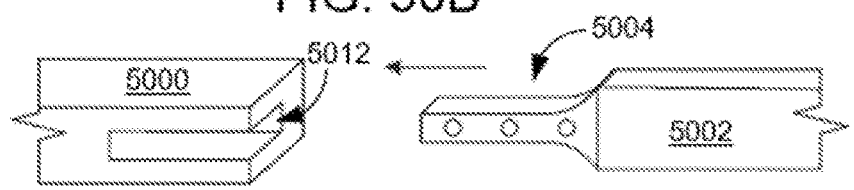

FIG. 50C illustrates the native mandible 5000 and the first section 5002 after cutting a channel 5012 in the native mandible 5000 according to some embodiments of the disclosed technologies. After cutting the channel 5012, the native mandible 5000 and the first section 5002 may be joined by inserting the phalange 5004 into the channel 5012, as shown by the horizontal arrow in FIG. 50C.

Figure 50D:
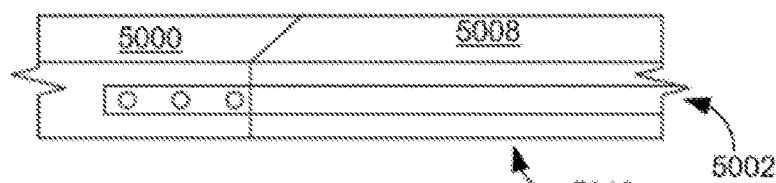

FIG. 50D illustrates the native mandible 5000 after being joined with the first section 5002 according to some embodiments of the disclosed technologies. Also shown attached to the first section 5002 are a first upper bone graft section 5008 and a first lower bone graft section 5010.

Figure 50E:
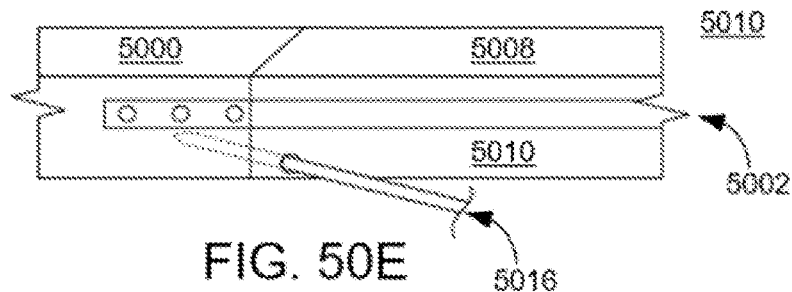
Figure 50F:
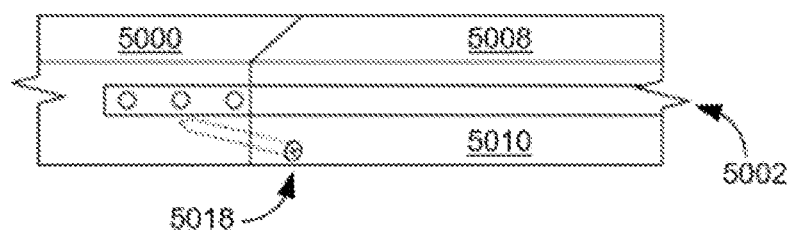
FIG. 50F illustrates the joined native mandible and first section with a compression screw driven over the K wire through the first lower bone graft section and into the native mandible according to some embodiments of the disclosed technologies.

FIG. 50E illustrates a K wire 5016 inserted through the first lower bone graft section 5010 and into the native mandible 5000 according to some embodiments of the disclosed technologies. FIG. 50F illustrates the joined native mandible 5000 and first section 5002 with a compression screw 5018 driven over the K wire in the first lower bone graft section 5010 and into the native mandible 5000 according to some embodiments of the disclosed technologies.

FIGS. 51-54 further illustrate "countersunk fixation" of the neo-mandible to the native mandible according to some embodiments of the disclosed technologies.

Figure 51:
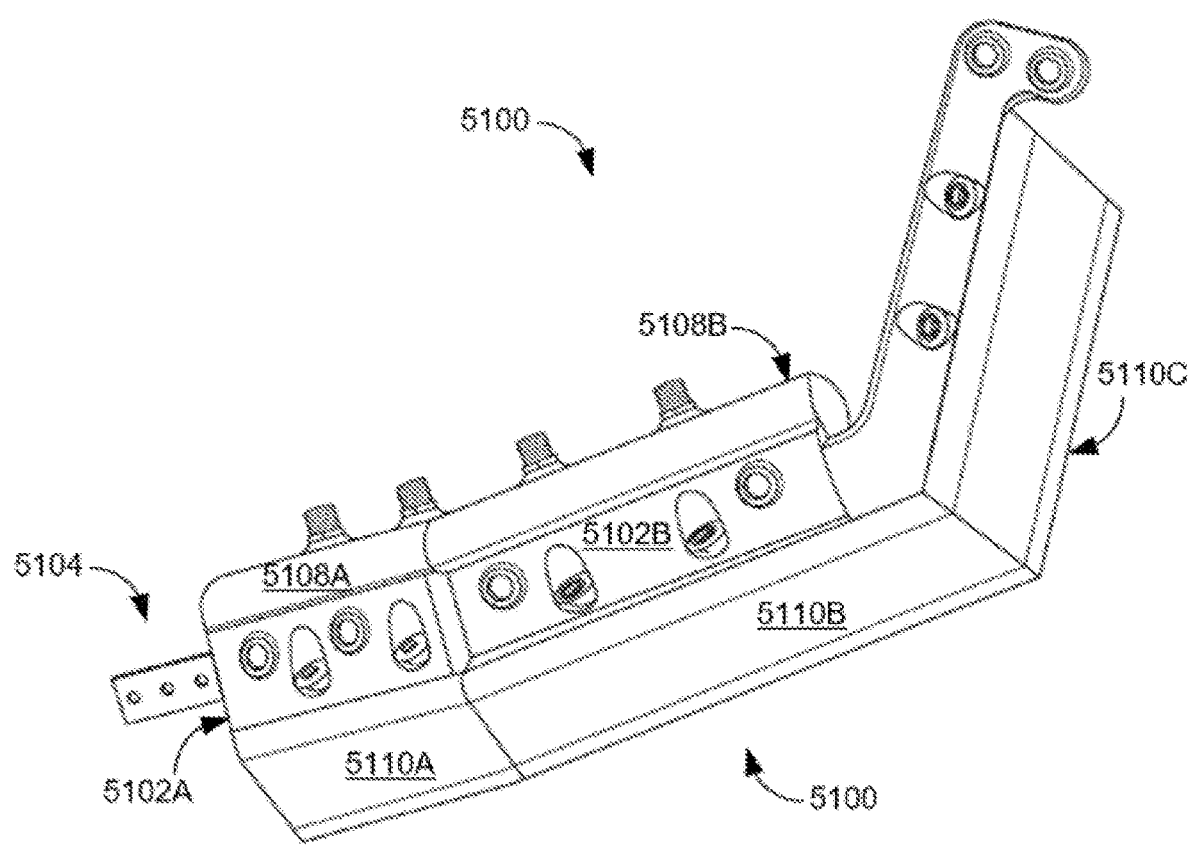
FIGS. 51-54 further illustrate "countersunk fixation" of the neo-mandible to the native mandible according to some embodiments of the disclosed technologies.

FIG. 51 illustrates a neo-mandible 5100 according to some embodiments of the disclosed technologies. Referring to FIG. 51, the neo-mandible 5100 may include three sections 5102A,B,C. The neo-mandible 5100 may also include upper bone graft sections 5108A,B and lower bone graft sections 5110A,B,C. The upper bone graft sections 5108A,B may be attached to sections 5102A,B, respectively, while the lower bone graft sections 5110A,B,C may be attached to sections 5102A,B,C, respectively. The first section 5102A may include a phalange 5104 for insertion into the native mandible.

Figure 52:
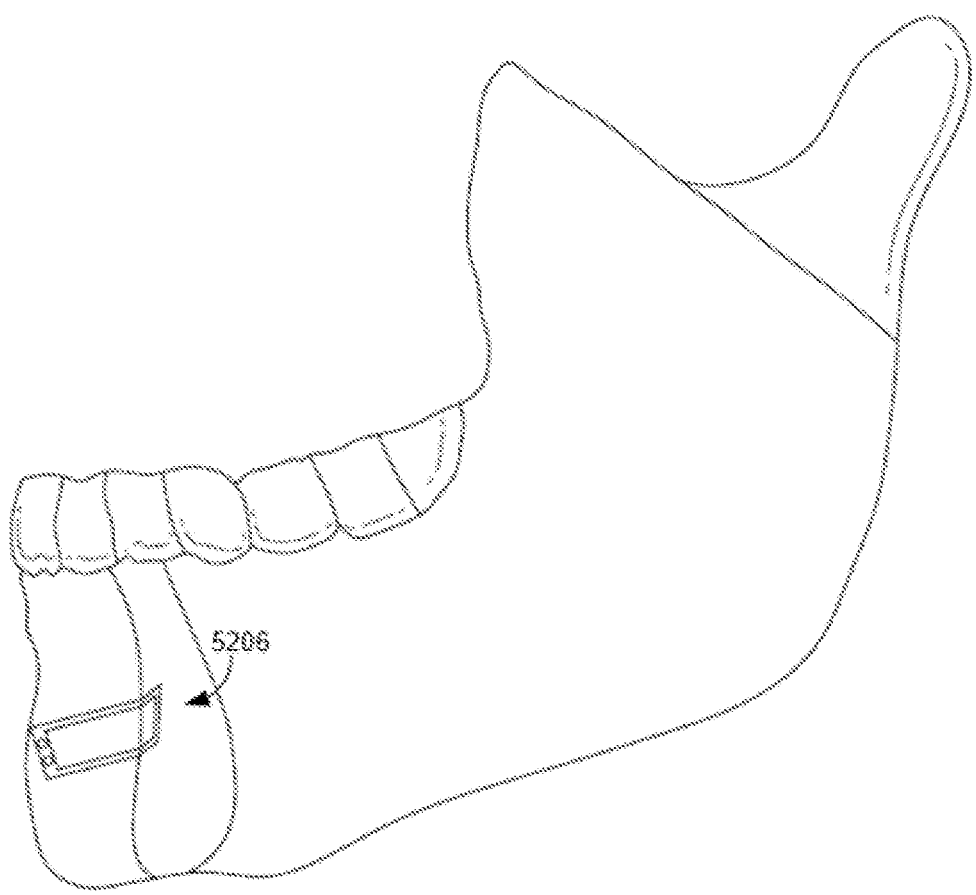

FIG. 52 illustrates the native mandible with a cutting guide 5206 installed according to some embodiments of the disclosed technologies. Referring to FIG. 52, the cutting guide 5206 may be held to the native mandible with two or more screws.

Figure 53:
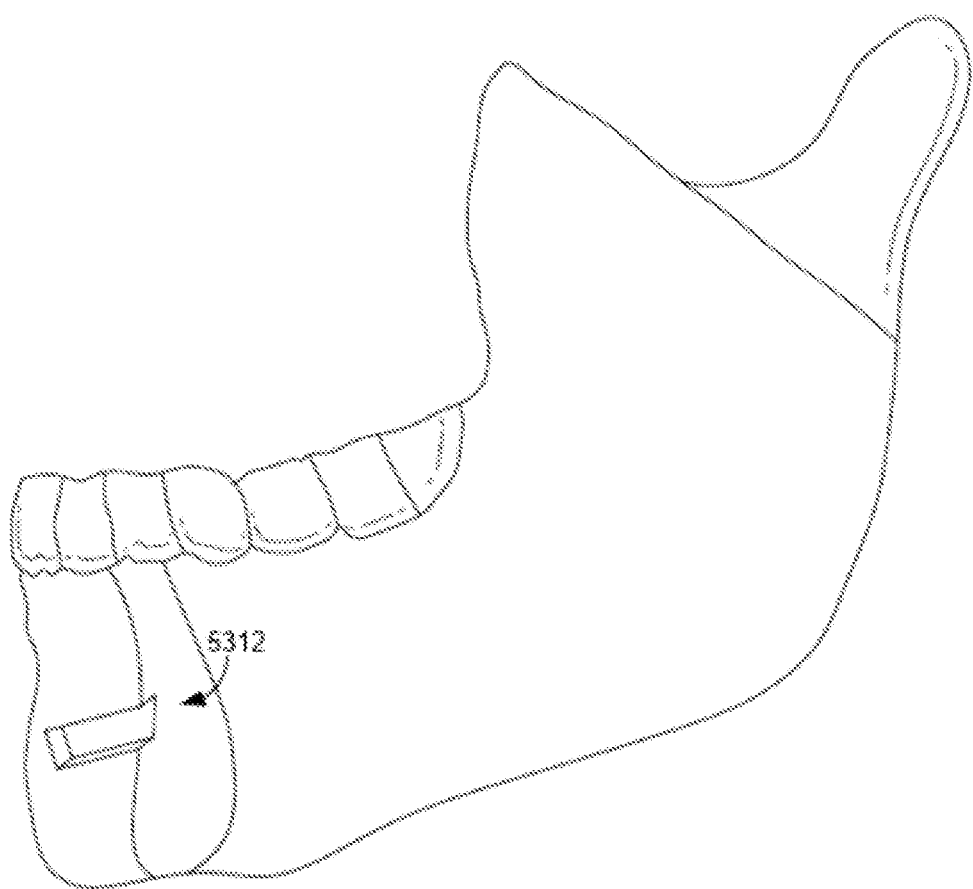

FIG. 53 illustrates the native mandible after cutting a channel 5312 in the native mandible according to some embodiments of the disclosed technologies.

Figure 54:
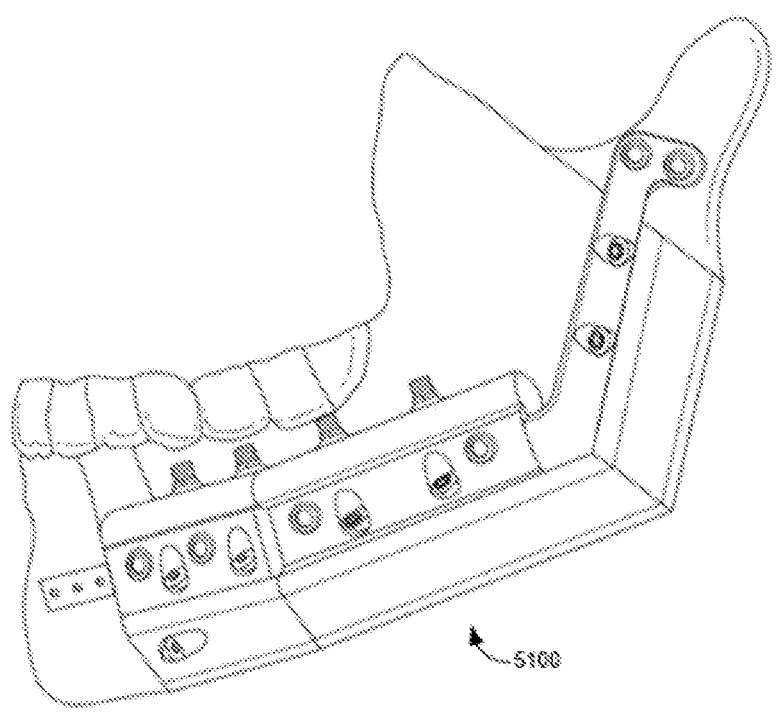

FIG. 54 illustrates the native mandible with the neo-mandible 5100 installed in the native mandible using the cutting guide 5206 according to some embodiments of the disclosed technologies.

Figure 55:
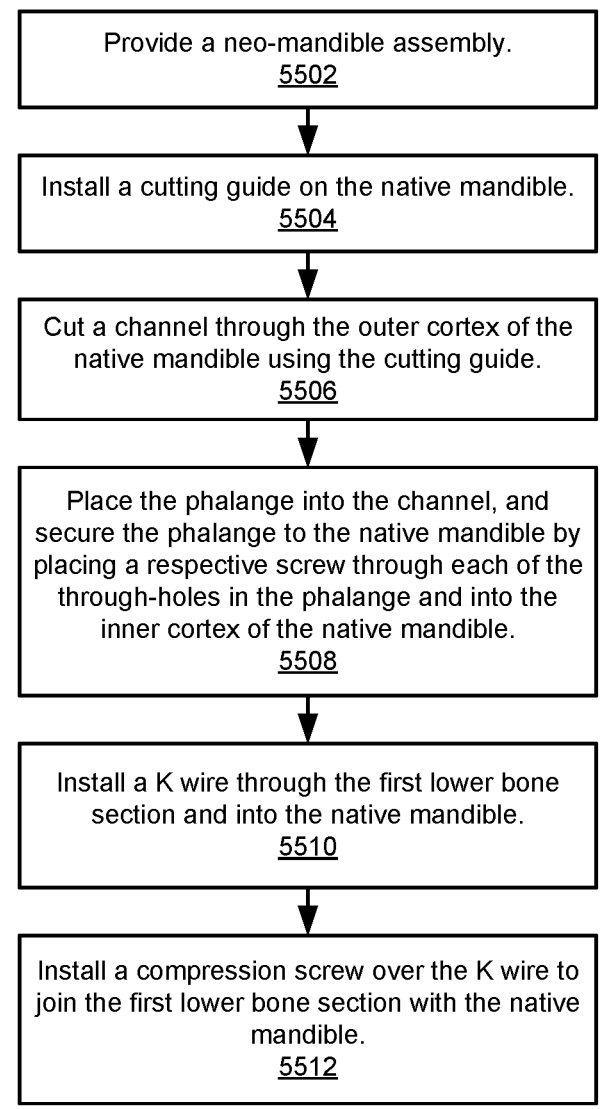
FIG. 55 is a flowchart illustrating a process for implanting a neo-mandible assembly on a mandibular defect region of a patient using countersunk fixation according to some embodiments of the disclosed technologies.

FIG. 55 is a flowchart illustrating a process 5500 for implanting a neo-mandible assembly on a mandibular defect region of a patient using countersunk fixation according to some embodiments of the disclosed technologies.

Referring to FIG. 55, the process 5500 may include providing a neo-mandible assembly, at 5502. For example, the neo-mandible assembly 5100 of FIG. 51 may be provided. The neo-mandible assembly may include a first section, a first upper bone graft section, a first lower bone graft section, a first upper fixation mechanism that secures the first section with the first upper bone graft section, a first lower fixation mechanism that secures the first section with the first lower bone graft section, and a phalange extending from the first section and arranged to mate with a corresponding channel in the native mandible. The phalange may have at least one through-hole, and preferably three or more, for example as illustrated in FIGS. 43A-E.

Referring again to FIG. 55, the process 5500 may include installing a cutting guide on the native mandible, at 5504. For example, the cutting guide may be as shown in FIGS. 50B and 52 and described with reference thereto.

Referring again to FIG. 55, the process 5500 may include cutting a channel through the outer cortex of the native mandible using the cutting guide, at 5506. For example, the channel may be as shown in FIGS. 50C and 53 and described with reference thereto. Referring again to FIG. 55, the process 5500 may include placing the phalange into the channel, and securing the phalange to the native mandible by placing a respective screw through each of the through-holes in the phalange and into the inner cortex of the native mandible, at 5508.

The process 5500 may include installing a K wire through the first lower bone section and into the native mandible, at 5510. For example, the K wire may be inserted as shown in FIG. 50E and described with reference thereto.

Referring again to FIG. 55, the process 5500 may include installing a compression screw over the K wire to join the first lower bone section with the native mandible, at 5512. For example, the compression screw may be installed as shown in FIG. 50F and described with reference thereto. In other embodiments, other methods of fixation may be used.

Embodiments of the present invention encompass kits having mandibular reconstruction system as disclosed herein. In some embodiments, the kit includes one or more mandibular reconstruction system components, along with instructions for using the device(s) for example according to any of the methods disclosed herein.

All features of the described systems and devices are applicable to the described methods *mutatis mutandis*, and vice versa.

FIGS. 56-63 illustrate a single-barrel mandibular reconstruction technique utilizing a temporary fixation plate according to some embodiments of the disclosed technologies. Features of these embodiments may be combined with features of other embodiments described herein.

Figure 56:
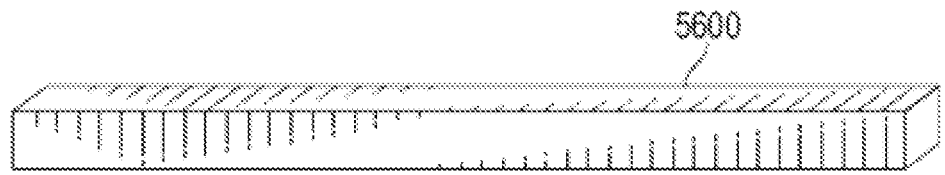
FIGS. 56-63 illustrate a single-barrel mandibular reconstruction technique utilizing a temporary fixation plate according to some embodiments of the disclosed technologies.

FIG. 56 illustrates a section of native bone 5600. For example, the bone may be a fibula.

Figure 57:
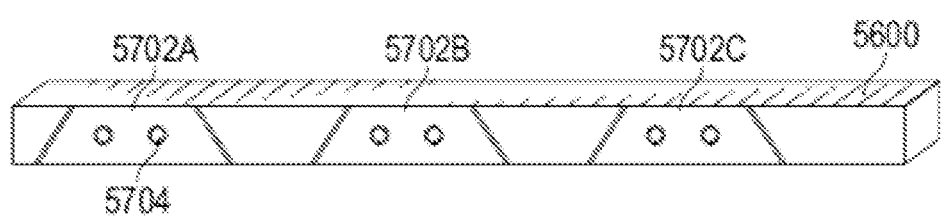

FIG. 57 illustrates the native fibula section 5600 with bone graft sections 5702A, 5702B, and 5702C marked, according to some embodiments of the disclosed technology. At this point a cutting guide (not shown) may be attached to the bone graft sections 5702 using temporary fixation screws 5704. As described above, the cutting guide may have multiple sections, which may be joined by hinges or other devices, or not joined at all. For example, the hinged cutting guide may be the hinged cutting guide 1100 of FIG. 11 or the hinged cutting guides 1300A and 1300B of FIGS. 13A and 13B.

Figure 58:
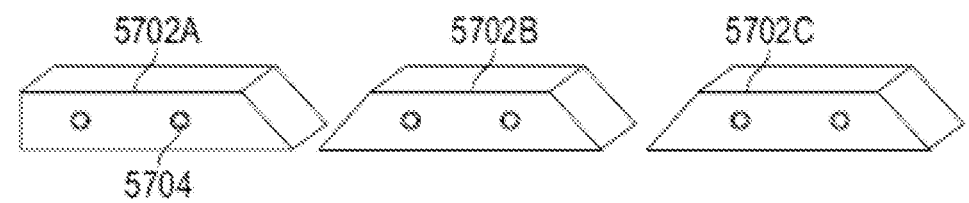

FIG. 58 illustrates the bone graft sections 5702A, 5702B, and 5702C after being cut from the native fibula section 5600, according to some embodiments of the disclosed technology.

Figure 59:
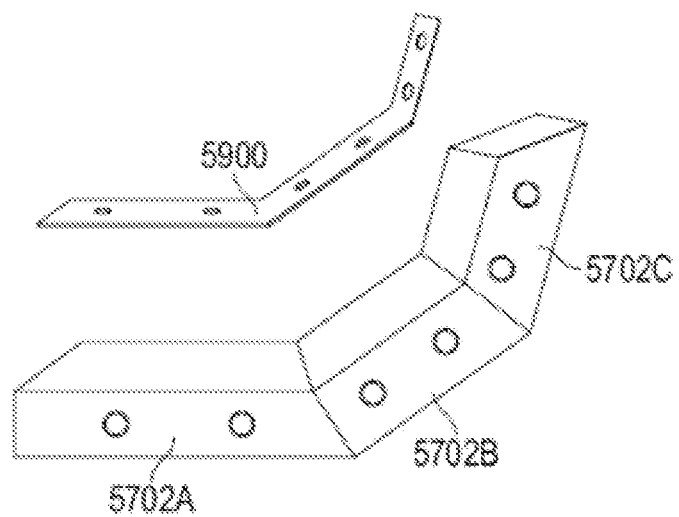

FIG. 59 illustrates the bone graft sections 5702A, 5702B, and 5702C arranged in a neo-mandible position, as well as a temporary fixation plate 5900 configured to hold the bone graft sections 5702 in the neo-mandible position, according to some embodiments of the disclosed technology. The temporary fixation plate 5900 is specific to the patient, and may be made by 3D printing or similar techniques.

Figure 60:
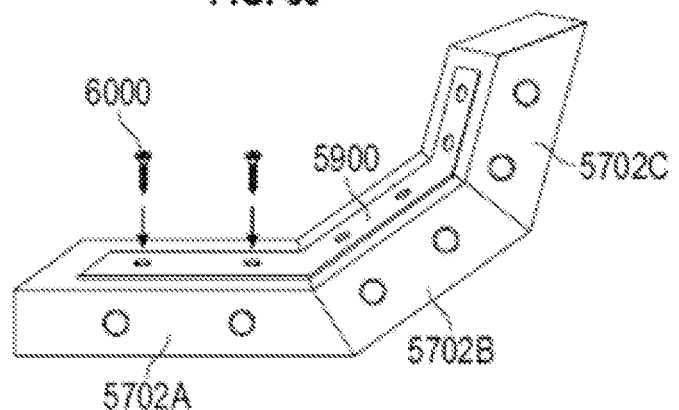

FIG. 60 illustrates the temporary fixation plate 5900 being attached to the bone graft sections 5702A, 5702B, and 5702C using screws 6000, according to some embodiments of the disclosed technology. In the drawings, the temporary fixation plate is attached to cephalic surfaces of the multiple bone graft sections. However, other surfaces of the multiple bone graft sections may be used. In the drawings, two screws 6000 are used for each bone graft section 5700. However, other numbers of screws 6000 may be used. The screws 6000 may be mono-cortical fixation screws.

Figure 61:
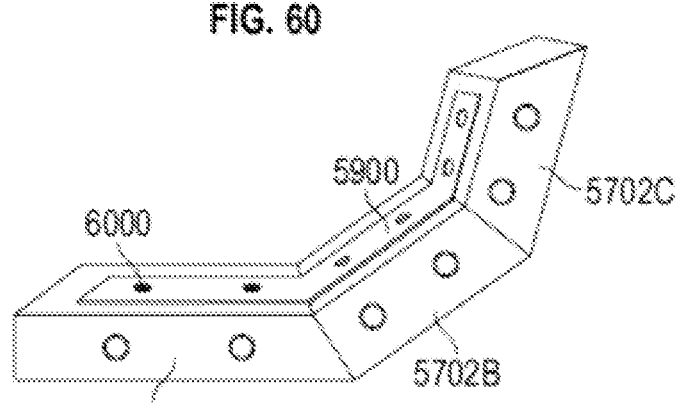

FIG. 61 illustrates the bone graft sections 5702A, 5702B, and 5702C with the temporary fixation plate 5900 attached, according to some embodiments of the disclosed technology. The bone graft sections 5702 are now held in place by the temporary fixation plate 5900. At this point, the multiple bone graft sections are attached to both the temporary fixation plate 5900 and the cutting guide. At this point the cutting guide may be removed.

Figure 62:
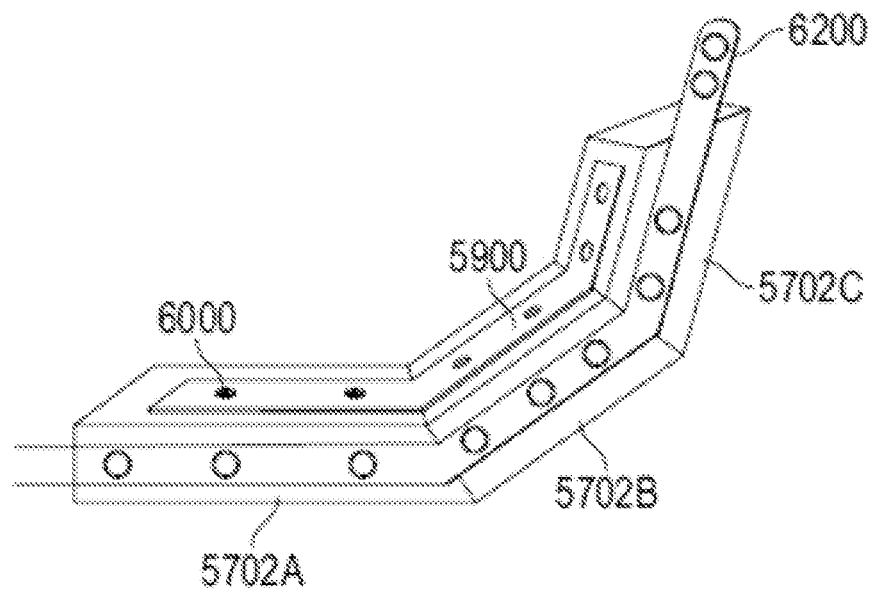

FIG. 62 illustrates the bone graft sections 5702A, 5702B, and 5702C with the temporary fixation plate 5900 attached using screws 6000, and with the final fixation plate 6200 attached, for example using screws, according to some embodiments of the disclosed technology. At this point, the multiple bone graft sections are attached to both the temporary fixation plate 5900 and the final fixation plate 6200.

Figure 63:
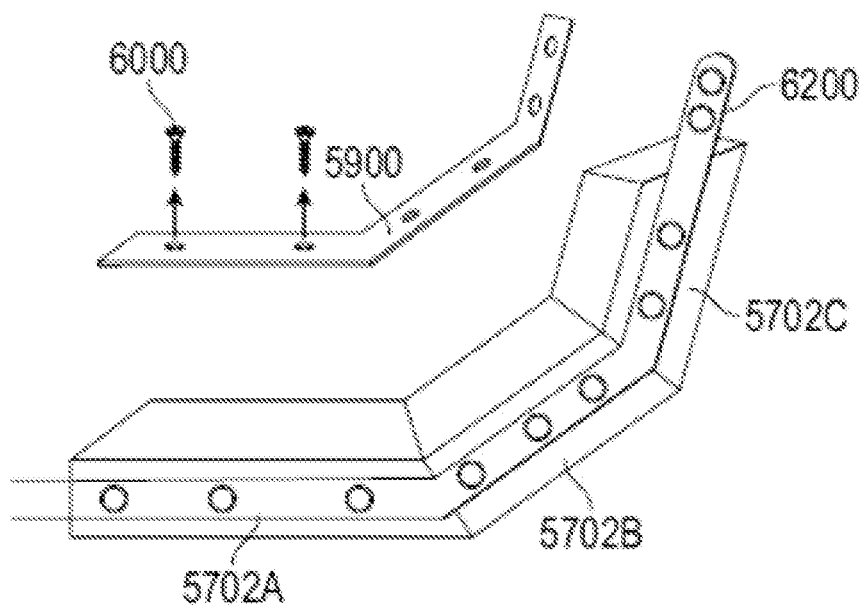

FIG. 63 illustrates removal of the temporary fixation plate 5900 and screws 6000 from bone graft sections 5702A, 5702B, and 5702C, according to some embodiments of the disclosed technology. The bone graft sections 5702 are now held in place by the final fixation plate 6200.

Figure 64:
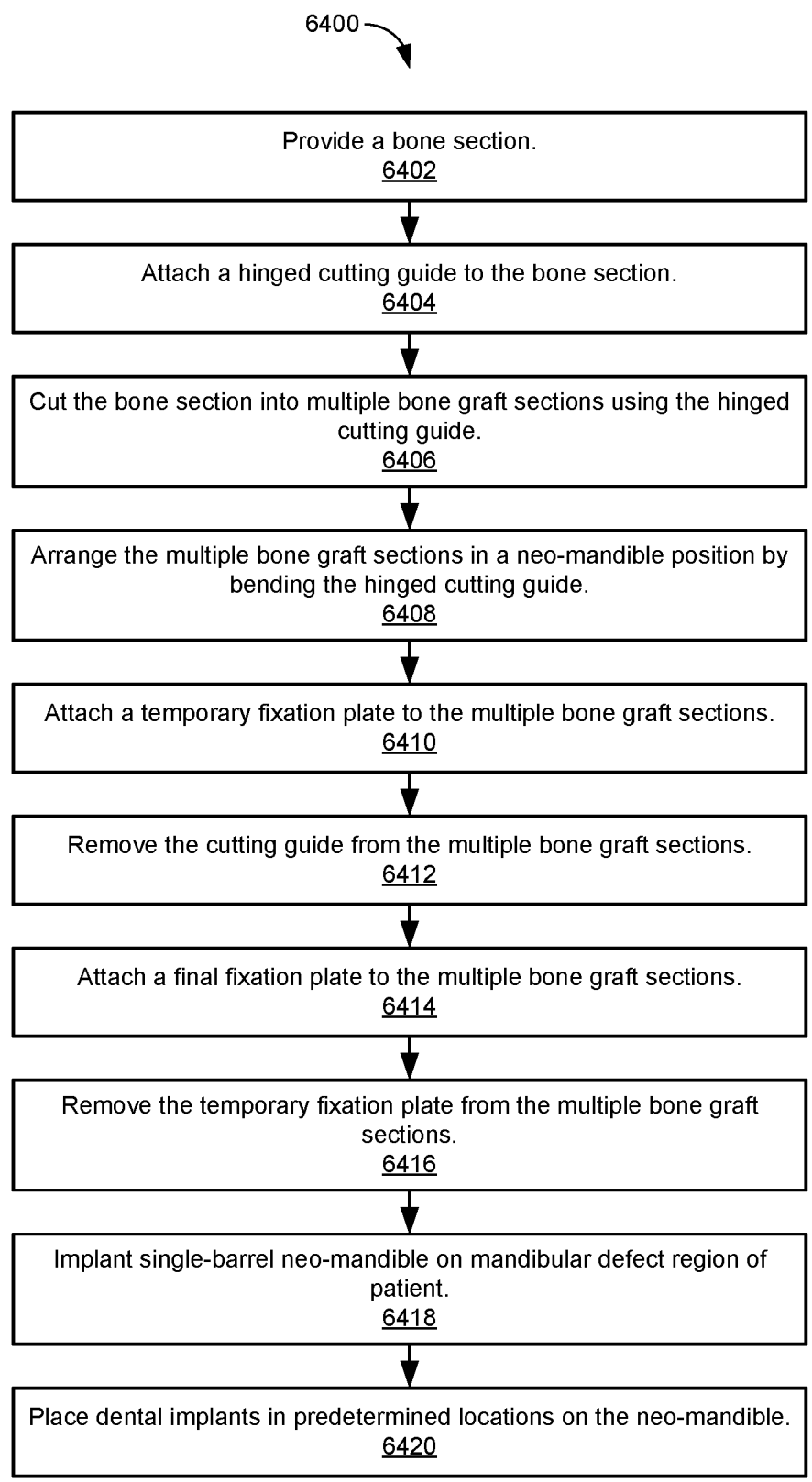
FIG. 64 is a flowchart illustrating a process for constructing a neo-mandible assembly according to some embodiments of the disclosed technologies.

FIG. 64 is a flowchart illustrating a process 6400 for constructing a neo-mandible assembly according to some embodiments of the disclosed technologies. The elements of the processes described in this disclosure are presented in one arrangement. However, it should be understood that one or more elements of each process may be performed in a different order, in parallel, omitted entirely, and the like. Furthermore, each process may include other elements in addition to those presented.

Referring to FIG. 64, the process 6400 may include providing a bone section, at 6402. For example, the bone section may be the bone section 5600 of FIG. 56.

Referring again to FIG. 64, the process 6400 may include attaching a cutting guide to the bone section, at 6404. For example, the cutting guide may be the hinged cutting guide 1100 of FIG. 11 or the hinged cutting guides 1300A and 1300B of FIGS. 13A and 13B. In some embodiments, the sections of the cutting guide may not be joined at all.

Referring again to FIG. 64, the process 6400 may include cutting the bone section into multiple bone graft sections using the cutting guide, at 6406. For example, the multiple bone graft sections may be as shown in FIG. 58.

Referring again to FIG. 64, the process 6400 may include arranging the multiple bone graft sections in a neo-mandible position by bending the cutting guide, at 6408. For example, the multiple bone graft sections may be arranged as shown in FIG. 59.

Referring again to FIG. 64, the process 6400 may include attaching a temporary fixation plate to the multiple bone graft sections, at 6410. For example, the multiple bone graft sections may be as shown in FIG. 58. For example, the temporary fixation plate may be attached to the multiple bone graft sections as shown in FIGS. 59-61.

Referring again to FIG. 64, the process 6400 may include removing the cutting guide from the multiple bone graft sections, at 6412.

The process 6400 may include attaching a final fixation plate to the multiple bone graft sections, at 6414. For example, the final fixation plate may be attached to the multiple bone graft sections as shown in FIG. 62.

Referring again to FIG. 64, the process 6400 may include removing the temporary fixation plate from the multiple bone graft sections, at 6416 to create a single-barrel neo-mandible. The process 6400 may include implanting the single-barrel neo-mandible on a mandibular defect region of a patient, at 6418. The process 6400 may include placing dental implants in predetermined locations on the neo-mandible, at 6420. The dental implants may be commercially-available dental implants. FIGS. 65-69 illustrate a double-barrel mandibular reconstruction technique utilizing temporary fixation plates according to some embodiments of the disclosed technologies. Features of these embodiments may be combined with features of other embodiments described herein.

The technique may begin with a section of native bone, for example as illustrated in FIG. 56. For example, the bone may be a fibula.

A cutting guide may be attached to the bone graft sections using temporary fixation screws, for example as described with respect to FIG. 57. While illustrated and described for a single-barrel neo-mandible, this technique may be used to establish both barrels of a double-barrel neo-mandible through the use of one or more cutting guides. Each barrel may include multiple bone graft sections after being cut from the native fibula section, for example as illustrated and described with reference to FIG. 58.

Figure 65:
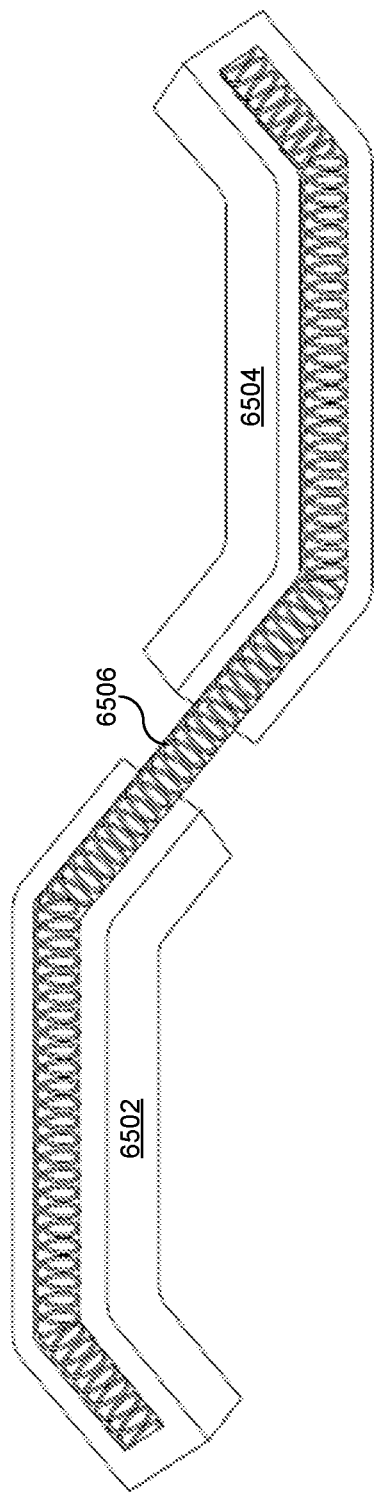

FIG. 65 illustrates hinged cutting guides bent to arrange the bone graft sections in an upper neo-mandible position and a lower neo-mandible position, according to some embodiments of the disclosed technology. Referring to FIG. 65, bone graft sections 6502 are shown arranged in a lower neo-mandible position and bone graft sections 6504 are shown arranged in an upper neo-mandible position are shown, along with a hinged cutting guide 6506.

FIG. 66 illustrates temporary fixation plates being attached to the bone graft sections, according to some embodiments of the disclosed technology. During this process, the cutting guide (not shown) is still attached. Referring to FIG. 66, a lower temporary fixation plate 6602 may be attached to the bone graft sections 6502 arranged in the lower neo-mandible position, and an upper temporary fixation plate 6604 may be attached to the bone graft sections 6504 arranged in the upper neo-mandible position. In some embodiments, the temporary fixation plates 6602, 6604 may be attached to cephalic surfaces of the bone graft sections using screws 6606. However, other surfaces of the multiple bone graft sections may be used. The screws 6606 may be mono-cortical fixation screws. The temporary fixation plates 6602, 6604 may be specific to the patient, and may be made by 3D printing or similar techniques.

Figure 67:
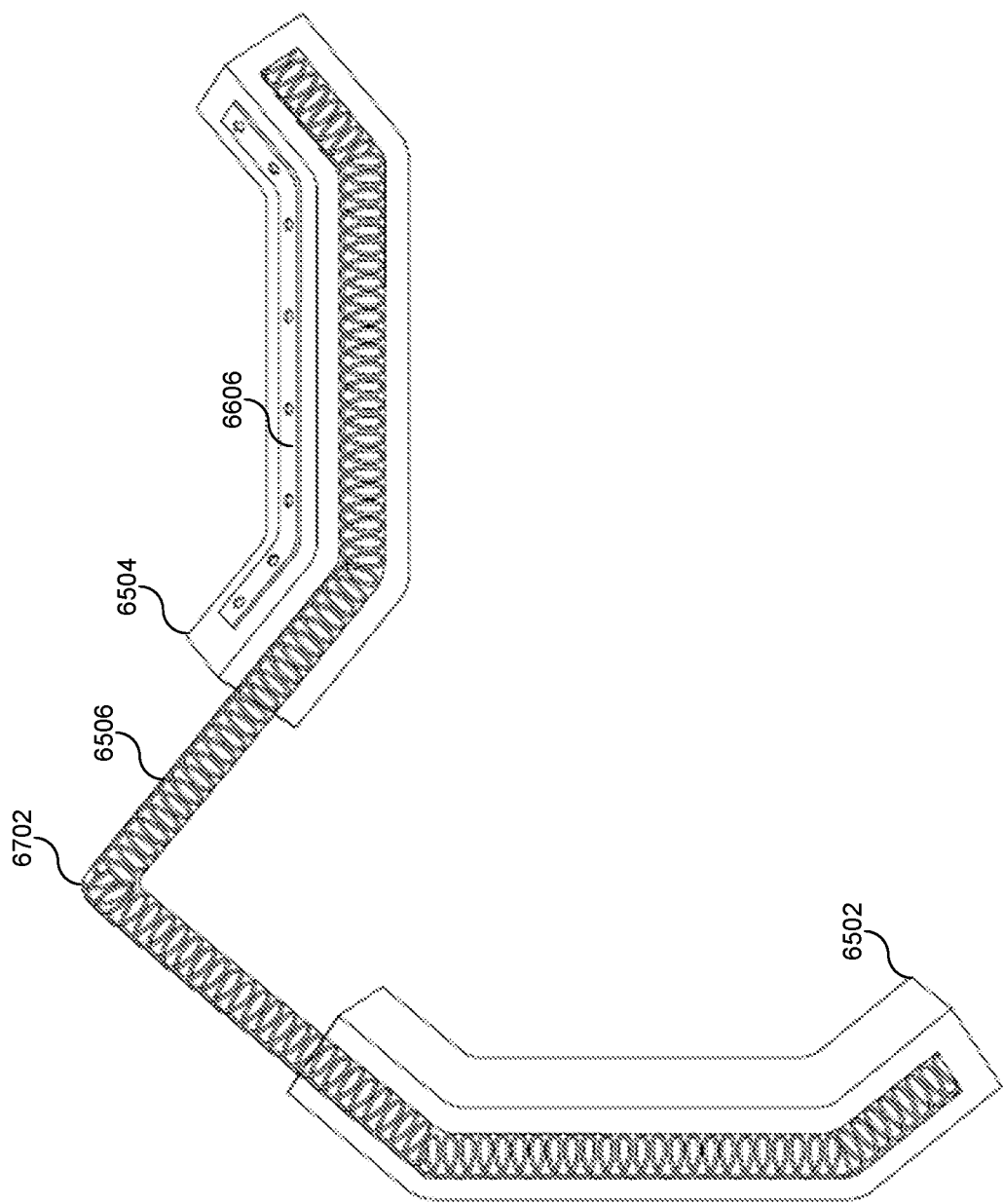

FIG. 67 illustrates bending the hinged cutting guide 6506 to align the bone graft sections 6502 arranged in the upper neo-mandible position with the bone graft sections 6504 arranged in the lower neo-mandible position, according to some embodiments of the disclosed technology. In this embodiment, the cutting guide is also hinged between the upper and lower sections, at 6702. During the process, the temporary fixation plates 6502, 6504 remain attached.

In other embodiments, two separate hinged cutting guides may be used: one for the upper neo-mandible and another for the lower neo-mandible. After cutting the native bone sections, each hinged cutting guide may be bent at the hinges to form the respective neo-mandible. Once bent, cutting/alignment guide springs may be attached to the hinged cutting guides to keep them bent in the proper position. The cutting/alignment guide springs may be as shown in, and described with respect to, FIGS. 13A and 13B. After the holes for the jaw plate 6802 have been drilled using the hinged cutting guides (with the cutting/alignment guide springs attached), the upper and lower neo-mandibles may be manually aligned for installation of the jaw plate 6802 using the holes.

Figure 68:
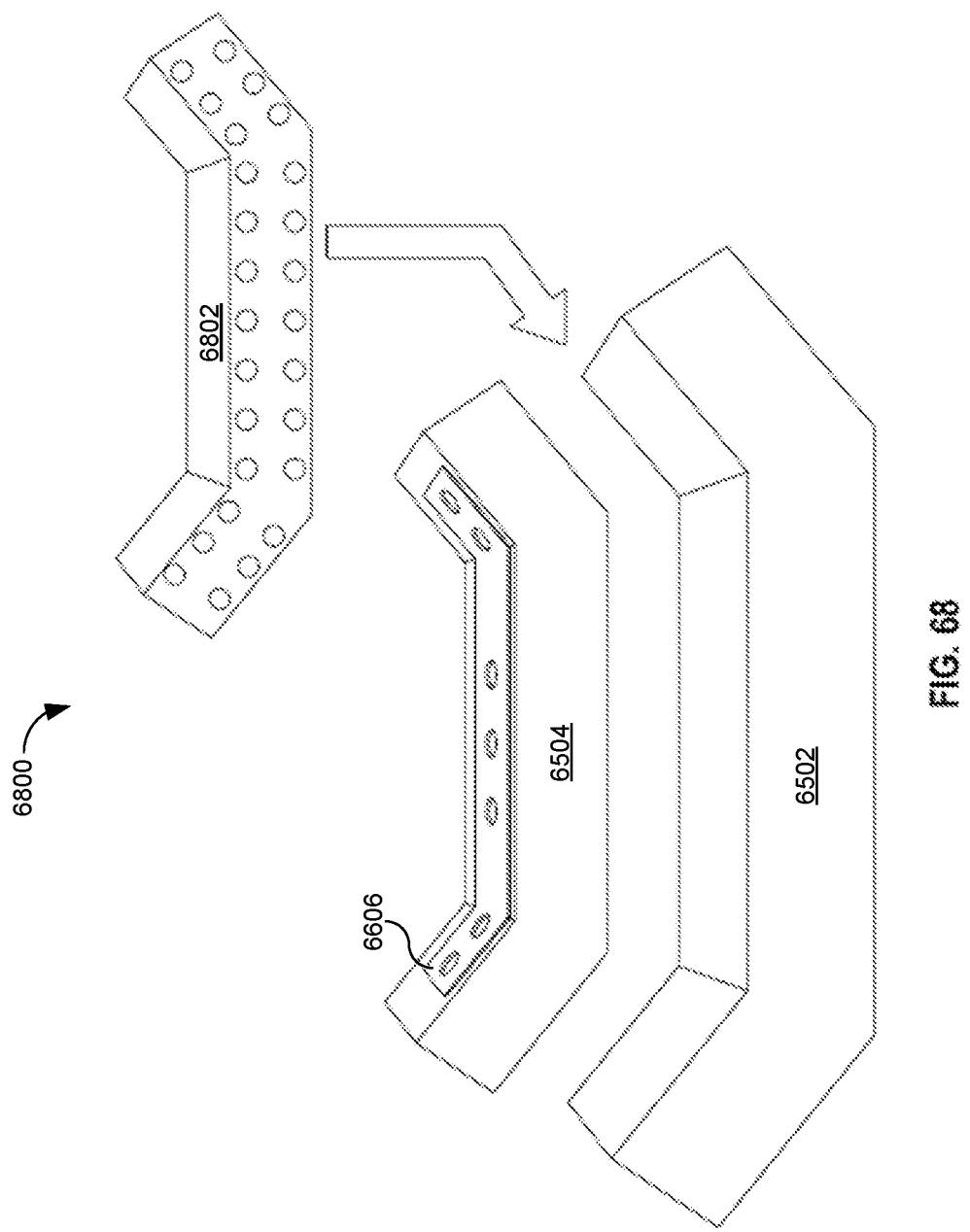

FIG. 68 illustrates attaching a jaw plate 6802 between the bone graft sections 6504 arranged in the upper neo-mandible position and the bone graft sections 6502 arranged in the lower neo-mandible position to create a double-barrel neo-mandible 6800, according to some embodiments of the disclosed technology. At this point, the multiple bone graft sections are attached to the temporary fixation plates 6502, 6504 and the jaw plate 6802. In this embodiment, the hinged cutting guide 6506 may be removed before attaching the jaw plate 6802.

In other embodiments, the jaw plate may be attached while the cutting guide is attached. After attaching the jaw plate, the cutting guide may be removed. In these embodiments, the temporary fixation plates are not needed.

Figure 69:
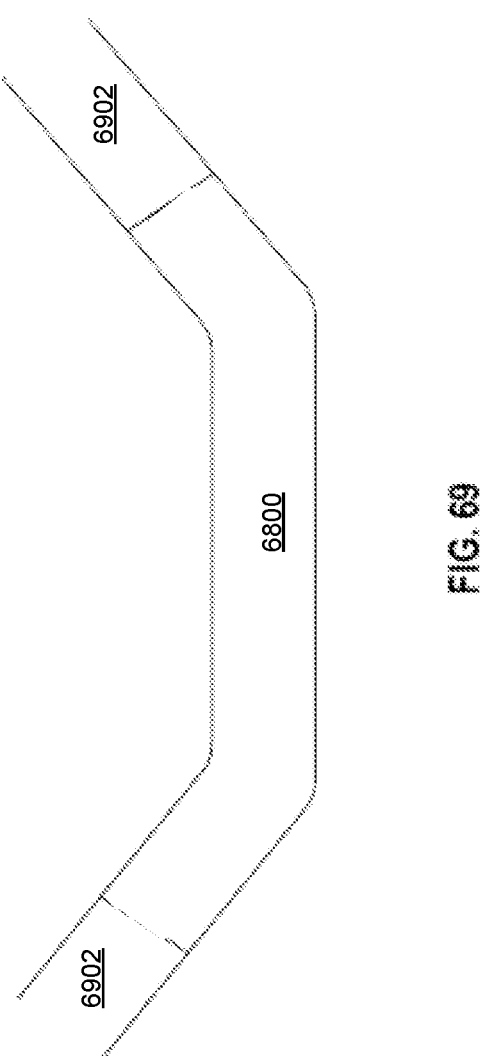

FIG. 69 illustrates the double-barrel neo-mandible 6800 of FIG. 68 attached to a native mandible 6902, according to some embodiments of the disclosed technology. Any attachment process may be used, for example including those described elsewhere herein.

Figure 70:
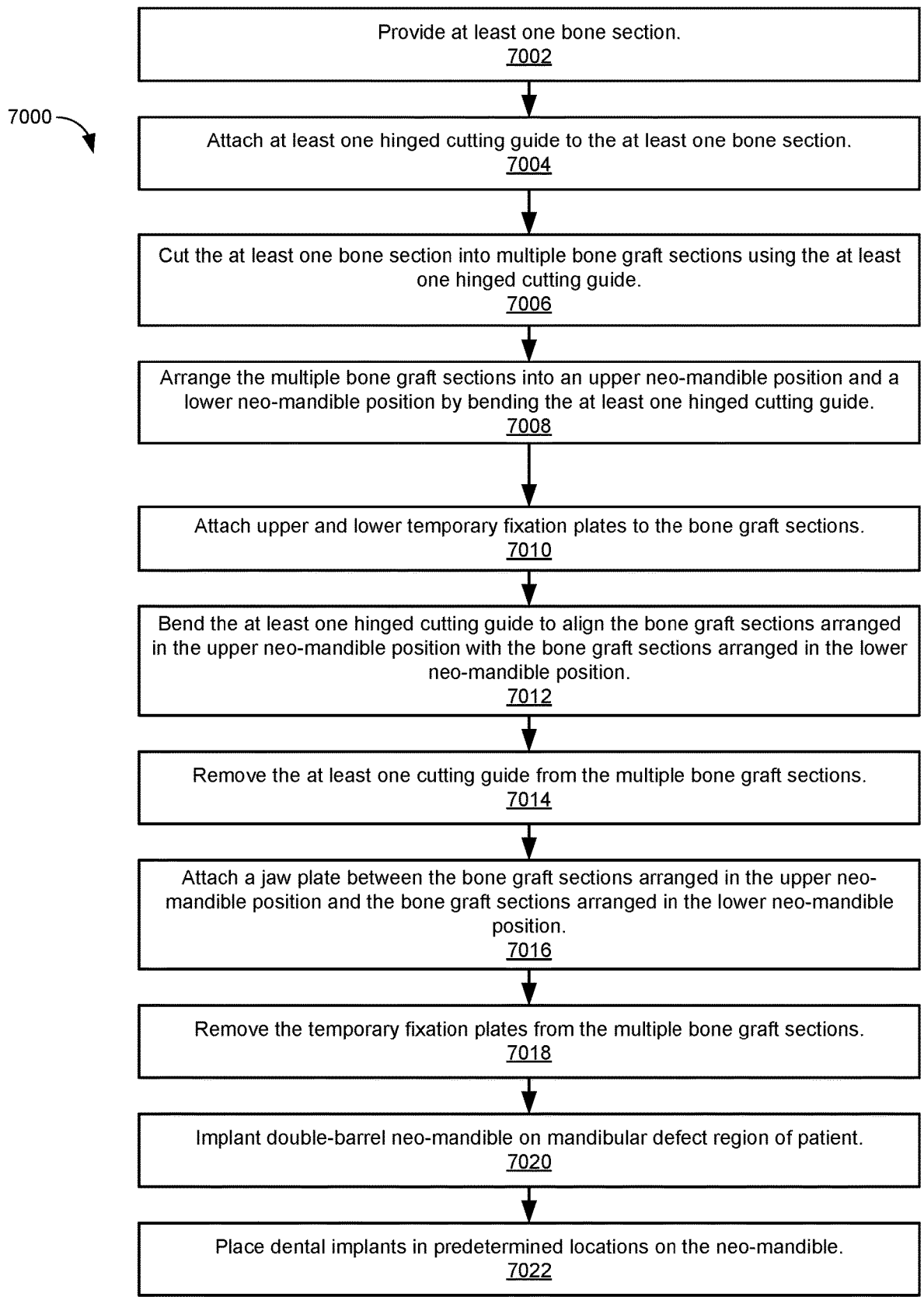
FIG. 70 is a flowchart illustrating a process for constructing a neo-mandible assembly according to some embodiments of the disclosed technologies.

FIG. 70 is a flowchart illustrating a process 7000 for constructing a double-barrel neo-mandible assembly according to some embodiments of the disclosed technologies. The elements of the processes described in this disclosure are presented in one arrangement. However, it should be understood that one or more elements of each process may be performed in a different order, in parallel, omitted entirely, and the like. Furthermore, each process may include other elements in addition to those presented.

Referring to FIG. 70, the process 7000 may include providing at least one bone section, at 7002. For example, the bone section may be the bone section 5600 of FIG. 56.

Referring again to FIG. 70, the process 7000 may include attaching at least one cutting guide to the bone section, at 7004. For example, the cutting guide may include the hinged cutting guide 1100 of FIG. 11 or the hinged cutting guides 1300A and 1300B of FIGS. 13A and 13B. In some embodiments, the sections of the cutting guide may not be joined at all.

Referring again to FIG. 70, the process 7000 may include cutting the at least one bone section into multiple bone graft sections using the cutting guide, at 7006. For example, the multiple bone graft sections may be as shown in FIG. 58.

Referring again to FIG. 70, the process 7000 may include arranging the multiple bone graft sections into an upper neo-mandible position and a lower neo-mandible position, at 7008. For example, the multiple bone graft sections may be arranged as shown in FIG. 59. In embodiments using a hinged cutting guide comprising two cutting guides joined by a hinge, the multiple bone graft sections may be arranged by rotating the cutting guides about the hinge.

Referring again to FIG. 70, the process 7000 may include attaching upper and lower temporary fixation plates to the multiple bone graft sections, at 7010. For example, the upper and lower temporary fixation plates may be attached to the multiple bone graft sections as shown in, and described with reference to, FIG. 66.

Referring again to FIG. 70, the process 7000 may include aligning the bone graft sections arranged in the upper neo-mandible position with the bone graft sections arranged in the lower neo-mandible position, at 7012. For example, the at least one hinged cutting guide may be bent as shown in FIG. 67. In embodiments using a hinged cutting guide, the bone graft sections may be arranged by bending the hinged cutting guide about the hinges.

Referring again to FIG. 70, the process 7000 may include removing the at least one cutting guide from the multiple bone graft sections, at 7014.

The process 7000 may include attaching a jaw plate between the bone graft sections arranged in the upper neo-mandible position and the bone graft sections arranged in the lower neo-mandible position, at 7014. For example, the jaw plate may be attached to the multiple bone graft sections as shown in FIG. 68.

Referring again to FIG. 70, the process 7000 may include removing the temporary fixation plates from the multiple bone graft sections, at 7018 to create a single-barrel neo-mandible. The process 7000 may include implanting the double-barrel neo-mandible on a mandibular defect region of a patient, at 7020. The process 7200 may include placing dental implants in predetermined locations on the neo-mandible, at 7022. The dental implants may be commercially-available dental implants.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims. In addition, each reference provided herein in incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

What is claimed is:

1. A method comprising:
    attaching a hinged cutting guide to a bone section, wherein the hinged cutting guide comprises a first cutting guide section and a second cutting guide section joined by a hinge;
    cutting the bone section into a first bone graft section using the first cutting guide section and a second bone graft section using the second cutting guide section;
    arranging the first and second bone graft sections in a neo-mandible position, wherein arranging the first and second bone graft sections in a neo-mandible position comprises pivoting the first and second cutting guide sections about the hinge;
    attaching a temporary fixation plate to the first and second bone graft sections after arranging the first and second bone graft sections in the neo-mandible position;
    removing the hinged cutting guide from the first and second bone graft sections after attaching the temporary fixation plate;
    attaching a final fixation plate to the first and second bone graft sections after removing the hinged cutting guide; and
    removing the temporary fixation plate from the first and second bone graft sections after attaching the final fixation plate to create a neo-mandible assembly.

2. The method of claim 1, wherein attaching the temporary fixation plate to the first and second bone graft sections comprises:
    attaching the temporary fixation plate to cephalic surfaces of the first and second bone graft sections.

3. The method of claim 1, wherein attaching the temporary fixation plate to the first and second bone graft sections comprises:
    attaching the temporary fixation plate to the first and second bone graft sections with multiple screws.

4. The method of claim 1, wherein attaching the temporary fixation plate to the first and second bone graft sections comprises:
    attaching the temporary fixation plate to the first and second bone graft sections with multiple mono-cortical fixation screws.

5. The method of claim 1, further comprising:
    implanting the neo-mandible assembly on a mandibular defect region of a patient.

6. The method of claim 5, further comprising:
    placing dental implants in predetermined locations on the neo-mandible assembly.

7. The method of claim 1, further comprising:
    locking the first and second bone graft sections in a neo-mandible position using a lock after arranging the first and second bone graft sections in the neo-mandible position.

8. The method of claim 7, wherein the hinge comprises a lock holder, and wherein locking the first and second bone graft sections in a neo-mandible position comprises installing the lock at the lock holder.

9. A neo-mandible comprising:
    a first bone graft section and a second bone graft section arranged in a neo-mandible position;
    a hinged cutting guide comprising a first cutting guide section and a second cutting guide section joined by a hinge, wherein the first cutting guide section is attached to the first bone graft section and the second cutting guide section is attached to the second bone graft section, wherein the first cutting guide section comprises a first lock holder and the second cutting guide section comprises a second lock holder, and wherein the first and second bone graft sections are arranged in the neo-mandible position by pivoting the first and second cutting guide sections about the hinge;
    a lock comprising a first dowel pin and a second dowel pin, wherein the lock is configured to lock the first and second cutting guide sections in the neo-mandible position based on inserting the first dowel pin into the first lock holder and the second dowel pin into the second lock holder; and a temporary fixation plate attached to the first and second bone graft sections.

10. The neo-mandible of claim 9, further comprising:
an alignment guide; and
wherein the alignment guide is attached to the first and second cutting guide sections.

11. The neo-mandible of claim 9, wherein the temporary fixation plate is attached to cephalic surfaces of the first and second bone graft sections.

12. The neo-mandible of claim 9, wherein the temporary fixation plate is attached to the first and second bone graft sections with multiple screws.

13. The neo-mandible of claim 9, wherein the temporary fixation plate is attached to the first and second bone graft sections with multiple mono-cortical fixation screws.

14. A method comprising:
attaching a first hinged cutting guide and a second hinged cutting guide to at least one bone section, wherein the first hinged cutting guide comprises a first cutting guide section and a second cutting guide section joined by a first hinge, and wherein the second hinged cutting guide comprises a third cutting guide section and a fourth cutting guide section joined by a second hinge;
cutting the at least one bone section into a first bone graft section using the first cutting guide section, a second bone graft section using the second cutting guide section, a third bone graft section using the third cutting guide section, and a fourth bone graft section using the fourth cutting guide section;
arranging the first and second bone graft sections into an upper neo-mandible position using the first and second cutting guide sections, wherein arranging the arranging the first and second bone graft sections into the upper neo-mandible position comprises pivoting or more of the plurality of the first and second cutting guide sections about the first hinge;
arranging the third and fourth bone graft sections into a lower neo-mandible position using the third and fourth cutting guide sections, wherein arranging the arranging the third and fourth bone graft sections into the lower neo-mandible position comprises pivoting the third and fourth cutting guide sections about the second hinge;
attaching an upper temporary fixation plate to the first and second bone graft sections arranged in the upper neo-mandible position;
attaching a lower temporary fixation plate to the third and fourth bone graft sections arranged in the lower neo-mandible position;
removing the first hinged cutting guide from the first and second bone graft sections after attaching the upper temporary fixation plate and removing the second hinged cutting guide from the third and fourth bone graft sections after attaching the lower temporary fixation plate;
attaching, after removing the first and second hinged cutting guides, a final fixation plate between the first and second bone graft sections arranged in the upper neo-mandible position and the third and fourth bone graft sections arranged in the lower neo-mandible position; and
removing the upper temporary fixation plate from the first and second bone graft sections and removing the lower temporary fixation plate from the third and fourth bone graft sections after attaching the final fixation plate to create a neo-mandible assembly.

15. The method of claim 14, further comprising:
aligning the first and second bone graft sections arranged in the upper neo-mandible position with the third and fourth bone graft sections arranged in the lower neo-mandible position prior to attaching the final fixation plate.

16. The method of claim 15, wherein:
the first and second hinged cutting guides are joined by a third hinge; and
aligning the upper neo-mandible position with the lower neo-mandible position comprises rotating the first and second hinged cutting guides about the third hinge.

17. The method of claim 14, wherein:
the method further comprises attaching an alignment guide to at least one of the first and second hinged cutting guides.

18. The method of claim 14, wherein:
attaching the upper temporary fixation plate to the first and second bone graft sections arranged in the upper neo-mandible position comprises attaching the upper temporary fixation plate to cephalic surfaces of the first and second bone graft sections arranged in the upper neo-mandible position; and
attaching the lower temporary fixation plate to the third and fourth bone graft sections arranged in the lower neo-mandible position comprises attaching the lower temporary fixation plate to cephalic surfaces of the third and fourth bone graft sections arranged in the lower neo-mandible position.

19. The method of claim 14, wherein attaching the upper and lower temporary fixation plates comprises:
attaching the upper and lower temporary fixation plates with multiple screws.

20. The method of claim 19, wherein the multiple screws are mono-cortical fixation screws.

21. The method of claim 14, further comprising:
implanting the neo-mandible assembly on a mandibular defect region of a patient.

22. The method of claim 21, further comprising:
placing dental implants in predetermined locations on the neo-mandible assembly.

* * * * *

UNITED STATES PATENT AND TRADEMARK OFFICE
CERTIFICATE OF CORRECTION

PATENT NO. : 12,295,849 B2
APPLICATION NO. : 18/440910
DATED : May 13, 2025
INVENTOR(S) : Jason D. Toranto Page 1 of 1

It is certified that error appears in the above-identified patent and that said Letters Patent is hereby corrected as shown below:

In the Claims

Column 27, Line 34, (Claim 14), change "pivoting or more of" to --pivoting--;

Column 27, Line 35, (Claim 14), change "the plurality of the first" to --the first--.

Signed and Sealed this
Twenty-second Day of July, 2025

Coke Morgan Stewart
*Acting Director of the United States Patent and Trademark Office*